(12) United States Patent
Zhang et al.

(10) Patent No.: US 11,459,337 B2
(45) Date of Patent: Oct. 4, 2022

(54) ISOTHIAZOLO[5,4-D]PYRIMIDINE COMPOUND AS IRAK4 INHIBITOR

(71) Applicant: CHIA TAI TIANQING PHARMACEUTICAL GROUP CO., LTD., Lianyungang (CN)

(72) Inventors: Yang Zhang, Shanghai (CN); Jianfei Wang, Shanghai (CN); Haizhong Tan, Shanghai (CN); Jie Li, Shanghai (CN); Jian Li, Shanghai (CN); Shuhui Chen, Shanghai (CN)

(73) Assignee: Chia Tai Tianqing Pharmaceutical Group Co., Inc., Lianyungang (CN)

( * ) Notice: Subject to any disclaimer, the term of this patent is extended or adjusted under 35 U.S.C. 154(b) by 0 days.

(21) Appl. No.: 17/254,778

(22) PCT Filed: Jun. 25, 2019

(86) PCT No.: PCT/CN2019/092867
§ 371 (c)(1),
(2) Date: Dec. 21, 2020

(87) PCT Pub. No.: WO2020/001449
PCT Pub. Date: Jan. 2, 2020

(65) Prior Publication Data
US 2021/0269459 A1   Sep. 2, 2021

(30) Foreign Application Priority Data

Jun. 25, 2018 (CN) .......................... 201810662580.9
May 30, 2019 (CN) .......................... 201910463156.6

(51) Int. Cl.
*C07D 513/04* (2006.01)
*C07D 519/00* (2006.01)

(52) U.S. Cl.
CPC ......... *C07D 513/04* (2013.01); *C07D 519/00* (2013.01)

(58) Field of Classification Search
CPC .................................................. C07D 513/04
USPC .................................................. 514/210.21
See application file for complete search history.

(56) References Cited

U.S. PATENT DOCUMENTS

2015/0094305 A1   4/2015   Romero

FOREIGN PATENT DOCUMENTS

| CN | 106232122 A | 12/2016 |
| WO | WO 2013/024291 A2 | 2/2013 |
| WO | WO 2013/068458 A1 | 5/2013 |
| WO | WO 2017/004133 A1 | 1/2017 |
| WO | WO 2017/205766 A1 | 11/2017 |

OTHER PUBLICATIONS

International Search Report in International Patent Application No. PCT/CN2019/092867, dated Sep. 27, 2019 (4 pages).
Extended European Search Report in European Patent Application No. EP 19825725.5, dated Feb. 14, 2022 (6 pages).
Hynes, Jr., J. & Nair, S. K., "Advances in the Discovery of Small-Molecule IRAK4 Inhibitors," Annual Reports in Medicinal Chemistry, vol. 49, pp. 117-133, ISSN 0065-7743 (2014).

*Primary Examiner* — Kahsay Habte
(74) *Attorney, Agent, or Firm* — Nixon Peabody LLP

(57) ABSTRACT

Disclosed in the present invention are an IRAK4 inhibitor, and an application thereof in preparation of a drug for treating IRAK4-related diseases. Specifically disclosed are a compound represented by formula (III) and a pharmaceutically acceptable salt thereof.

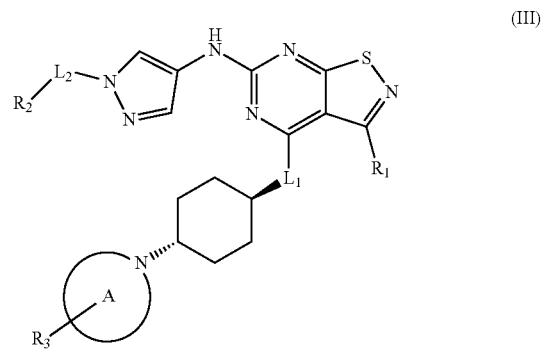

20 Claims, 1 Drawing Sheet

ISOTHIAZOLO[5,4-D]PYRIMIDINE COMPOUND AS IRAK4 INHIBITOR

CROSS-REFERENCE TO RELATED APPLICATIONS

This application is a U.S. national stage of PCT/CN2019/092867 filed on Jun. 25, 2019, which claims the benefits and priority of Chinese Patent No. 201810662580.9 filed on Jun. 25, 2018, and Chinese Patent No. 201910463156.6 filed on May 30, 2019 to the National Intellectual Property Administration, PRC, which are incorporated herein by reference in their entirety.

TECHNICAL FIELD

The present invention relates to an IRAK4 inhibitor and use thereof in preparing a medicament for treating IRAK4-related diseases, in particular to a compound of formula (I) and a pharmaceutically acceptable salt thereof.

BACKGROUND

Interleukin-1 receptor associated kinase 4 (IRAK4) is a serine/threonine-specific protein kinase, a member of tyrosine-like kinase (TLK) family, and a key node in the innate immune response involving interleukin-1, 18 and 33, and toll-like receptors. After extracellular signal molecules bind to interleukin receptors or toll-like receptors, proteins are recruited to form a MyD88:IRAK4:IRAK1/2 complex, leading to IRAK1/2 phosphorylation which mediates a series of downstream signaling Thus p38, JNK, and NF-κB signaling pathways are activated, eventually promoting the expression of proinflammatory cytokines. Clinical pathology studies have shown that individuals with IRAK4 mutations have resistance against chronic lung disease and inflammatory bowel disease. IRAK4 deficiency is not lethal in itself, and the individuals can survive to adulthood with a reduced risk of infection over age. Therefore, IRAK4 becomes an important therapeutic target attracting extensive research and development interest.

SUMMARY

The present invention provides a compound of formula (III), an optical isomer or a pharmaceutically acceptable salt thereof,

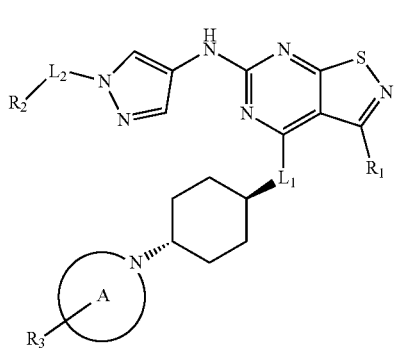

(III)

wherein,
$R_1$ is selected from the group consisting of CN, $C_{1-6}$ alkyl and 3-6 membered heterocycloalkyl, wherein the $C_{1-6}$ alkyl and 3-6 membered heterocycloalkyl are optionally substituted with 1, 2 or 3 $R_a$;

$R_2$ is selected from the group consisting of $C_{1-6}$ alkyl, $C_{3-8}$ cycloalkyl and 3-6 membered heterocycloalkyl, wherein the $C_{1-6}$ alkyl, $C_{3-8}$ cycloalkyl and 3-6 membered heterocycloalkyl are optionally substituted with 1, 2 or 3 $R_b$;

$R_3$ is selected from the group consisting of H, F, Cl, Br, I, OH, $NH_2$, CN, COOH, $C_{1-6}$ alkyl, $C_{1-6}$ alkylamino, —C(=O)—O—$C_{1-6}$ alkyl, —C(=O)—$C_{1-6}$ alkyl and $C_{3-6}$ cycloalkyl, wherein the $C_{1-6}$ alkyl, $C_{1-6}$ alkylamino, —C(=O)—O—$C_{1-6}$ alkyl, —C(=O)—$C_{1-6}$ alkyl and $C_{3-6}$ cycloalkyl are optionally substituted with 1, 2 or 3 $R_c$;

ring A is selected from the group consisting of 3-10 membered heterocycloalkyl, and ring A contains at least one nitrogen atom, wherein the 3-10 membered heterocycloalkyl is optionally substituted with 1, 2 or 3 $R_d$;

$L_1$ is selected from the group consisting of O and N ($R_4$);
$L_2$ is selected from the group consisting of a single bond, $CH_2$ and $CH_2CH_2$;
$R_4$ is selected from the group consisting of H and Me;
each $R_a$ is independently selected from the group consisting of H, F, Cl, Br, I, OH, $NH_2$, CN and COOH;
each $R_b$ is independently selected from the group consisting of H, F, Cl, Br, I, OH, $NH_2$, COOH and Me;
each $R_c$ is independently selected from the group consisting of H, F, Cl, Br, I, OH, $NH_2$ and CN;
each $R_d$ is independently selected from the group consisting of H, F, Cl, Br, I, OH, $NH_2$ and CN;
the 3-6 membered heterocycloalkyl contains 1, 2 or 3 heteroatoms or heteroatom groups independently selected from the group consisting of —O—, —S—, —NH— and N; and
the 3-10 membered heterocycloalkyl contains 1, 2 or 3 heteroatoms or heteroatom groups independently selected from the group consisting of —O—, —S—, —NH—, N, and —C(=O)NH—.

The present invention further provides a compound of formula (II), an optical isomer or a pharmaceutically acceptable salt thereof,

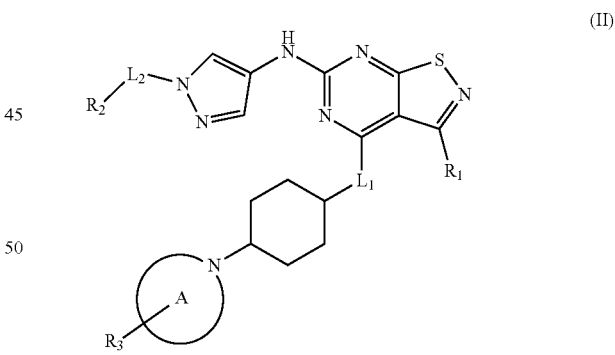

(II)

wherein,
$R_1$ is selected from the group consisting of $C_{1-6}$ alkyl and 3-6 membered heterocycloalkyl, wherein the $C_{1-6}$ alkyl and 3-6 membered heterocycloalkyl are optionally substituted with 1, 2 or 3 $R_a$;

$R_2$ is selected from the group consisting of $C_{1-6}$ alkyl and 3-6 membered heterocycloalkyl, wherein the $C_{1-6}$ alkyl and 3-6 membered heterocycloalkyl are optionally substituted with 1, 2 or 3 $R_b$;

$R_3$ is selected from the group consisting of H, F, Cl, Br, I, OH, $NH_2$, CN, $C_{1-6}$ alkyl, —C(=O)—O—$C_{1-6}$ alkyl, —C(=O)—$C_{1-6}$ alkyl and $C_{3-6}$ cycloalkyl, wherein the $C_{1-6}$ alkyl, —C(=O)—O—$C_{1-6}$ alkyl, —C(=O)—$C_{1-6}$ alkyl and $C_{3-6}$ cycloalkyl is optionally substituted with 1, 2 or 3 $R_c$;

ring A is selected from the group consisting of 3-10 membered heterocycloalkyl, and ring A contains at least one nitrogen atom, wherein the 3-10 membered heterocycloalkyl is optionally substituted with 1, 2 or 3 $R_d$;

$L_1$ is selected from the group consisting of O and N ($R_4$);

$L_2$ is selected from the group consisting of a single bond, $CH_2$ and $CH_2CH_2$;

$R_4$ is selected from the group consisting of H and Me;

each $R_a$ is independently selected from the group consisting of H, F, Cl, Br, I, OH, $NH_2$, CN and COOH;

each $R_b$ is independently selected from the group consisting of H, F, Cl, Br, I, OH, $NH_2$, COOH and Me;

each $R_c$ is independently selected from the group consisting of H, F, Cl, Br, I, OH, $NH_2$ and CN;

each $R_d$ is independently selected from the group consisting of H, F, Cl, Br, I, OH, $NH_2$ and CN;

the 3-6 membered heterocycloalkyl contains 1, 2 or 3 heteroatoms or heteroatom groups independently selected from the group consisting of —O—, —S—, —NH— and N; and the 3-10 membered heterocycloalkyl contains 1, 2 or 3 heteroatoms or heteroatom groups independently selected from the group consisting of —O—, —S—, —NH—, N, and —C(=O)NH—.

The present invention further provides a compound of formula (I), an optical isomer or a pharmaceutically acceptable salt thereof,

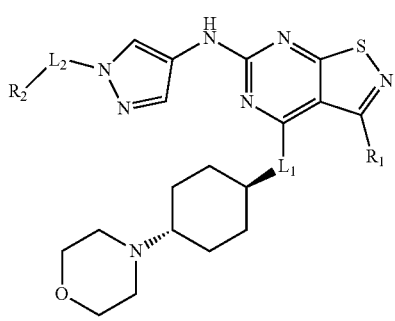

(I)

wherein, $R_1$ is selected from the group consisting of $C_{1-6}$ alkyl and 3-6 membered heterocycloalkyl, wherein the $C_{1-6}$ alkyl and 3-6 membered heterocycloalkyl are optionally substituted with 1, 2 or 3 $R_a$;

$R_2$ is selected from the group consisting of $C_{1-6}$ alkyl and 3-6 membered heterocycloalkyl, wherein the $C_{1-6}$ alkyl and 3-6 membered heterocycloalkyl are optionally substituted with 1, 2 or 3 $R_b$;

each $R_a$ is independently selected from the group consisting of F, Cl, Br, I, OH and $NH_2$;

each $R_b$ is independently selected from the group consisting of F, Cl, Br, I, OH and $NH_2$;

$L_1$ is selected from the group consisting of O, S and NH;

$L_2$ is selected from the group consisting of a single bond, $CH_2$ and $CH_2CH_2$; and the 3-6 membered heterocycloalkyl contains 1, 2 or 3 heteroatoms or heteroatom groups independently selected from the group consisting of —O—, —S—, —NH— and N.

In some embodiments of the present invention, the $L_1$ described above is selected from the group consisting of O and N($R_4$), while the other variables are as defined herein.

In some embodiments of the present invention, $R_1$ is selected from the group consisting of CN, $C_{1-6}$ alkyl, 3 membered heterocycloalkyl, 4 membered heterocycloalkyl, 5 membered heterocycloalkyl and 6 membered heterocycloalkyl, wherein the $C_{1-6}$ alkyl, 3 membered heterocycloalkyl, 4 membered heterocycloalkyl, 5 membered heterocycloalkyl and 6 membered heterocycloalkyl are optionally substituted with 1, 2 or 3 $R_a$, while the other variables are as defined herein.

In some embodiments of the present invention, $R_1$ above is selected from the group consisting of $C_{1-3}$ alkyl and 6 membered heterocycloalkyl, wherein the $C_{1-3}$ alkyl and 6 membered heterocycloalkyl are optionally substituted with 1, 2 or 3 $R_a$, while the other variables are as defined herein.

In some embodiments of the present invention, $R_1$ above is selected from the group consisting of $C_{1-3}$ alkyl and tetrahydropyranyl, wherein the $C_{1-3}$ alkyl and tetrahydropyranyl are optionally substituted with 1, 2 or 3 $R_a$, while the other variables are as defined herein.

In some embodiments of the present invention, $R_1$ above is selected from the group consisting of methyl, ethyl, isopropyl and tetrahydropyranyl, wherein the methyl, ethyl, isopropyl and tetrahydropyranyl are optionally substituted with 1, 2 or 3 $R_a$, while the other variables are as defined herein.

In some embodiments of the present invention, $R_1$ above is selected from the group consisting of Me, Et,

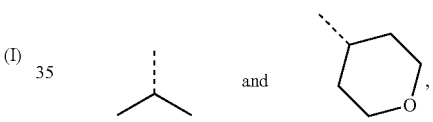

wherein the Me, Et,

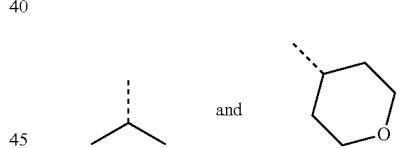

are optionally substituted with 1, 2, or 3 $R_a$, while the other variables are as defined herein.

In some embodiments of the present invention, each $R_a$ is independently selected from the group consisting of F, Cl, Br, I, OH, $NH_2$, CN and COOH, while the other variables are as defined herein.

In some embodiments of the present invention, each $R_a$ is independently selected from the group consisting of OH, CN, and COOH, while the other variables are as defined herein.

In some embodiments of the present invention, $R_1$ above is selected from the group consisting of Me, Et,

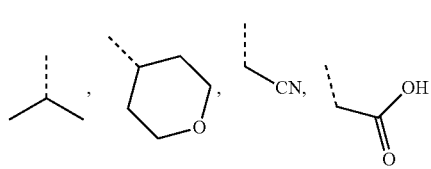

and 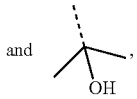, while the other variables are as defined herein. In some embodiments of the present invention, $R_1$ above is selected from the group consisting of Me, Et,

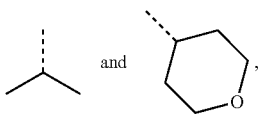, while the other variables are as defined herein.

In some embodiments of the present invention, $R_2$ above is selected from the group consisting of $C_{1-3}$ alkyl, $C_{4-6}$ cycloalkyl, tetrahydropyranyl, oxetanyl, tetrahydrofuranyl, and 1,4-dioxanyl, wherein the $C_{1-3}$ alkyl, $C_{4-6}$ cycloalkyl, tetrahydropyranyl, oxetanyl, tetrahydrofuranyl, and 1,4-dioxanyl are optionally substituted with 1, 2, or 3 $R_b$, while the other variables are as defined herein.

In some embodiments of the present invention, $R_2$ above is selected from the group consisting of $C_{1-6}$ alkyl, 3 membered heterocycloalkyl, 4 membered heterocycloalkyl, 5 membered heterocycloalkyl and 6 membered heterocycloalkyl, wherein the $C_{1-6}$ alkyl, 3 membered heterocycloalkyl, 4 membered heterocycloalkyl, 5 membered heterocycloalkyl and 6 membered heterocycloalkyl are optionally substituted with 1, 2 or 3 $R_b$, while the other variables are as defined herein.

In some embodiments of the present invention, $R_2$ above is selected from the group consisting of $C_{1-3}$ alkyl, 4 membered heterocycloalkyl, 5 membered heterocycloalkyl and 6 membered heterocycloalkyl, wherein the $C_{1-3}$ alkyl, 4 membered heterocycloalkyl, 5 membered heterocycloalkyl and 6 membered heterocycloalkyl are optionally substituted with 1, 2 or 3 $R_b$, while the other variables are as defined herein. In some embodiments of the present invention, $R_2$ above is selected from the group consisting of $C_{1-3}$ alkyl, tetrahydropyranyl, oxetanyl, tetrahydrofuranyl and 1,4-dioxanyl, wherein the $C_{1-3}$ alkyl, tetrahydropyranyl, oxetanyl, tetrahydrofuranyl and 1,4-dioxanyl are optionally substituted with 1, 2 or 3 $R_b$, while the other variables are as defined herein.

In some embodiments of the present invention, $R_2$ above is selected from the group consisting of $C_{1-3}$ alkyl and tetrahydro-2H-pyranyl, wherein the $C_{1-3}$ alkyl and tetrahydropyranyl are optionally substituted with 1, 2 or 3 $R_b$, while the other variables are as defined herein. In some embodiments of the present invention, $R_2$ above is selected from the group consisting of Me, Et,

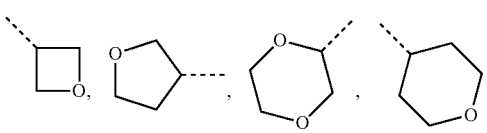

and cyclohexyl, wherein the Me, Et,

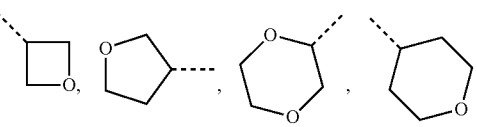

and cyclohexyl are optionally substituted with 1, 2, or 3 $R_b$, while the other variables are as defined herein.

In some embodiments of the present invention, $R_2$ above is selected from the group consisting of Me, Et,

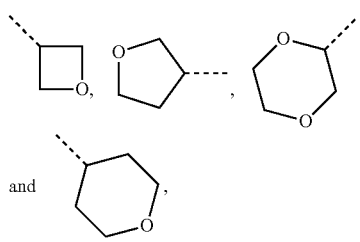

wherein the Me, Et,

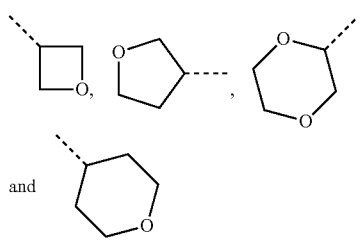

are optionally substituted with 1, 2, or 3 $R_b$, while the other variables are as defined herein.

In some embodiments of the present invention, $R_2$ above is selected from the group consisting of Me, Et,

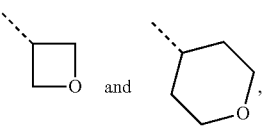, wherein the Me, Et,

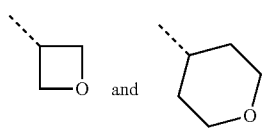

are optionally substituted with 1, 2, or 3 $R_b$, while the other variables are as defined herein.

In some embodiments of the present invention, each $R_b$ is independently selected from the group consisting of F, Cl, Br, I, OH, $NH_2$, COOH and Me.

In some embodiments of the present invention, each $R_b$ is independently selected from the group consisting of F, OH, $NH_2$, COOH and Me.

In some embodiments of the present invention, $R_2$ is selected from the group consisting of Me, —CH$_2$OH, Et,

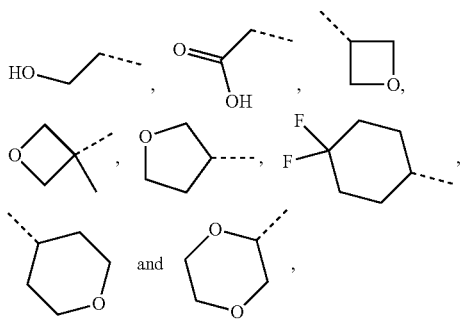

while the other variables are as defined herein.

In some embodiments of the present invention, $R_2$ above is selected from the group consisting of Me, —CH$_2$OH, Et,

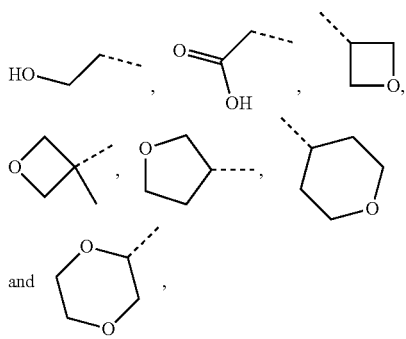

while the other variables are as defined herein.

In some embodiments of the present invention, $R_2$ above is selected from the group consisting of Me, Et,

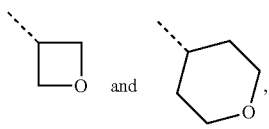

while the other variables are as defined herein.

In some embodiments of the present invention, $L_2$ above is a single bond.

In some embodiments of the present invention, the structural unit

above is selected from the group consisting of Me, Et,

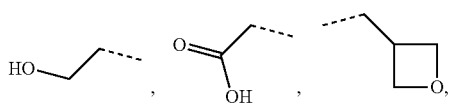

-continued

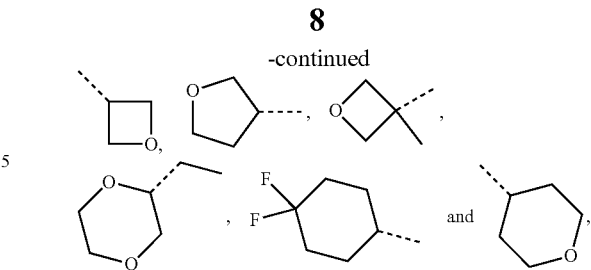

while the other variables are as defined herein.

In some embodiments of the present invention, the structural unit

above is selected from the group consisting of Me, Et,

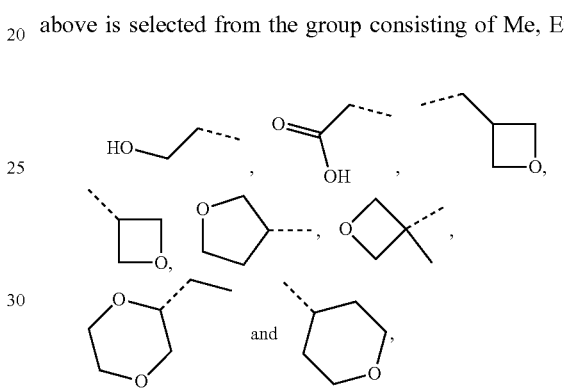

while the other variables are as defined herein.

In some embodiments of the present invention, the structural unit

above is selected from the group consisting of Me, Et,

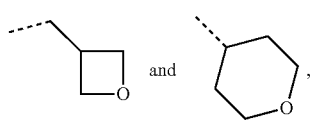

while the other variables are as defined herein.

In some embodiments of the present invention, $R_3$ above is selected from the group consisting of H, F, Cl, Br, I, OH, NH$_2$, CN, COOH, C$_{1-3}$ alkyl, —N(C$_{1-3}$ alkyl)$_2$, —C(=O)—O—C$_{1-3}$ alkyl, —C(=O)—C$_{1-3}$ alkyl and C$_{3-6}$ cycloalkyl, wherein the C$_{1-3}$ alkyl, —N(C$_{1-3}$ alkyl)$_2$, —C(=O)—O—C$_{1-3}$ alkyl, —C(=O)—C$_{1-3}$ alkyl and C$_{3-6}$ cycloalkyl are optionally substituted with 1, 2 or 3 R$_c$, while the other variables are as defined herein.

In some embodiments of the present invention, $R_3$ above is selected from the group consisting of H, F, Cl, Br, I, OH, NH$_2$, CN, C$_{1-3}$ alkyl, —C(=O)—O—C$_{1-3}$ alkyl, —C(=O)—C$_{1-3}$ alkyl and C$_{3-6}$ cycloalkyl, wherein the C$_{1-3}$ alkyl, —C(=O)—O—C$_{1-3}$ alkyl, —C(=O)—C$_{1-3}$ alkyl and C$_{3-6}$ cycloalkyl is optionally substituted with 1, 2 or 3 R$_c$, while the other variables are as defined herein.

In some embodiments of the present invention, each $R_c$ is independently selected from the group consisting of F, Cl, Br, I, OH, $NH_2$ and CN. In some embodiments of the present invention, $R_3$ above is selected from the group consisting of H, F, Cl, Br, I, OH, $NH_2$, CN, COOH, Me, Et,

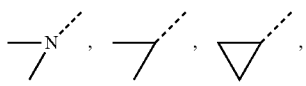

—C(=O)—O-Me, —C(=O)—O-Et and —C(=O)-Me, while the other variables are as defined herein.

In some embodiments of the present invention, $R_3$ above is selected from the group consisting of H, F, Cl, Br, I, OH, $NH_2$, CN, Me, Et,

—C(=O)—O-Me, —C(=O)—O-Et and —C(=O)-Me, while the other variables are as defined herein.

In some embodiments of the present invention, ring A above is selected from the group consisting of 3, 4, 5, 6, 7, 8, 9 or 10 membered heterocycloalkyl, wherein the 3, 4, 5, 6, 7, 8, 9 or 10 membered heterocycloalkyl is optionally substituted with 1, 2 or 3 $R_d$, while the other variables are as defined herein.

In some embodiments of the present invention, ring A above is selected from the group consisting of 4, 5, 6, 7 or 8 membered heterocycloalkyl, wherein the 4, 5, 6, 7 or 8 membered heterocycloalkyl is optionally substituted with 1, 2 or 3 $R_d$, while the other variables are as defined herein.

In some embodiments of the present invention, ring A above is selected from the group consisting of 4, 6, 7 or 8 membered heterocycloalkyl, wherein the 4, 6, 7 or 8 membered heterocycloalkyl is optionally substituted with 1, 2 or 3 $R_d$, while the other variables are as defined herein.

In some embodiments of the present invention, ring A above is selected from the group consisting of 6, 7 or 8 membered heterocycloalkyl, wherein the 6, 7 or 8 membered heterocycloalkyl is optionally substituted with 1, 2 or 3 $R_d$, while the other variables are as defined herein.

In some embodiments of the present invention, ring A above is selected from the group consisting of 6 or 7 membered heterocycloalkyl, wherein the 6 or 7 membered heterocycloalkyl is optionally substituted with 1, 2 or 3 $R_d$, while the other variables are as defined herein.

In some embodiments of the present invention, ring A above is selected from the group consisting of morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl, 2,5-diazabicyclo[2.2.1]heptyl and azetidinyl, wherein the morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl, 2,5-diazabicyclo[2.2.1]heptyl and azetidinyl are optionally substituted with 1, 2, or 3 $R_d$, while the other variables are as defined herein.

In some embodiments of the present invention, ring A above is selected from the group consisting of morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl and 2,5-diazabicyclo[2.2.1]heptyl, wherein the morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl and 2,5-diazabicyclo[2.2.1]heptyl are optionally substituted with 1, 2, or 3 $R_d$, while the other variables are as defined herein.

In some embodiments of the present invention, each $R_d$ is independently selected from the group consisting of F, Cl, Br, I, OH, $NH_2$ and CN.

In some embodiments of the present invention, ring A above is selected from the group consisting of morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl and 2,5-diazabicyclo[2.2.1]heptyl, while the other variables are as defined herein.

In some embodiments of the present invention, ring A above is selected from the group consisting of

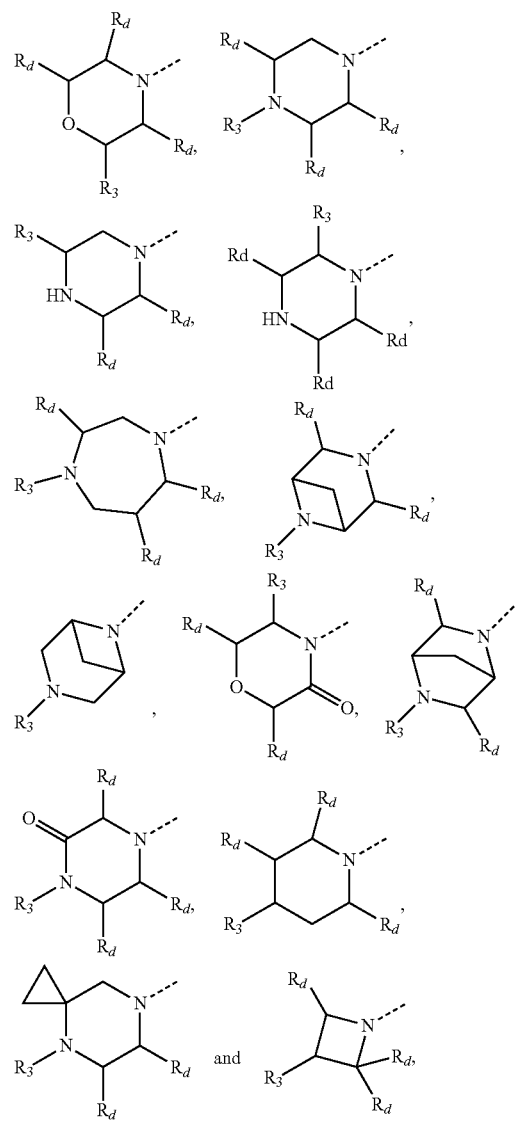

while the other variables are as defined herein.

In some embodiments of the present invention, ring A above is selected from the group consisting of

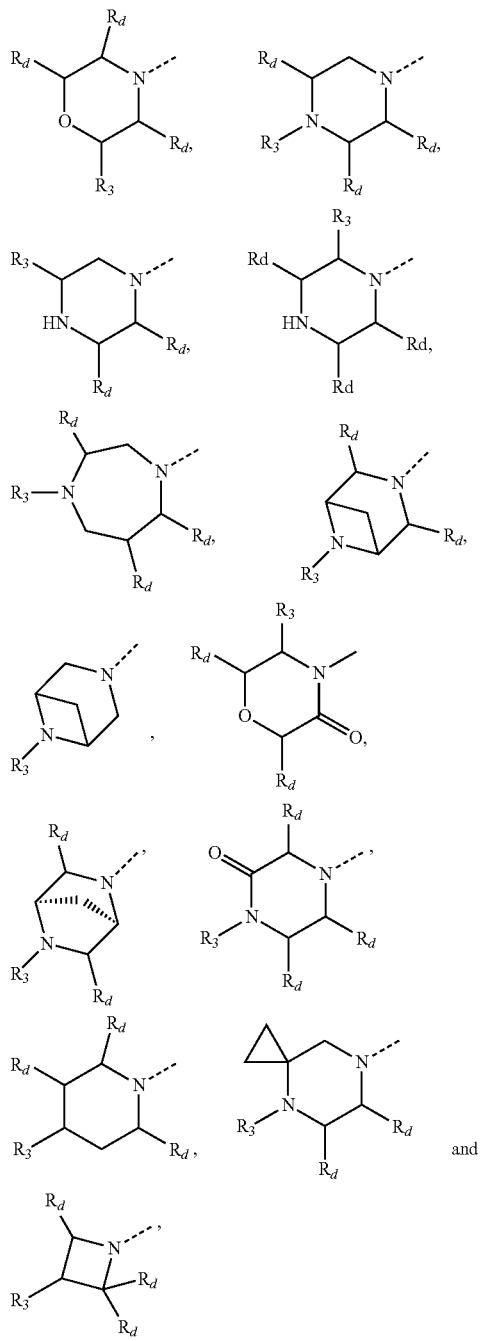
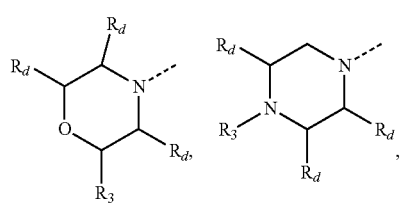
while the other variables are as defined herein.
In some embodiments of the present invention, ring A above is selected from the group consisting of
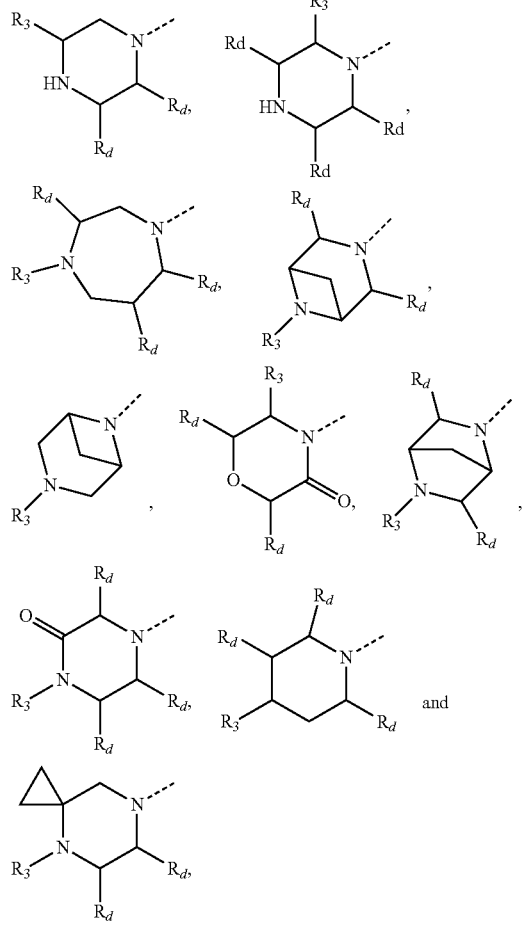
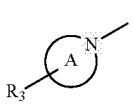
while the other variables are as defined herein.
In some embodiments of the present invention, the structural unit
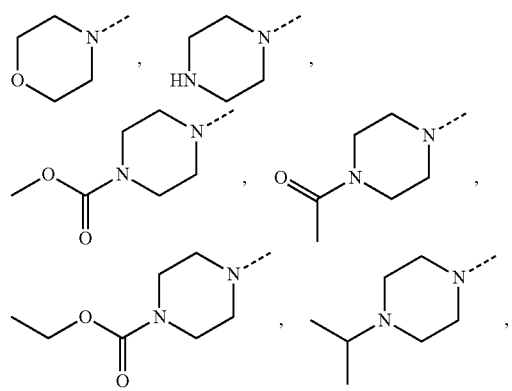
is selected from the group consisting of

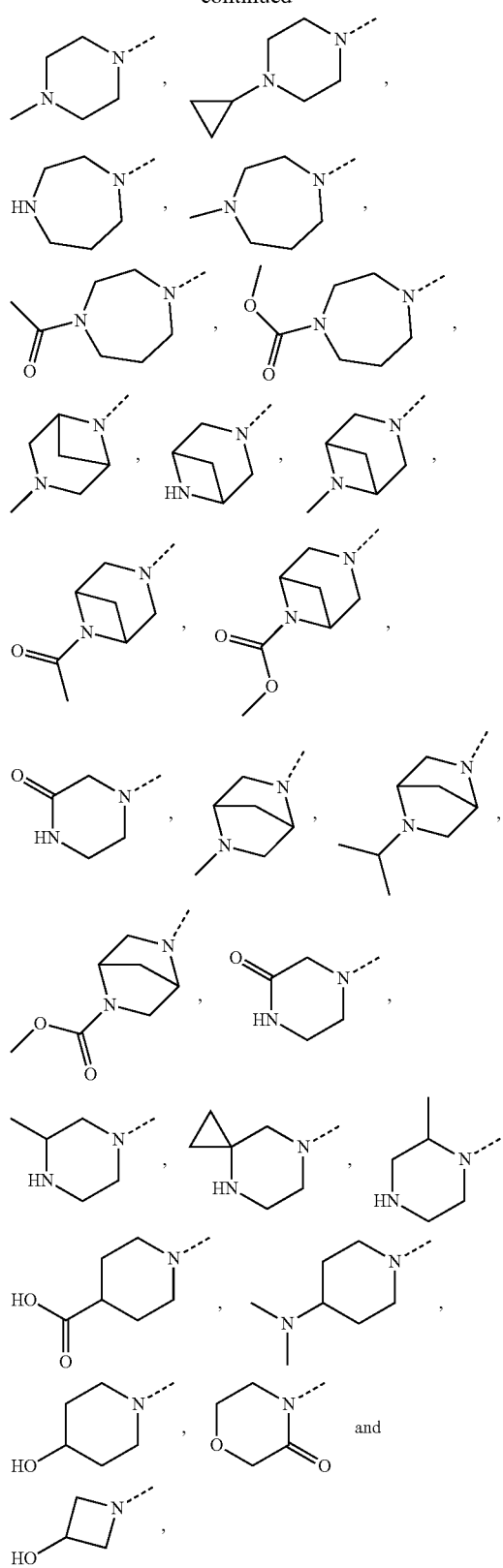
while the other variables are as defined herein.
In some embodiments of the present invention, the structural unit
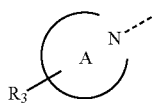
is selected from the group consisting of
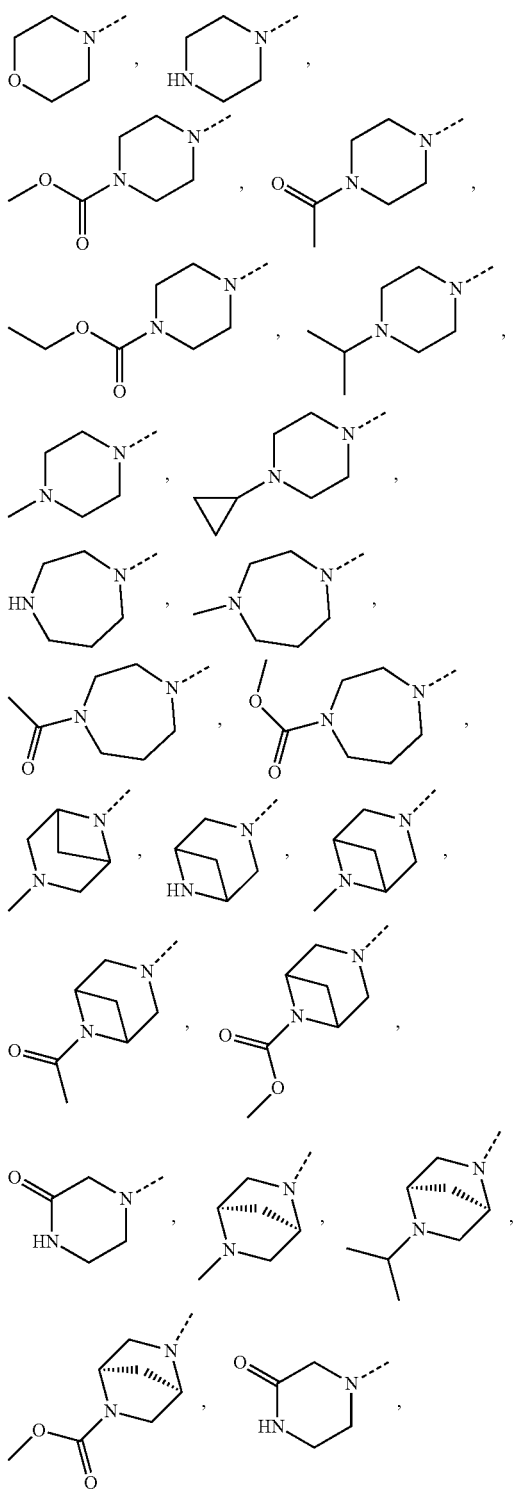

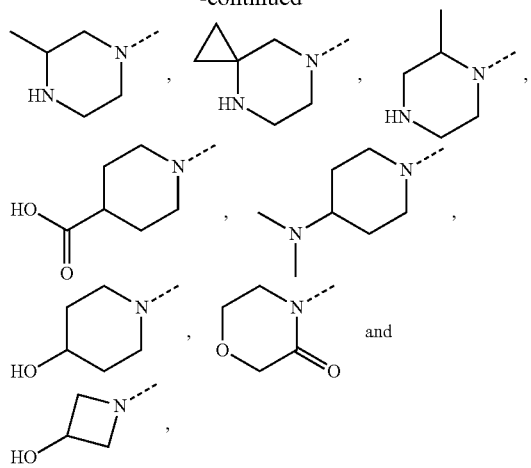
while the other variables are as defined herein.
In some embodiments of the present invention, the structural unit
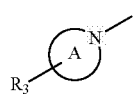
is selected from the group consisting of
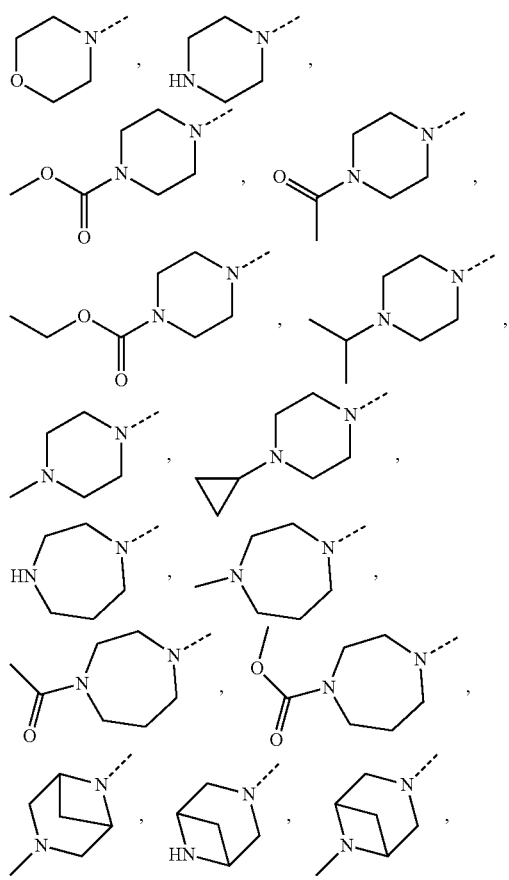
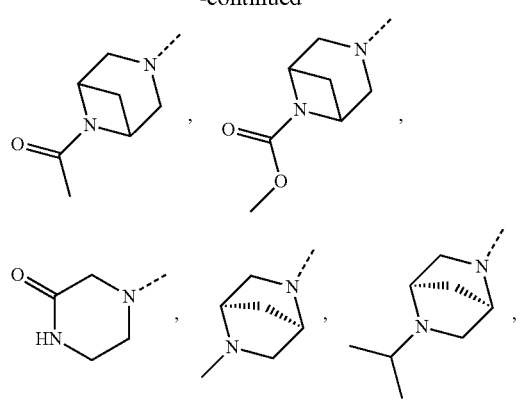
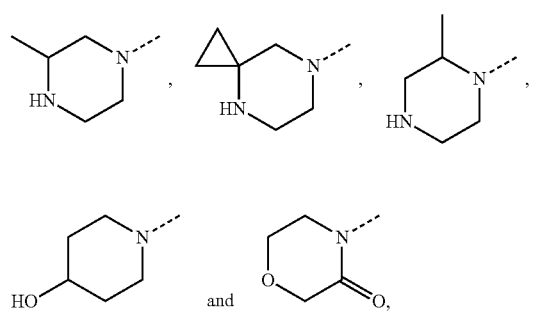
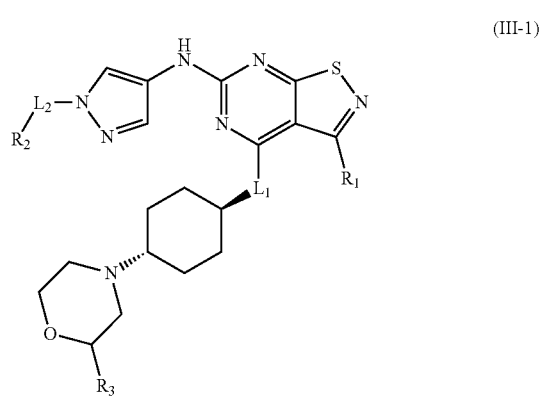
while the other variables are as defined herein.
In some embodiments of the present invention, the compound, optical isomer or pharmaceutically acceptable salt thereof, is selected from
(III-1)

(III-2)
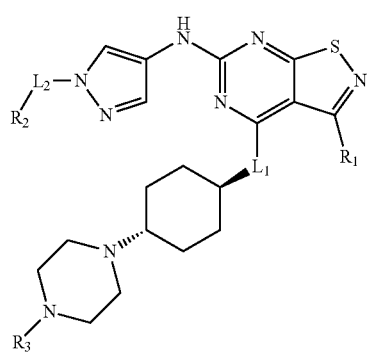
(III-3)
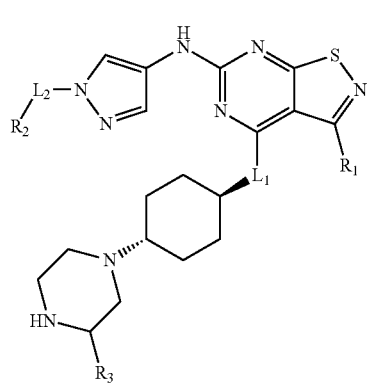
(III-4)
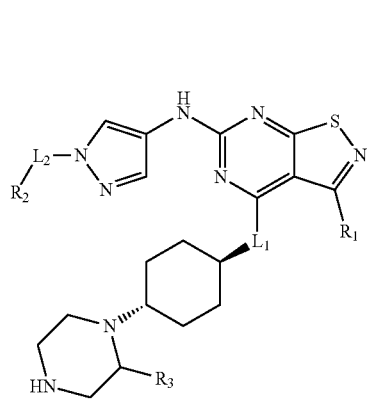
(III-5)
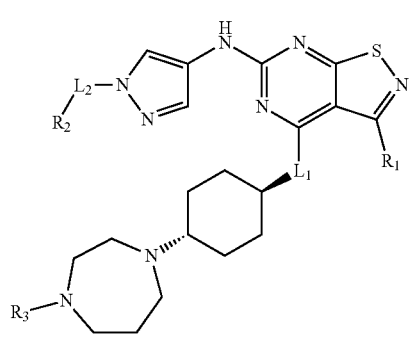
(III-6)
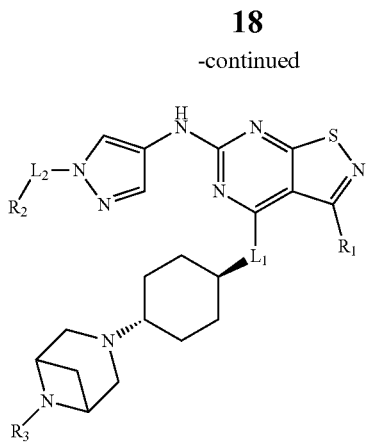
(III-7)
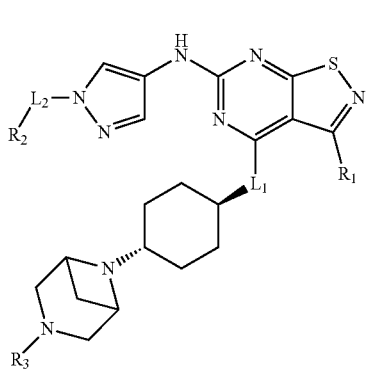
(III-8)
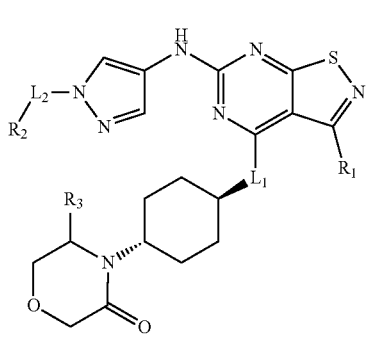
(III-9)
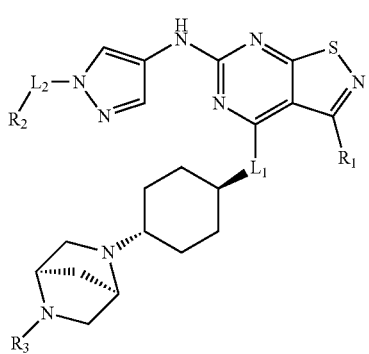

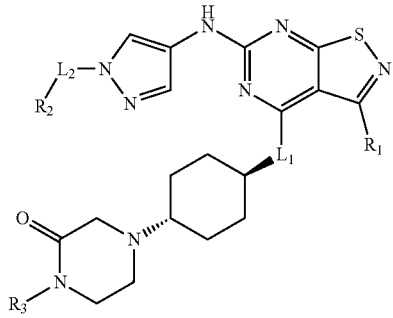
(III-10)
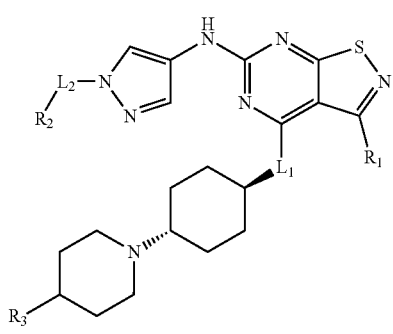
(III-11)
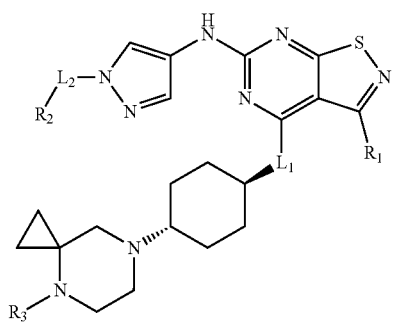
(III-12)
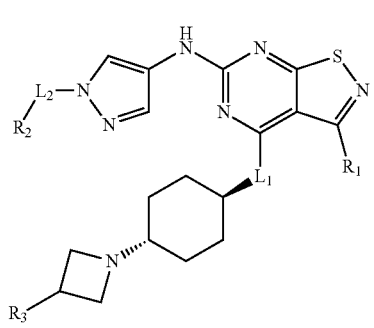
(III-13)
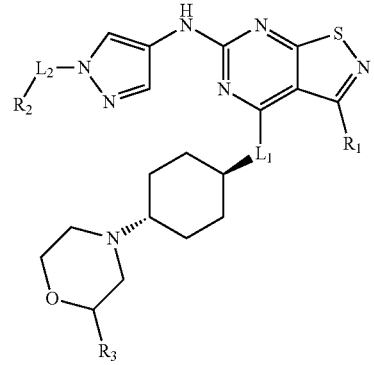
(III-1)
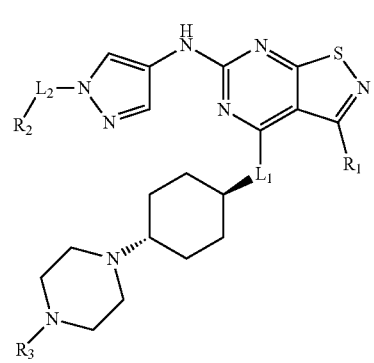
(III-2)
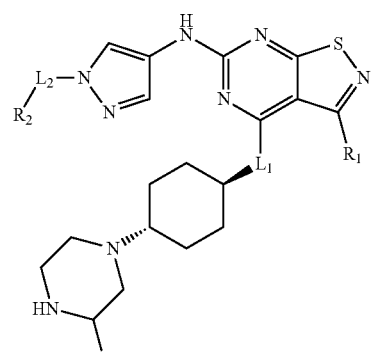
(III-3)
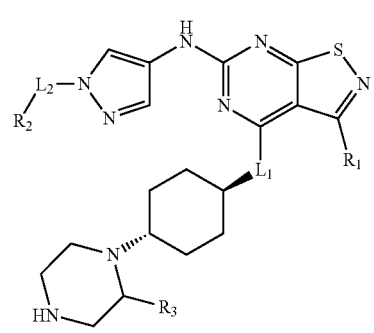
(III-4)

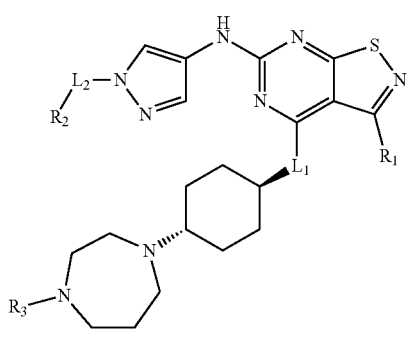
(III-5)
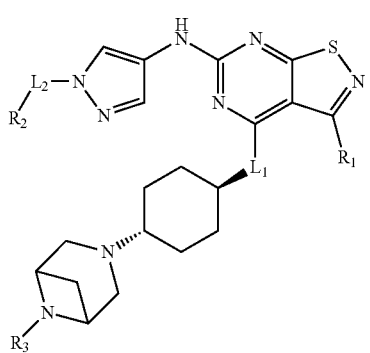
(III-6)
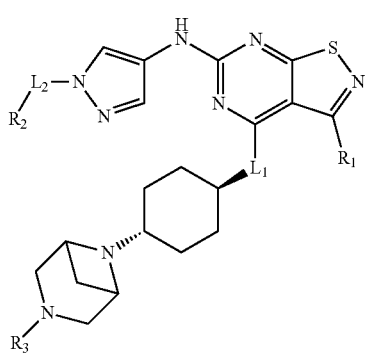
(III-7)
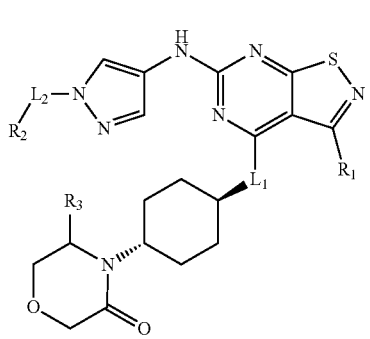
(III-8)
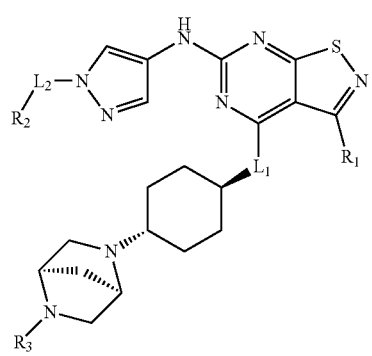
(III-9)
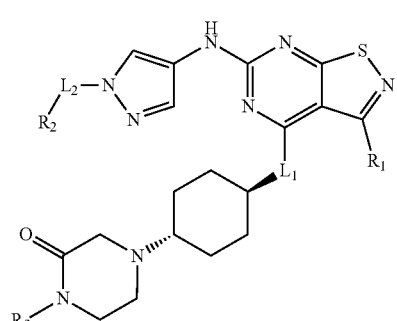
(III-10)
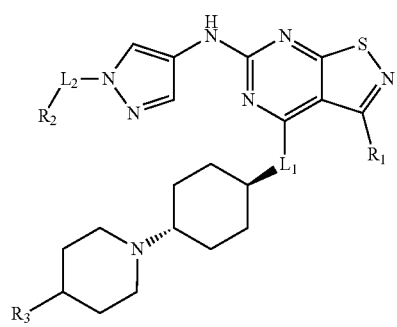
(III-11)
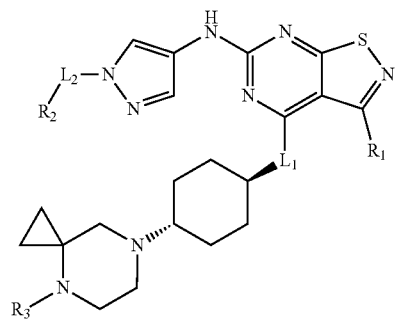
(III-12)

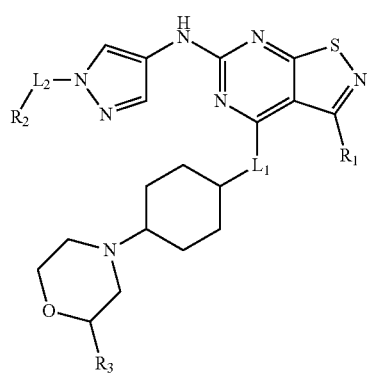 (II-1)
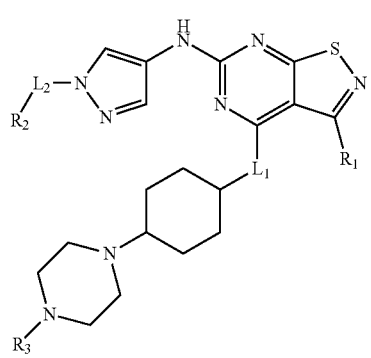 (II-2)
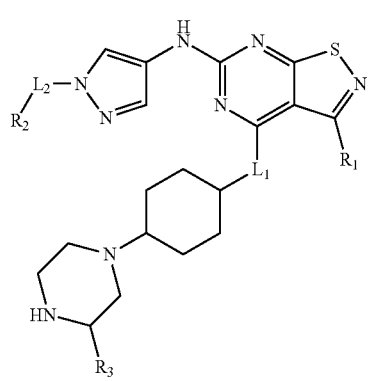 (II-3)
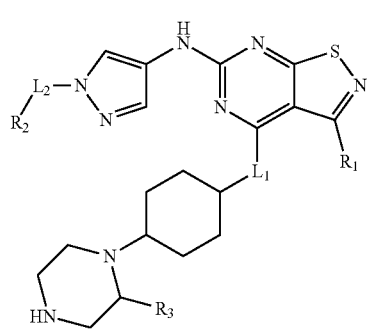 (II-4)
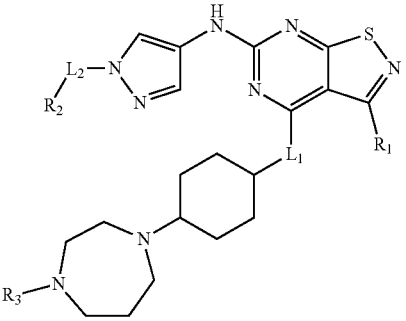 (II-5)
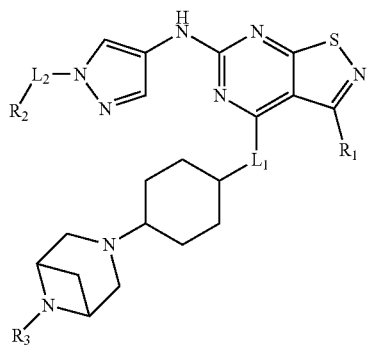 (II-6)
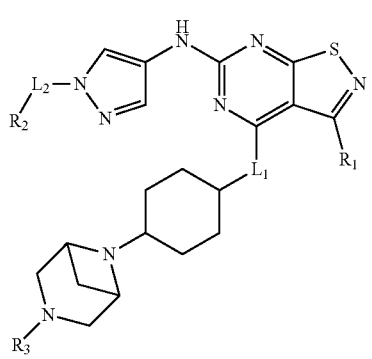 (II-7)
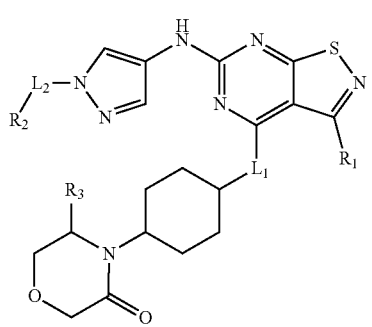 (II-8)

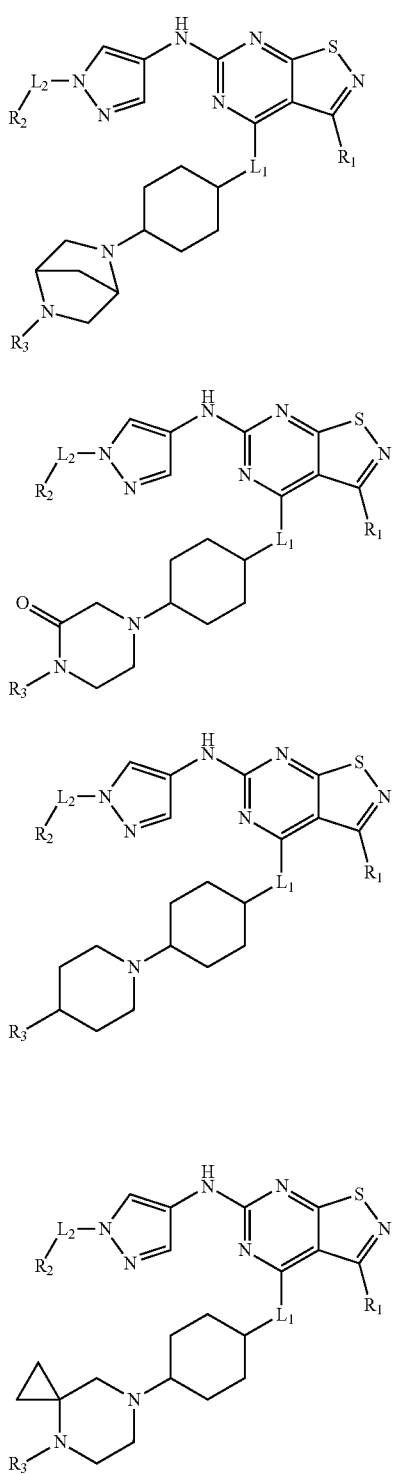
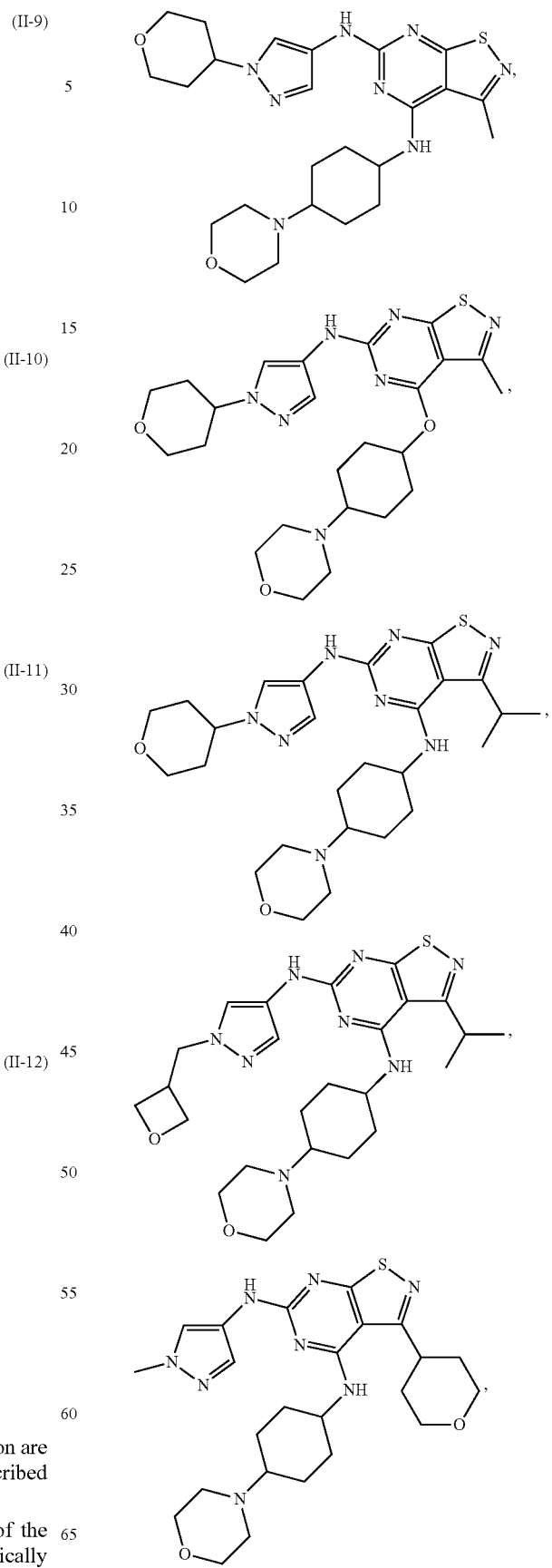
while $R_1$, $R_2$, $R_3$, $L_1$, and $L_2$ are as defined herein.
Still some other embodiments of the present invention are derived from any combination of the variables as described above.
The present invention also provides a compound of the following formula, an optical isomer or a pharmaceutically acceptable salt thereof, which is selected from:

27
-continued
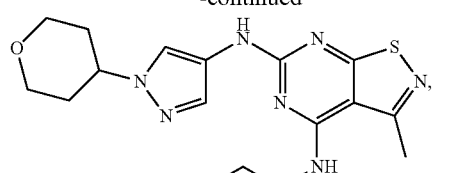
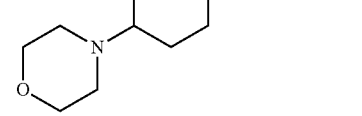
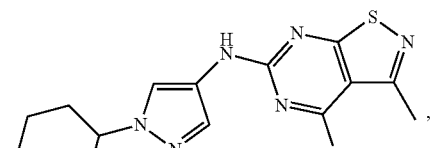
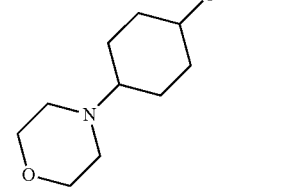
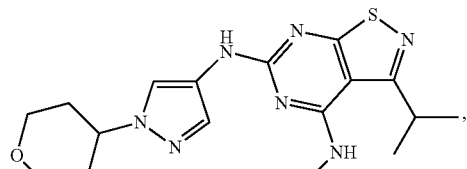
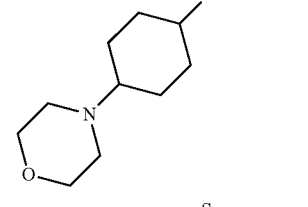
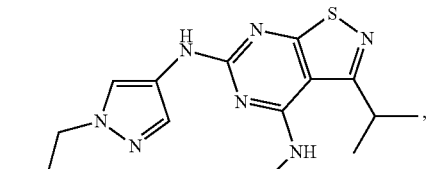
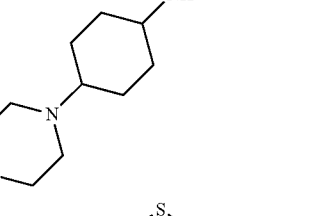
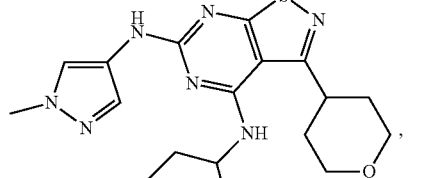
28
-continued
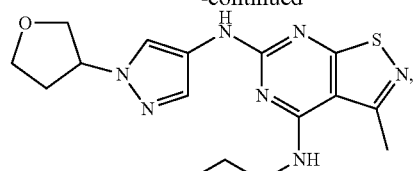
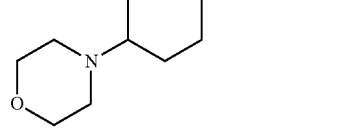
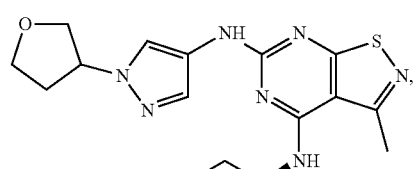
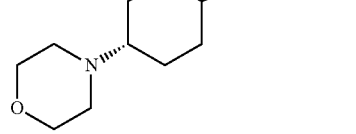
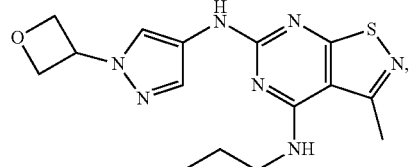
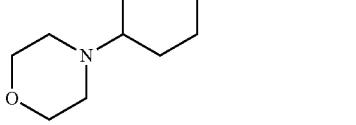
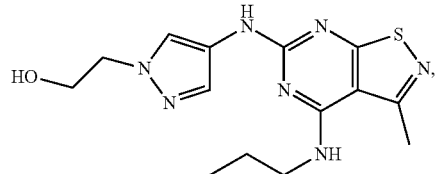
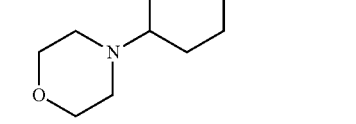
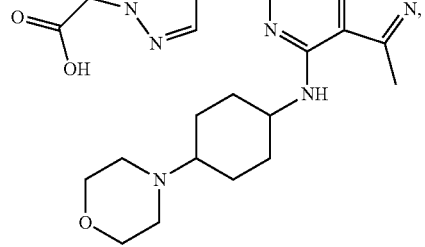

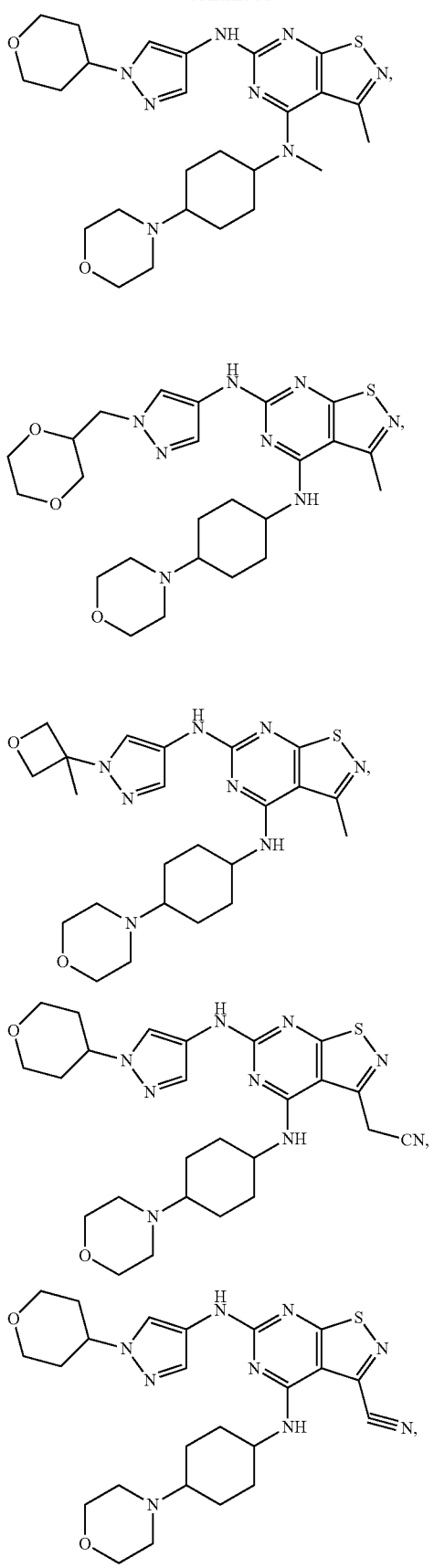
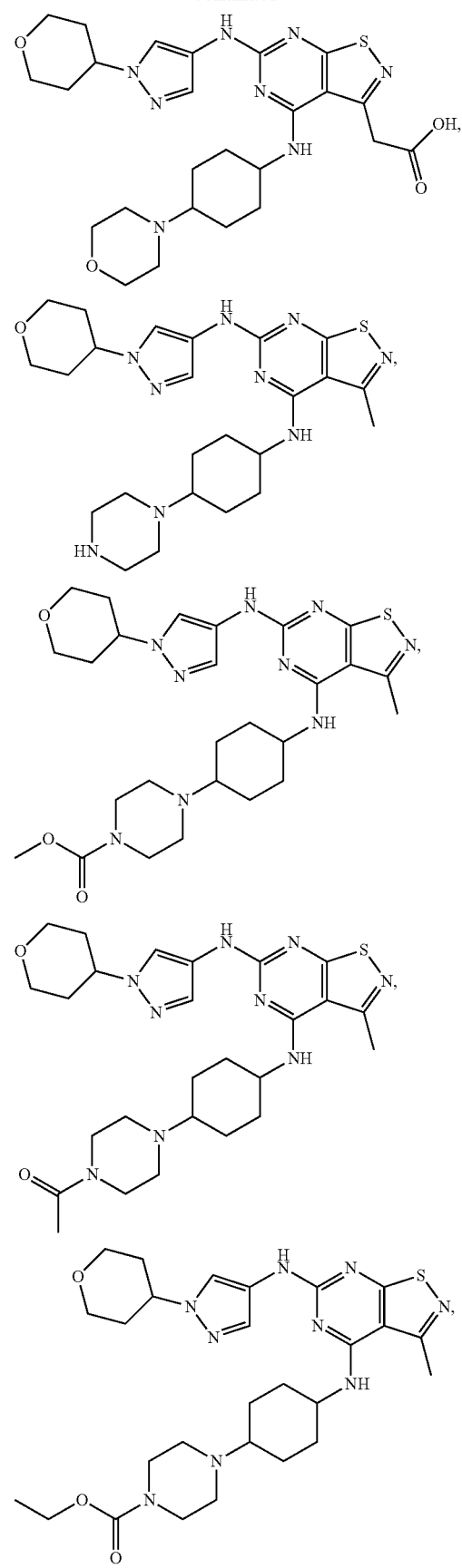

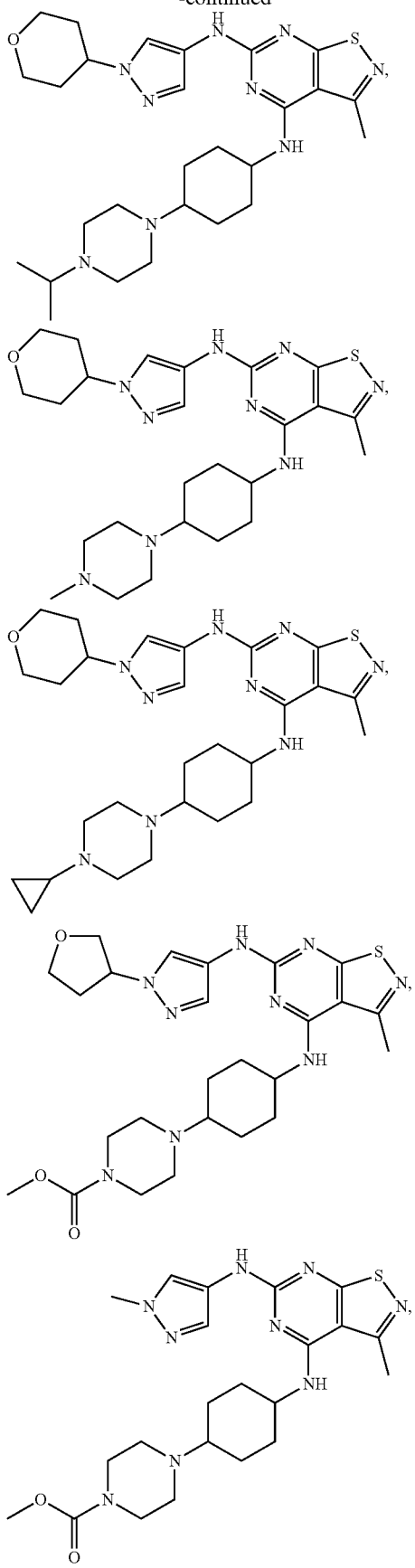
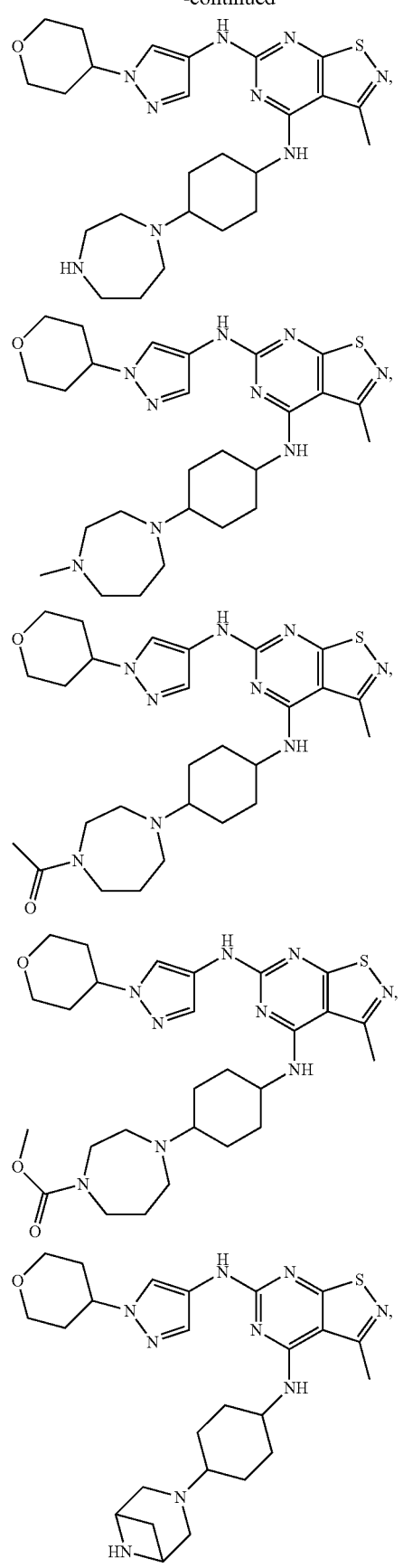

-continued
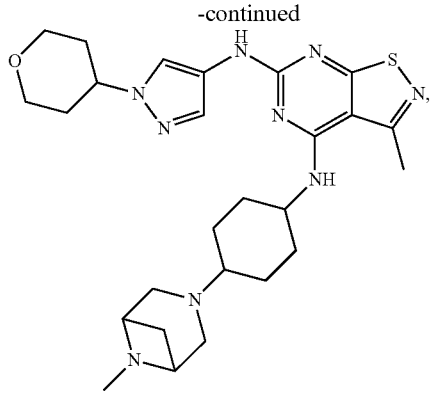
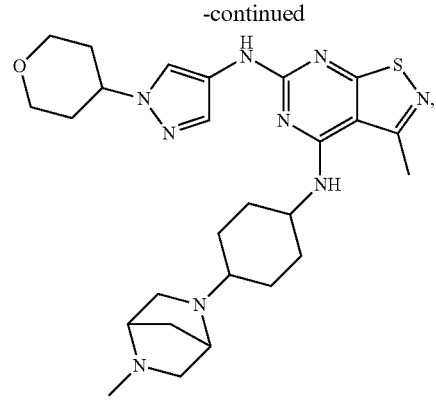
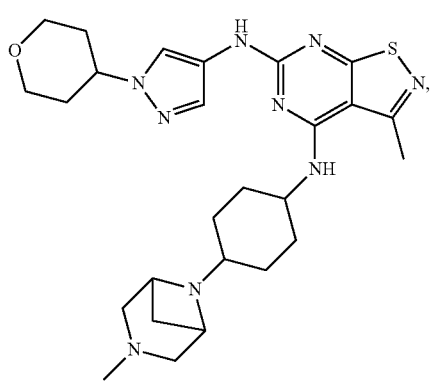
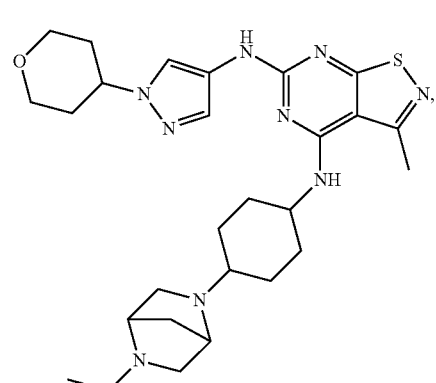
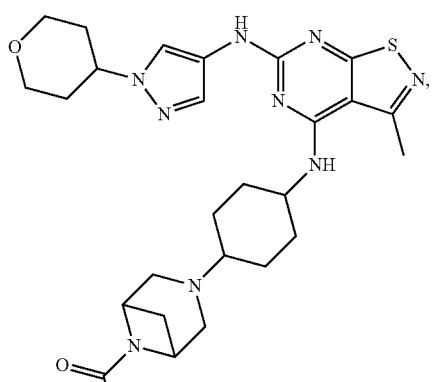
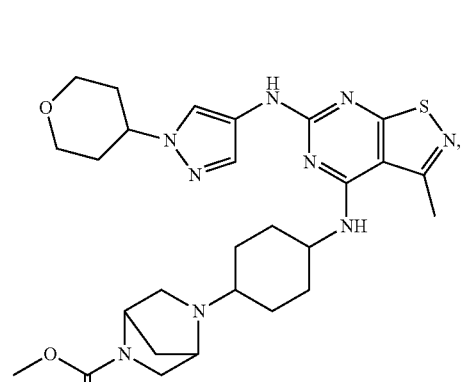
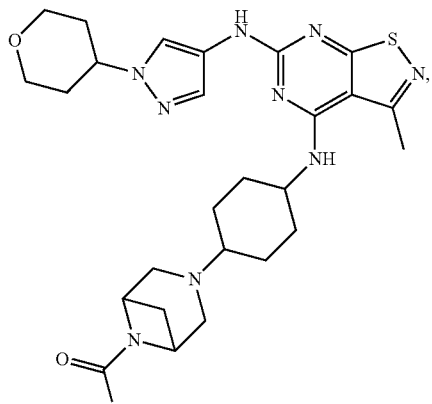
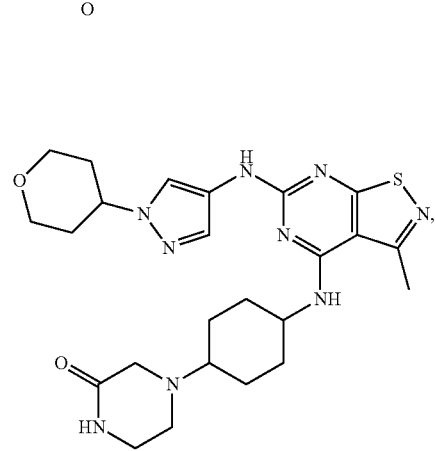

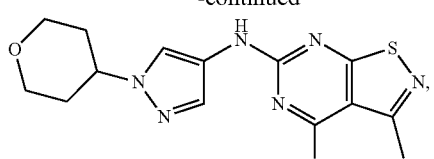
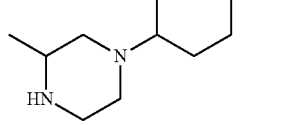
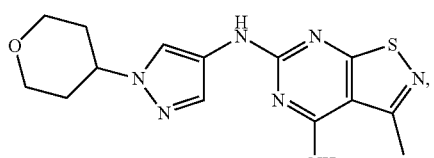
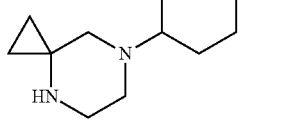
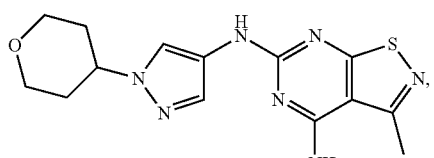
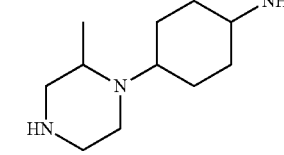
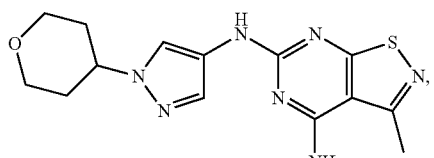
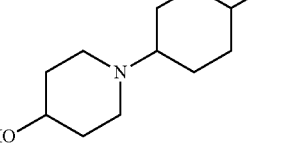
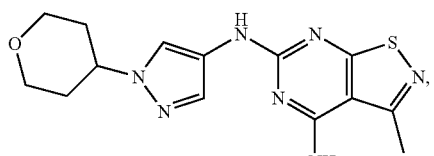
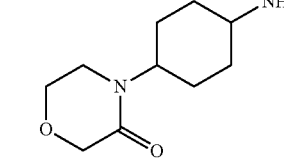
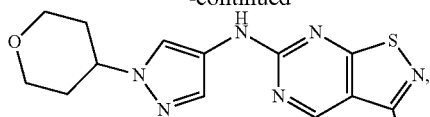
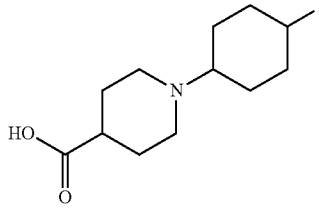
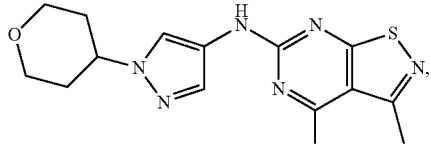
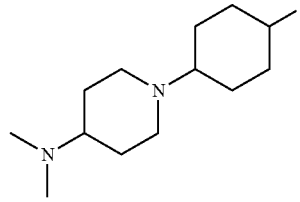
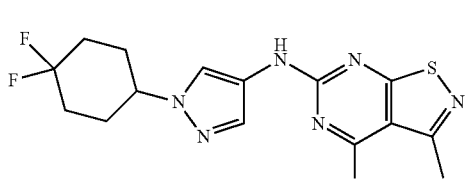
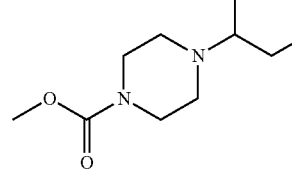
and
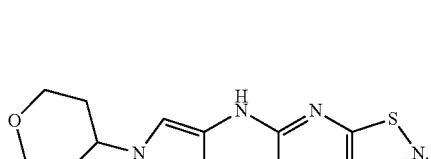
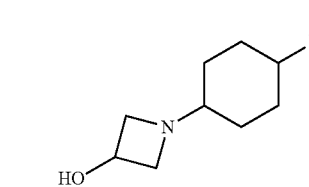
In some embodiments of the present invention, the compound above, its optical isomer or pharmaceutically acceptable salt thereof, is selected from the group consisting of 37
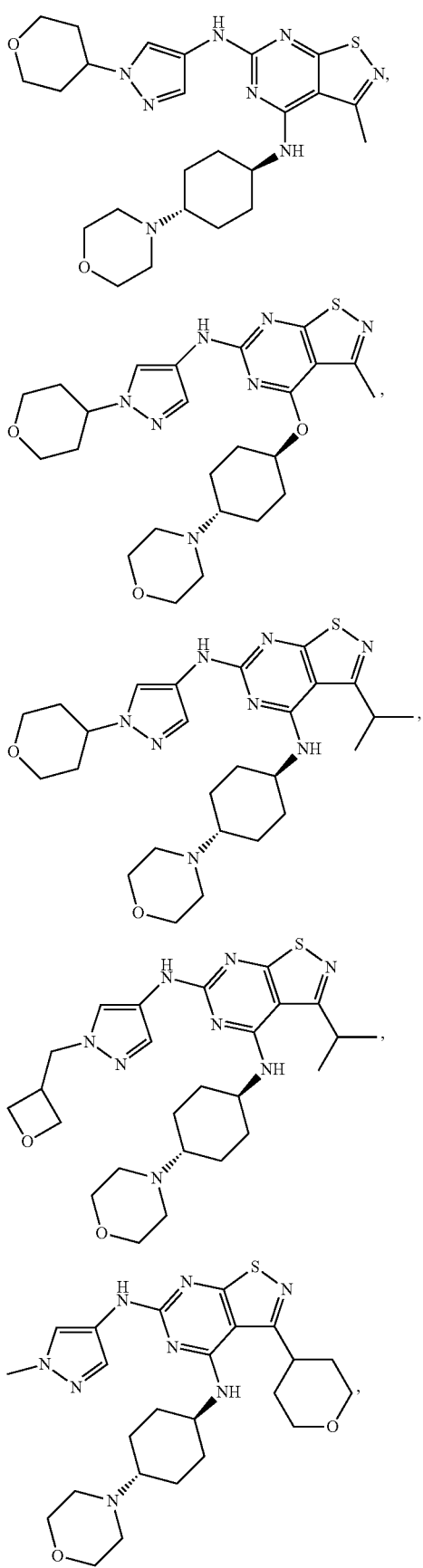
38
-continued
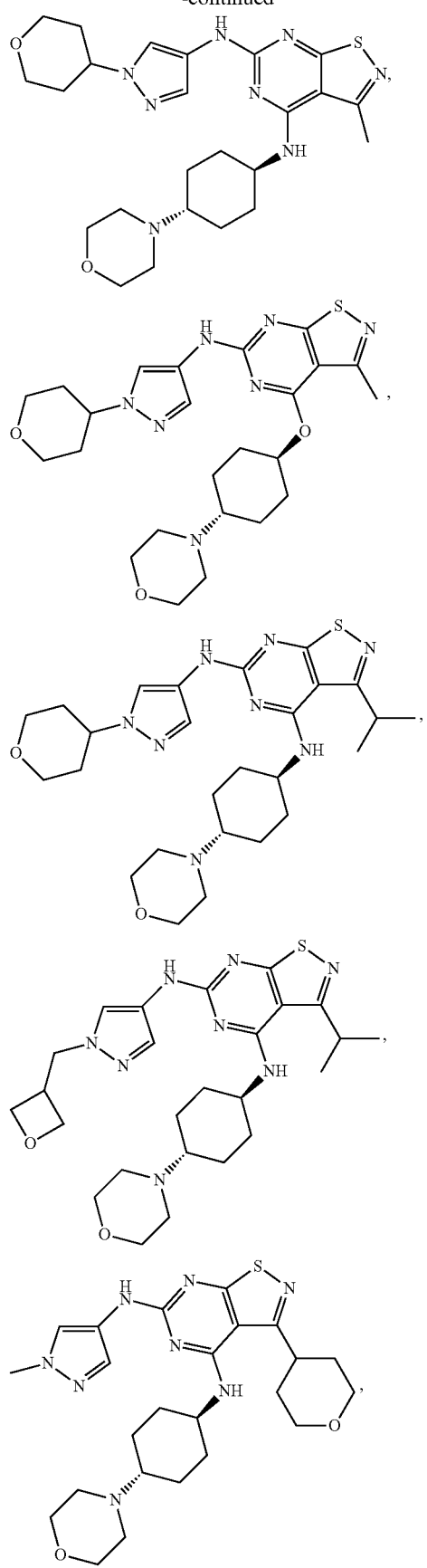

| 39 | 40 |
|---|---|
| -continued | -continued |
| 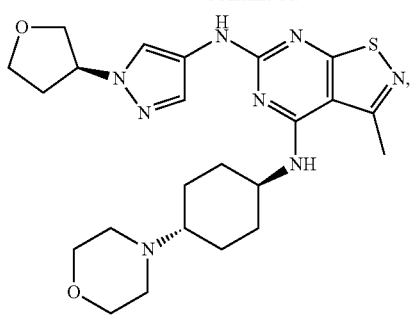 | 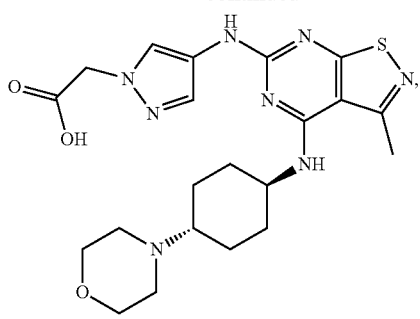 |
| 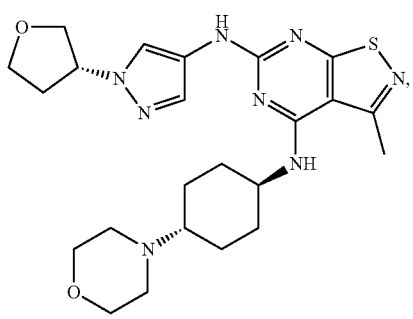 | 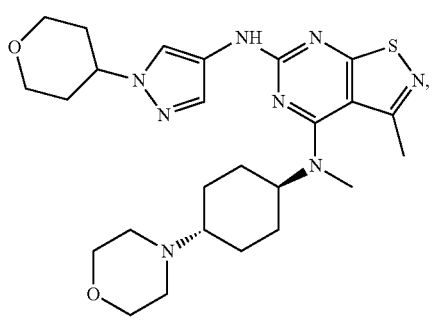 |
| 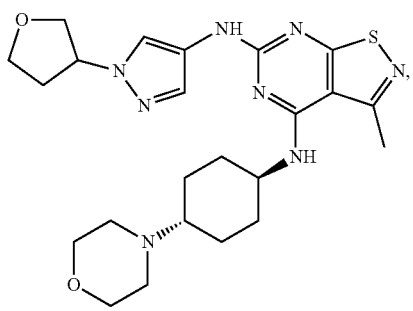 | 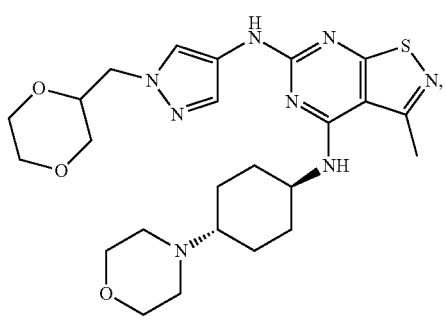 |
| 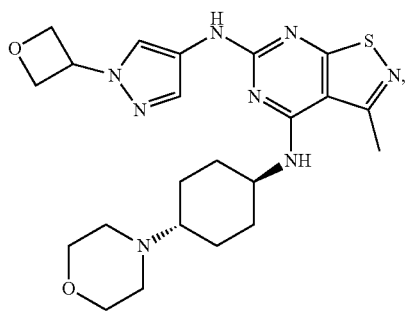 | 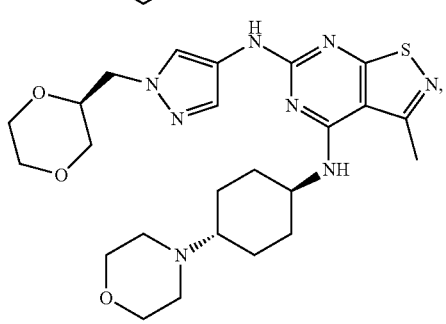 |
| 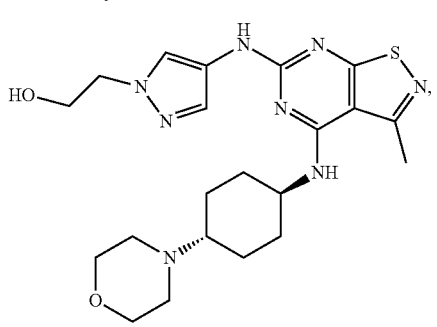 | 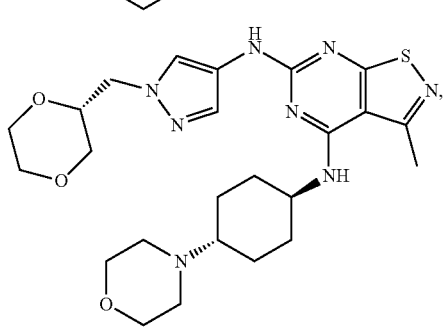 |

41
-continued
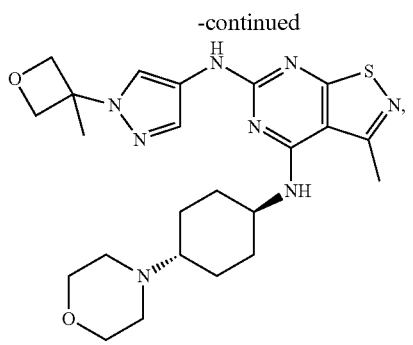
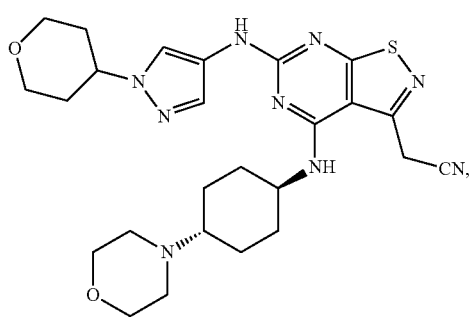
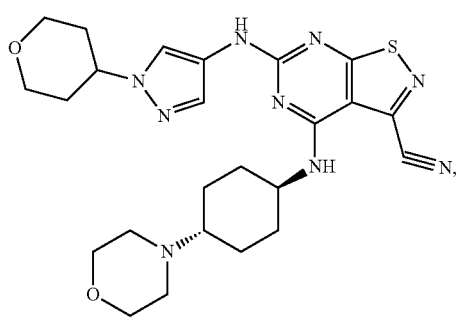
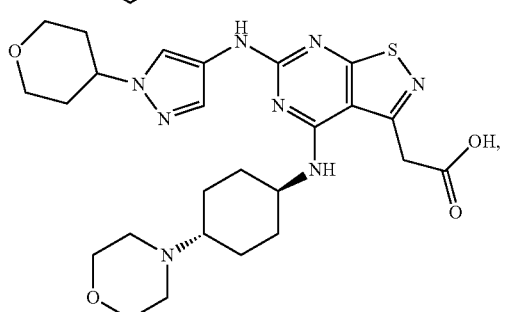
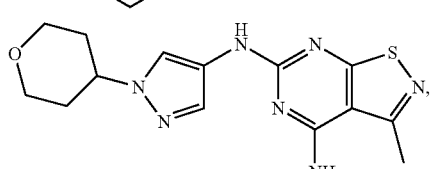
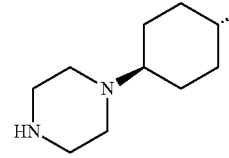
42
-continued
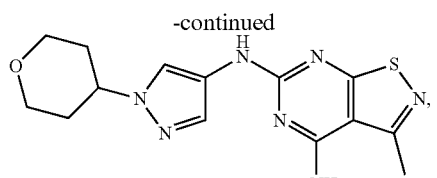
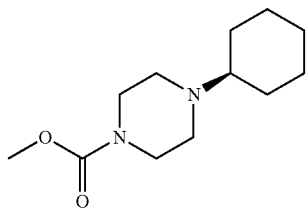
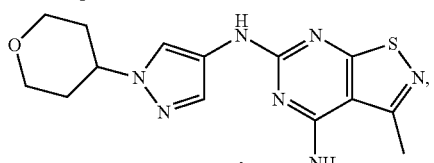
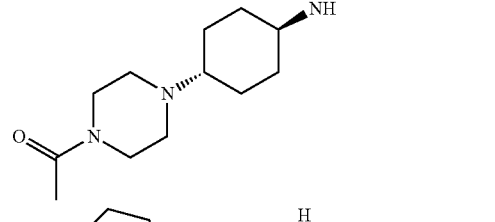
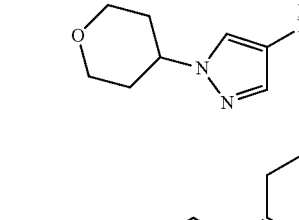
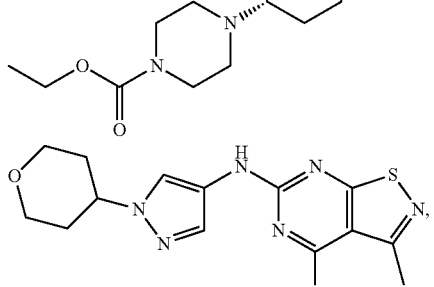
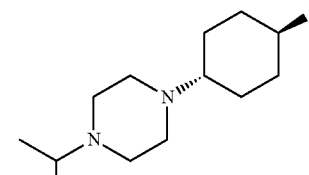
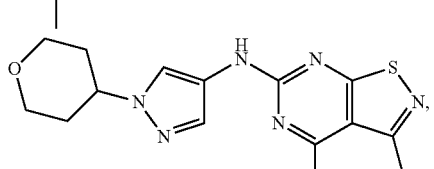
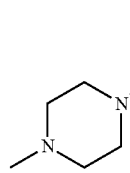

43
-continued
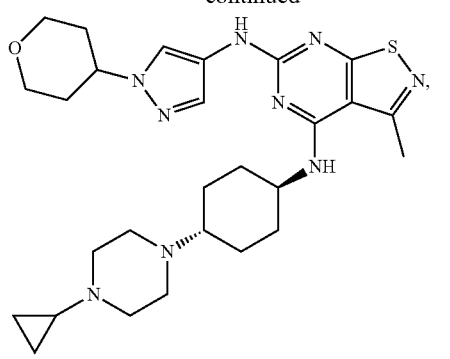
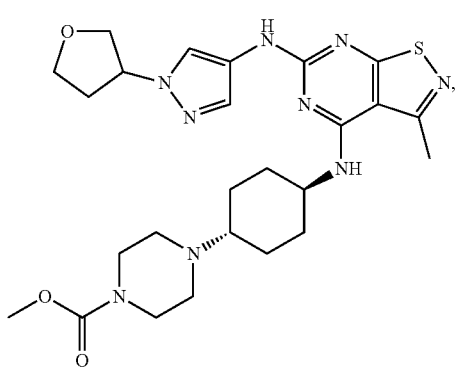
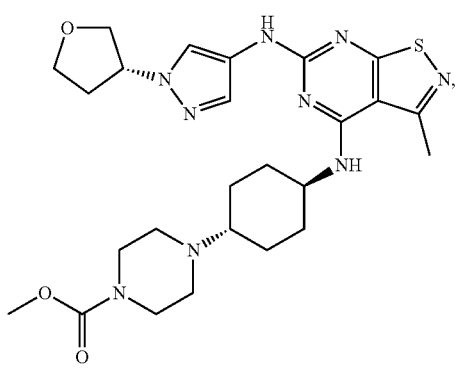
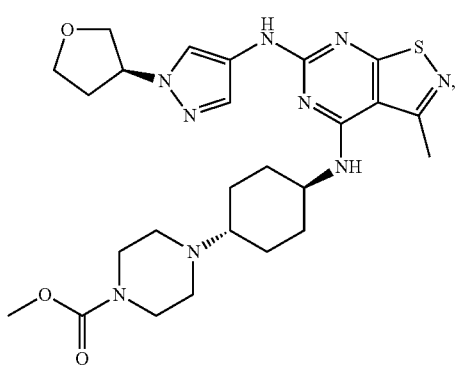
44
-continued
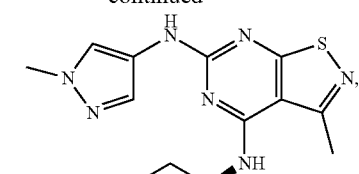
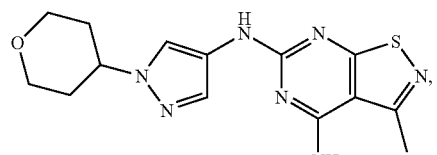
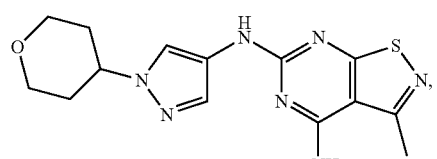
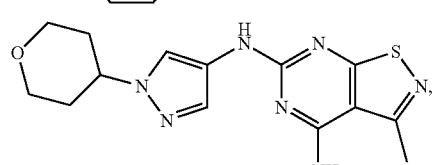
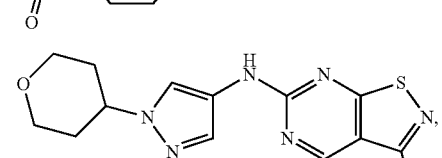
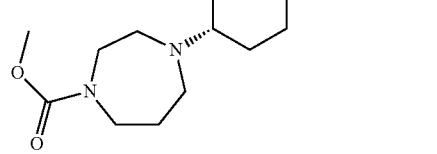

45
-continued
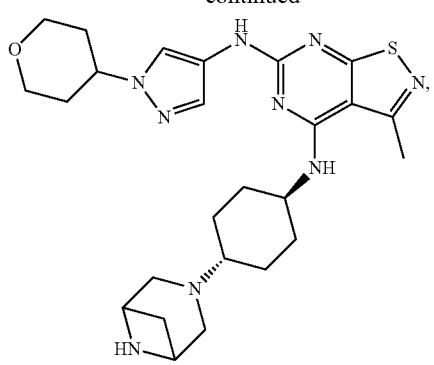
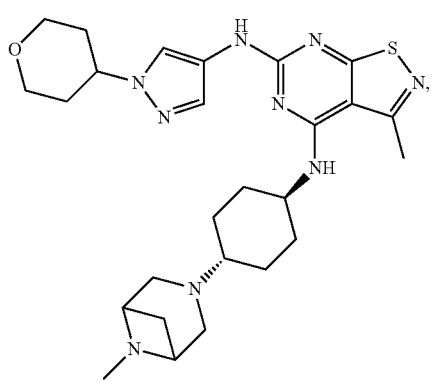
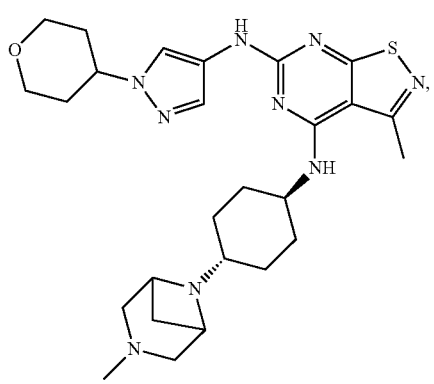
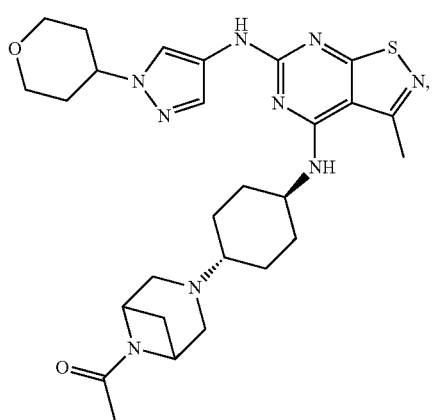
46
-continued
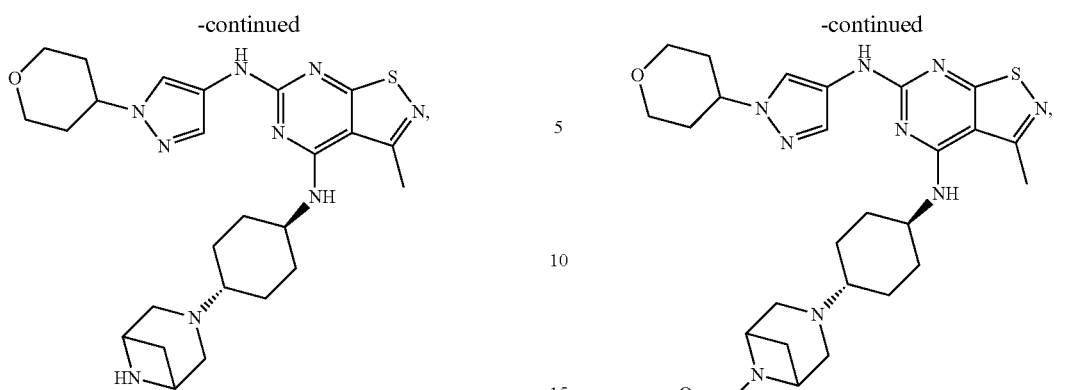
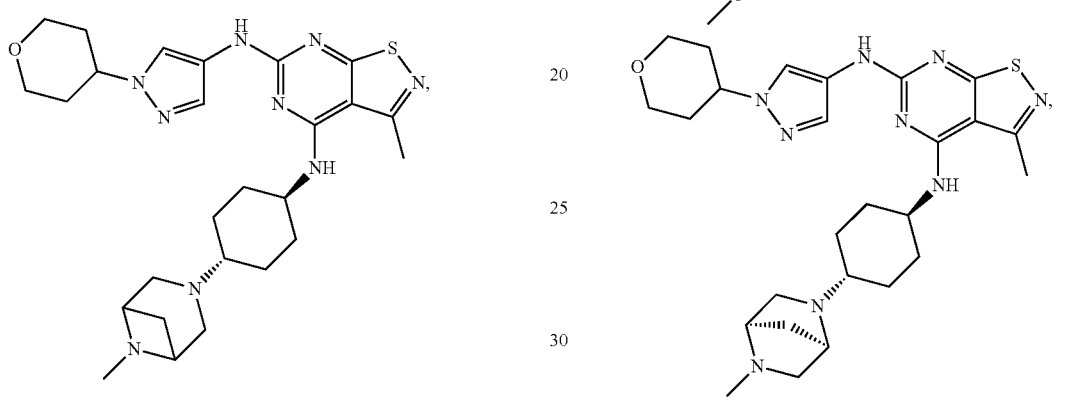
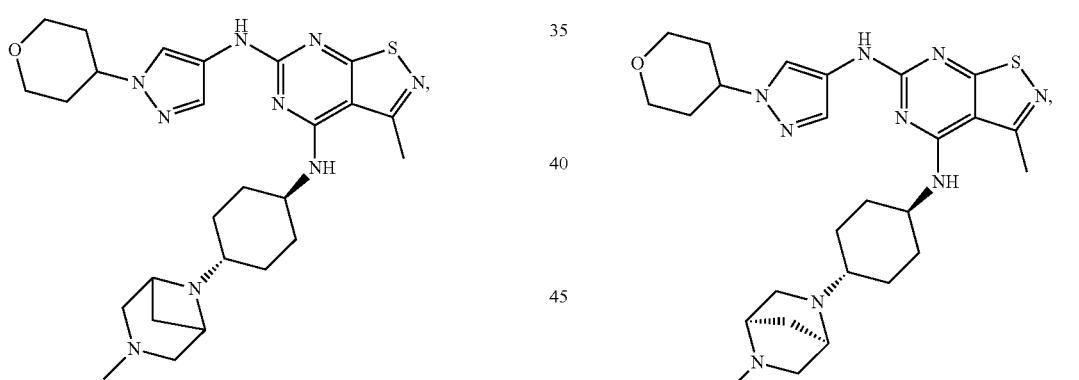
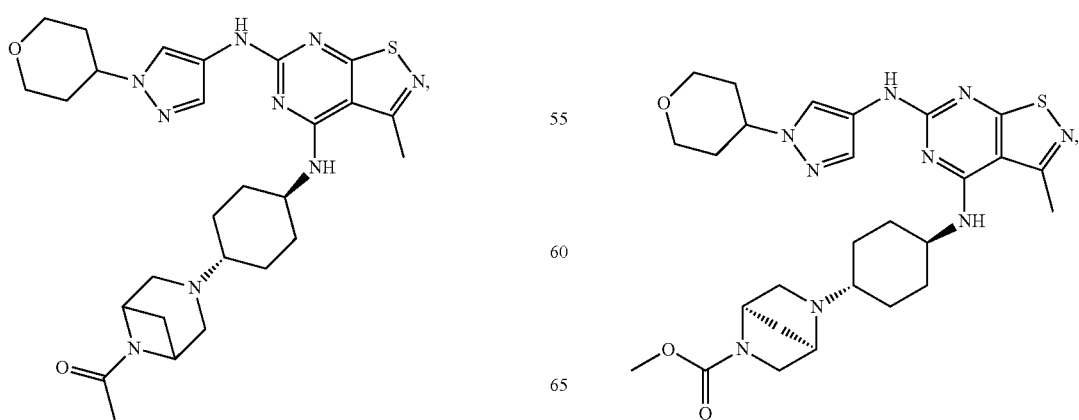

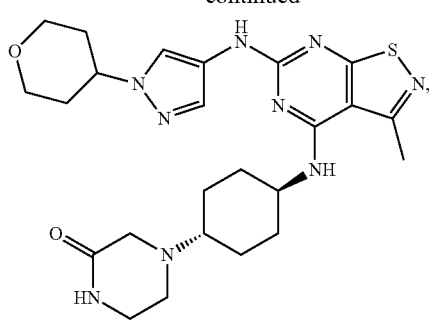
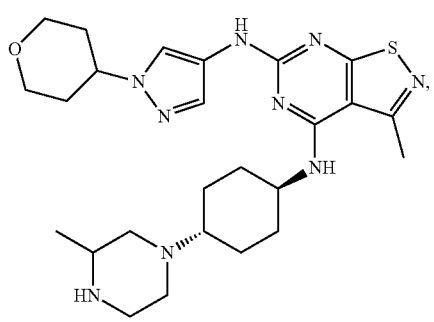
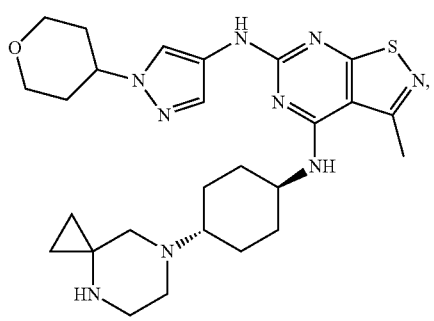
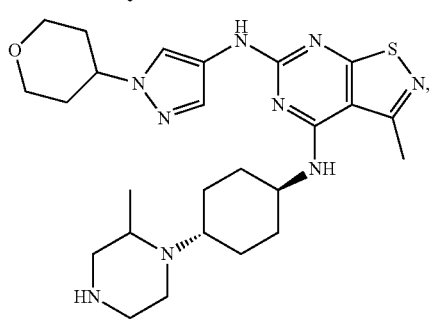
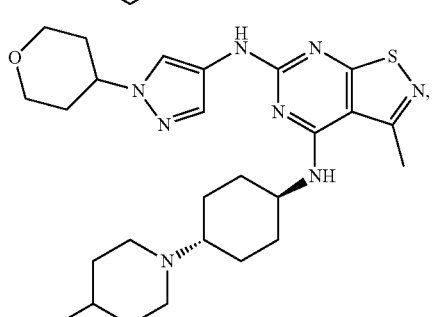
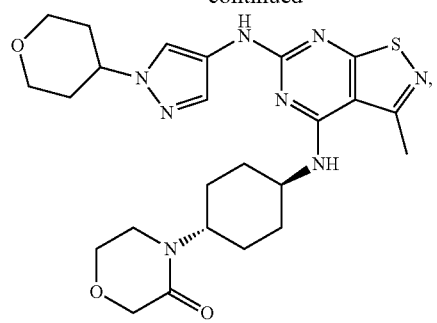
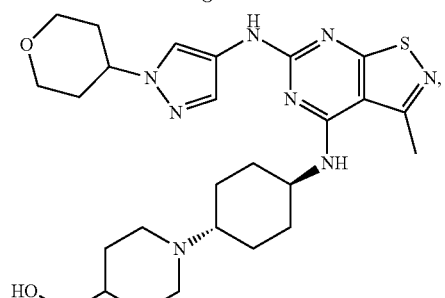
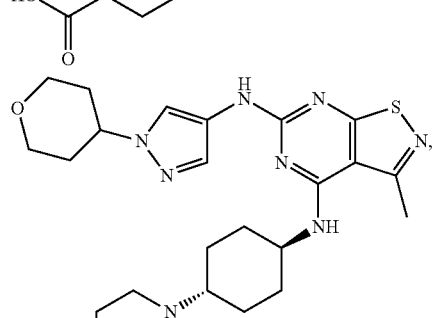
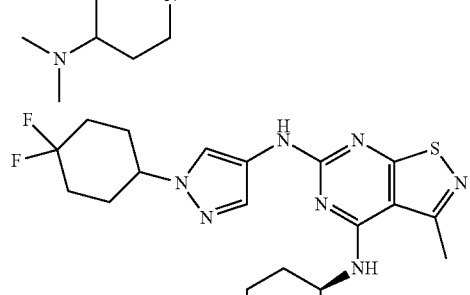
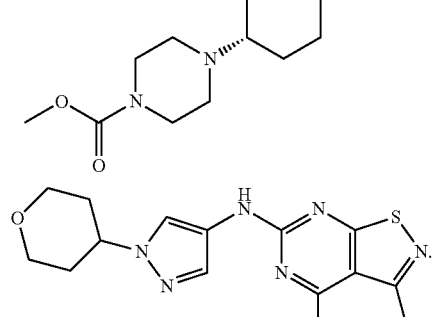
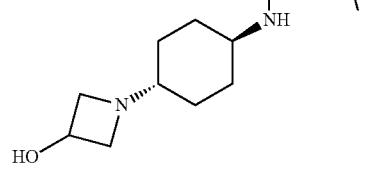

The present invention also provides a pharmaceutical composition, comprising a therapeutically effective amount of the compound above, its isomer or pharmaceutically acceptable salt thereof as an active ingredient, and pharmaceutically acceptable carriers.

The present invention also provides a method for treating IRAK4-related diseases in a mammal, comprising administering to the mammal, preferably a human, in need for such treatment a therapeutically effective amount of the compound above, its isomer or pharmaceutically acceptable salt thereof, or the pharmaceutical composition thereof.

The present invention also provides use of the compound above, its isomer or pharmaceutically acceptable salt thereof, or the pharmaceutical composition thereof, in preparing a medicament for treating an IRAK4-related diseases.

The present invention also provides use of the compound above, its isomer or pharmaceutically acceptable salt thereof, or the pharmaceutical composition thereof, in treating an IRAK4-related diseases. The present invention also provides the compound above, its isomer or pharmaceutically acceptable salt thereof, or the pharmaceutical composition thereof, for treating an IRAK4-related diseases.

The present invention also provides use of the compound above, its isomer or pharmaceutically acceptable salt thereof in preparing an IRAK4 inhibitor.

The present invention also provides use of the composition above in preparing an IRAK4 inhibitor.

Definitions

Unless otherwise stated, the following terms and phrases used herein are intended to have the following meanings. A particular term or phrase, unless otherwise specifically defined, should not be considered as indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be given by contacting the neutral form of such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be given by contacting the neutral form of such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid, phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid. Also included are salts of amino acids (e.g., arginine, etc.) and salts of organic acids such as glucuronic acid. Certain specific compounds disclosed herein contain both basic and acidic functional groups that allow the compounds to be converted into either base or acid addition salts.

The pharmaceutically acceptable salts disclosed herein can be synthesized from a parent compound having an acidic or basic group by conventional chemical methods. In general, such salts are prepared by the following method: the free acid or base form of the compound reacting with a stoichiometric amount of the appropriate base or acid in water or an organic solvent or a mixture thereof.

The compounds disclosed herein can be in the form of a geometric isomer or stereoisomer. All such compounds are contemplated herein, including cis and trans isomers, (−)- and (+)-enantiomers, (R)- and (S)-enantiomers, diastereomers, (D)-isomers, (L)-isomers, and racemic mixtures and other mixtures thereof, such as an enantiomer or diastereomer enriched mixture, all of which are encompassed within the scope of the present invention. The substituents such as alkyl may have an additional asymmetric carbon atom. All these isomers and mixtures thereof are encompassed within the scope of the present invention.

Unless otherwise stated, the term "enantiomer" or "optical isomer" refers to stereoisomers that are mirror images of each other.

Unless otherwise stated, the term "cis-trans isomer" or "geometric isomer" results from the inability of a double bond or a single bond of a cyclic carbon atom to freely rotate.

Unless otherwise stated, the term "diastereomer" or "diastereoisomer" refers to stereoisomers which have a molecule with two or more chiral centers and are in a non-mirror image relationship.

Unless otherwise stated, "(D)" or "(+)" stands for dextrorotation, "(L)" or "(−)" stands for levorotation, and "(DL)" or "(±)" stands for racemization.

Unless otherwise stated, the absolute configuration of a stereogenic center is represented by a wedged solid bond ( ⬛ ) and a wedged dashed bond ( ⬛ ), and the relative configuration of a stereogenic center is represented by a straight solid bond ( ⬛ ) and a straight dashed bond ( ⬛ ).

A wavy line ( ⬛ ) represents a wedged solid bond ( ⬛ ) or a wedged dashed bond ( ⬛ ), or a wavy line ( ⬛ ) represents a straight solid bond ( ⬛ ) and a straight dashed bond ( ⬛ ).

Optically active (R)- and (S)-isomers and D and L isomers can be prepared by chiral synthesis or chiral reagents or other conventional techniques. An enantiomer of certain compound disclosed herein can be prepared by asymmetric synthesis or derivatization using a chiral auxiliary, wherein the resulting diastereomeric mixture is separated and the auxiliary group is cleaved so as to provide the desired pure enantiomer. Alternatively, when the molecule contains a basic functional group (such as amino) or an acidic functional group (such as carboxyl), the compound reacts with an appropriate optically active acid or base to form a salt of the diastereoisomer, which is then subjected to diastereomeric resolution through conventional methods in the art to obtain the pure enantiomer. Furthermore, the enantiomer and the diastereomer are generally isolated through chromatography using a chiral stationary phase, optionally in combination with chemical derivatization (e.g., carbamate formation from amines). The compound disclosed herein may contain an unnatural proportion of atomic isotope at one or more of the atoms that constitute the compound. For example, the compound may be labeled with a radioisotope, such as tritium ($^3$H), iodine-125 ($^{125}$I), or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound described herein, whether radioactive or not, are encompassed within the scope of the present invention. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the compound after substitution is stable. When the substituent is oxygen (i.e., =O), it means that two hydrogen atoms are substituted. Substitution by oxygen does not occur on aromatic groups. The term "optionally substituted" means that an atom can be or cannot be substituted by a substituent. Unless otherwise specified, the type and number of the substituent may be arbitrary as long as being chemically achievable.

When any variable (e.g., R) occurs more than once in the constitution or structure of a compound, the definition of the variable in each case is independent. Thus, for example, if a group is substituted by 0-2 R, the group can be optionally substituted by two R at most, and the definition of R in each case is independent. Furthermore, a combination of the substituent and/or the variant thereof is permissible only if the combination can result in a stable compound.

When a variable is a single bond, it means that the two groups are directly linked, for example, in A-L-Z, when L represents a single bond, it means that the structure is actually A-Z.

For the listed linking groups, the direction for linking that is not indicated is arbitrary. For example, when the linking group L contained in

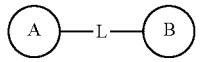

is -M-W—, -M-W— can either link ring A and ring B in a direction same as left-to-right reading order to form

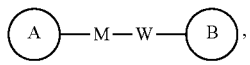, or link ring A and ring B in an opposing direction to form

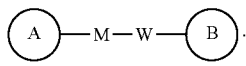.

A combination of the linking group, the substituent and/or the variant thereof is permissible only if the combination can result in a stable compound.

Unless otherwise specified, the number of atoms on a ring is generally defined as the number of ring members. For example, "3-6 membered ring" refers to a "ring" on which 3 to 6 atoms are arranged in a circle.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-3}$ alkyl" refers to a linear or branched saturated hydrocarbon group consisting of 1 to 3 carbon atoms. The $C_{1-3}$ alkyl includes, $C_{1-2}$ and $C_{2-3}$ alkyl, etc., and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like. Unless otherwise specified, "$C_{2-8}$ alkenyl" is used to denote a linear or branched hydrocarbon group containing 2 to 8 carbon atoms and at least one carbon-carbon double bond, which may be located anywhere in the group. The $C_{2-8}$ alkenyl includes $C_{2-6}$, $C_{2-4}$, $C_{2-3}$, $C_4$, $C_3$, and $C_2$ alkenyl etc., and may be monovalent, divalent or polyvalent. Examples of $C_{2-8}$ alkenyl include, but are not limited to, ethenyl, propenyl, butenyl, pentenyl, hexenyl, butadienyl, 1,3-pentadienyl, 1,3-hexadienyl, and the like.

Unless otherwise specified, the term "$C_{1-6}$ alkylamino" refers to an alkyl group containing 1 to 6 carbon atoms that is attached to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$, $C_2$ alkylamino and the like. Examples of $C_{1-6}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, and the like.

Unless otherwise specified, the term "$C_{1-3}$ alkylamino" refers to an alkyl group containing 1 to 3 carbon atoms that is attached to the rest of the molecule through an amino group. The $C_{1-3}$ alkylamino group includes $C_{1-2}$, $C_3$, $C_2$ alkylamino and the like. Examples of $C_{1-3}$ alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, and the like.

Unless otherwise specified, the term "3-10 membered heterocycloalkyl" used alone or in combination with other terms denotes a saturated cyclic group consisting of 3 to 10 ring atoms, 1, 2, 3 or 4 of which are heteroatoms independently selected from the group consisting of —O—, —S—, —NH—, N, and —C(=O)NH—, the remainder being carbon atoms. This includes monocyclic, bicyclic and tricyclic systems, wherein the bicyclic and tricyclic systems include spirocyclic, fused and bridged rings. Furthermore, with respect to the "3-10 membered heterocycloalkyl", a heteroatom may occupy the position where the heterocycloalkyl is attached to the rest of the molecule. The 3-10 membered heterocycloalkyl includes 3-9 membered, 3-8 membered, 3-7 membered, 3-6 membered, 3-5 membered, 4-6 membered, 5-6 membered, 4 membered, 5 membered, 6 membered heterocycloalkyl groups and the like. Examples of 3-10 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, or dioxepanyl, etc.

Unless otherwise specified, the term "3-6 membered heterocycloalkyl" used alone or in combination with other terms denotes a saturated cyclic group consisting of 3 to 6 ring atoms, 1, 2, 3 or 4 of which are heteroatoms independently selected from the group consisting of —O—, —S—, —NH— and N, the remainder being carbon atoms. This includes monocyclic and bicyclic systems, wherein the bicyclic system includes spirocyclic, fused, and bridged rings. Furthermore, with respect to the "3-6 membered heterocycloalkyl", a heteroatom may occupy the position where the heterocycloalkyl is attached to the rest of the molecule. The 3-6 membered heterocycloalkyl includes 4-6 membered, 5-6 membered, 4 membered, 5 membered, 6 membered heterocycloalkyl, and the like. Examples of 3-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc.

Unless otherwise specified, "$C_{3-8}$ cycloalkyl" refers to a saturated cyclic hydrocarbon group consisting of 3 to 8 carbon atoms. This includes monocyclic and bicyclic systems, wherein the bicyclic system includes spirocyclic, fused and bridged rings. The $C_{3-8}$ cycloalkyl includes $C_{3-6}$, $C_{3-5}$, $C_{4-8}$, $C_{4-6}$, $C_{4-5}$, $C_{5-8}$, $C_{5-6}$ cycloalkyl, or the like, and may be monovalent, divalent, or polyvalent. Examples of $C_{3-8}$ cycloalkyl include, but are not limited to, cyclopropyl, cyclobutyl, and the like.

Unless otherwise specified, "$C_{4-6}$ cycloalkyl" denotes a saturated cyclic hydrocarbon group consisting of 4 to 6 carbon atoms, including monocyclic and bicyclic systems. The $C_{4-6}$ cycloalkyl includes $C_{4-5}$, $C_{5-6}$ cycloalkyl, and the like, and may be monovalent, divalent or polyvalent. Examples of $C_{4-6}$ cycloalkyl include, but are not limited to, cyclobutyl, cyclopentyl, cyclohexyl, and the like.

Unless otherwise specified, $C_{n-n+m}$ or $C_n$-$C_{n+m}$ includes any one of the specific cases of n to n+m carbons, e.g., $C_{1-6}$ includes $C_1$, $C_2$, $C_3$, $C_4$, $C_5$ and $C_6$, and also includes any one of the ranges within n to n+m, e.g., $C_{1-6}$ includes $C_{1-2}$, $C_{1-3}$, $C_{1-4}$, $C_{2-3}$, $C_{2-4}$ and $C_{3-5}$, etc.; similarly, n membered to n+m membered means n to n+m atoms in a ring, for example, 3-6 membered rings include 3 membered rings, 4 membered rings, 5 membered rings, 6 membered rings, and includes any ranges within n to n+m, for example, 3-6 membered rings include 3-5 membered rings, 3-6 membered rings, 4-6 membered rings, 4-5 membered rings, and 5-6 membered rings, etc.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

The solvent used in the present invention can be commercially available. The following abbreviations are used in the present invention: aq for water; HATU for O-(7-azabenzotriazol-1-yl)-N,N,N',N'-tetramethyluronium hexafluorophosphate; EDC for N-(3-dimethylaminopropyl)-N'-ethylcarbodiimide hydrochloride; m-CPBA for 3-chloroperoxybenzoic acid; eq for equivalent; CDI for carbonyldiimidazole; DCM for dichloromethane; PE for petroleum ether; DIAD for diisopropyl azodicarboxylate; DMF for N,N-dimethylformamide; DMSO for dimethyl sulfoxide; EtOAc for ethyl acetate; EtOH for ethanol; MeOH for methanol; CBz for benzyloxycarbonyl, an amine protecting group; BOC for t-butoxycarbonyl, an amine protecting group; HOAc for acetic acid; $NaCNBH_3$ for sodium cyanoborohydride; r.t. for room temperature; O/N for overnight; THF for tetrahydrofuran; $Boc_2O$ for di-tert-butyl dicarbonate; TFA for trifluoroacetic acid; DIPEA for diisopropylethylamine; $SOCl_2$ for thionyl chloride; $CS_2$ for carbon disulphide; TsOH for p-toluenesulfonic acid; NFSI for N-fluoro-N-(phenylsulfonyl)benzenesulfonamide; NCS for 1-chloropyrrolidine-2,5-dione; n-$Bu_4NF$ for tetrabutylammonium fluoride; iPrOH for 2-propanol; mp for melting point; and LDA for lithium diisopropylamide.

Compounds are named according to conventional nomenclature rules in the art or using ChemDraw® software, and supplier's catalog names are given for commercially available compounds.

Technical Effects

By the present invention, a series of fused ring compounds with higher activity, improved metabolic stability, better druggability, and favorable pharmacokinetic properties are acquired.

The compounds disclosed herein generally exhibit better inhibitory activity against IRAK4. The representative compounds disclosed herein have impressive advantages over the reference compound (WXR1) in terms of liver microsome stability in multiple species, and particularly in some species (e.g., mice), have an up to 20-fold superiority in clearance. The compounds disclosed herein generally exhibit better inhibitory activity on proliferation of THP-1 cells. The total systemic exposure, peak concentration and bioavailability of various compounds of this project orally administered were equivalent or superior to those of the reference compound WXR2 (ND-2110) at the same dose, demonstrating superior pharmacokinetic properties. At the same doses, oral WX001 in SD rats exhibited significant inhibitory effect on lipo-polychollagen (LPS)-induced TNF-α secretion, which was significantly superior to the reference compounds WXR2(ND-2110), WXR3(BAY-1830839) and WXR4 (BAY-1834845). In this experiment, the efficacy of WX001 was equivalent to that of dexamethasone DEX. At the same doses, oral compounds WX001 WX026 and WX044 in SD rats exhibited significant inhibitory effect on lipo-polychollagen (LPS)-induced TNF-α secretion. In this experiment, the efficacy of WX026 was equivalent to that of dexamethasone DEX.

DETAILED DESCRIPTION

Figure 1:
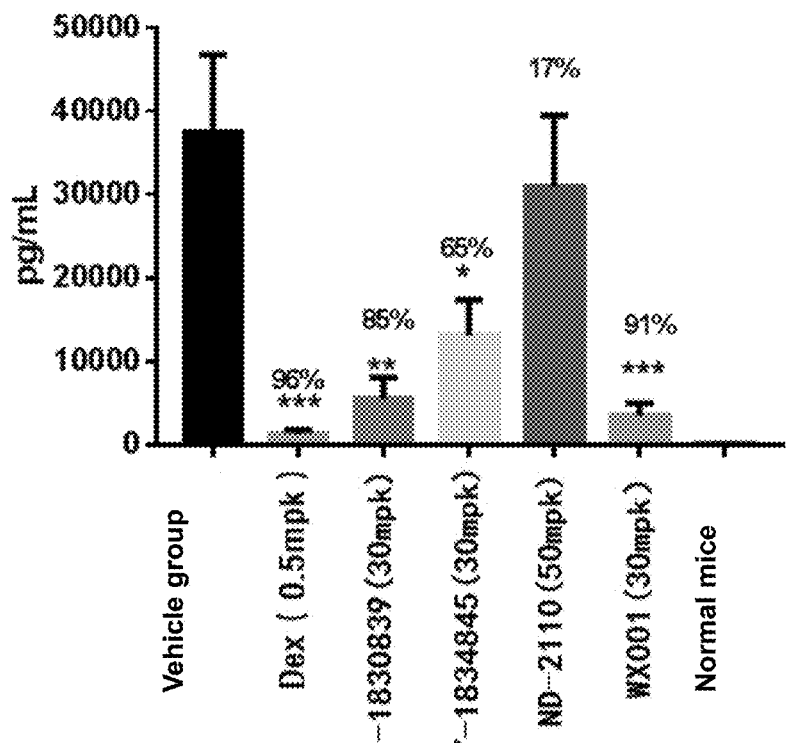
FIG. 1 shows the results of a pharmacodynamic study evaluating lipo-polycollagen (LPS)-induced TNF-α secretion in SD rats with the dose of the compounds being 30 mpk.

The present invention is described in detail below by way of examples. However, this is by no means disadvantageously limiting the scope of the present invention. Although the present invention has been described in detail herein and specific examples have also been disclosed, it will be apparent to those skilled in the art that various changes and modifications can be made to the specific examples without departing from the spirit and scope of the present invention.

Intermediate A1

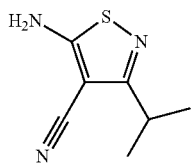

Synthetic route:

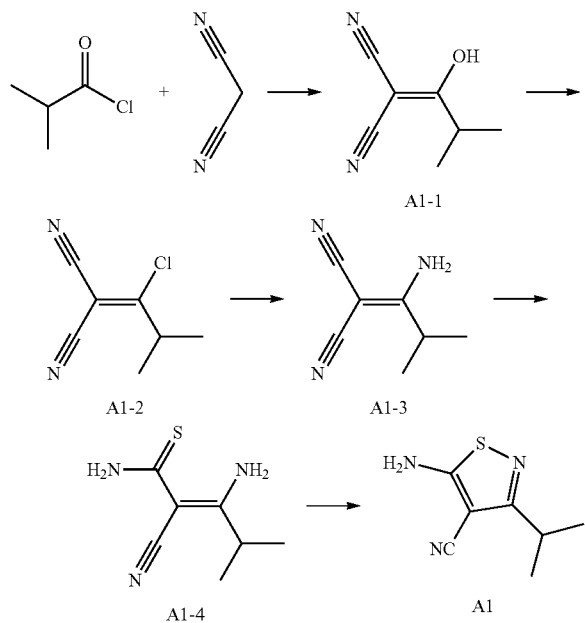

Step 1: Synthesis of Compound A1-1

Malononitrile (52.70 g) was dissolved in acetonitrile (1 L) in a 3-L single-neck flask, and was added with triethylamine (161.45 g). The mixture was well mixed, slowly added with isobutyryl chloride (85 g), and incubated at 50° C. for 2 hours. Then acyl chloride was added, and the system was exothermic and turned from a colorless clear solution to a yellow-green suspension. After the reaction was completed, the solvent was removed by a rotary evaporator. The residue was dissolved in water (100 mL) and added with ethyl acetate (30 mL) for three extractions. The organic phases were combined and dried using a rotary evaporator to give product A1-1. $^1$H NMR (400 MHz, CDCl$_3$) δ=1.23 (d, J=10.4 Hz, 6H), 3.16 (sept, J=10.4 Hz, 1H).

Step 2: Synthesis of Compound A1-2

A1-1 (1.1 g) was dissolved in dichloromethane (15 mL) in a 100-mL reaction flask, added with phosphorus oxychloride (2.26 g) dropwise at 0° C., and incubated at 20° C. for 16 hours. After the reaction was completed, the mixture was directly added to water, and the organic phase was separated. The aqueous phase was then extracted twice with dichloromethane (10 mL), and the organic phases were combined and dried using a rotary evaporator to give compound A1-2. $^1$H NMR (400 MHz, CDCl$_3$) δ=1.7 (d, J=10.4 Hz, 6H), 3.09 (sept, J=10.4 Hz, 1H).

Step 3: Synthesis of Compound A1-3

A1-2 (10 g) and aqueous ammonia (7.56 g) were added in a 250-mL reaction flask and incubated at 20° C. for 1 hour. Precipitation was observed and the reaction system was directly added with water (10 mL), with ethyl acetate (10 mL) for three extractions. The organic phases were combined, dried with rotary evaporator to give compound A1-3. $^1$H NMR (400 MHz, CDCl$_3$) δ=1.24 (d, J=10.4 Hz, 6H), 3.15 (sept, J=10.4 Hz, 1H).

Step 4: Synthesis of Compound A1-4

A1-3 (1 g) and triethylamine (2.08 g) were dissolved in pyridine (10 mL) in a 100-mL three-neck flask, and then added with hydrogen sulfide and incubated at 30° C. for 0.5 hour. After the reaction was completed, the mixture was dried using a rotary evaporator, and the residue was added with water and then with dichloromethane (10 mL) for two extractions. The solvent was removed using a rotary evaporator to give a yellow oily substance, which was then purified by column chromatography (eluent: dichloromethane) to give product A1-4. $^1$H NMR (400 MHz, CDCl$_3$) δ=1.20 (d, J=10.4 Hz, 6H), 3.15 (s, J=10.4 Hz, 1H), 6.04 (br, 1H), 6.55 (br, 1H), 6.87 (br, 1H), 12.18 (br, 1H).

Step 5: Synthesis of Compound A1

To a 250 mL single-neck flask with a magnetic stirrer were added compound A1-4 and MeOH (80 mL), and H$_2$O$_2$ (8.87 g) was added dropwise to the mixture. The reaction system was then stirred at 10-20° C. for 16 h. After the reaction was completed, most of the solvent was removed by concentration under reduced pressure to give a solid residue. Ethyl acetate (40 mL) was added to dissolve the solid, followed by saturated aqueous sodium sulfite solution (30 mL). The mixture was stirred at room temperature for 30 minutes, and phases were separated. The aqueous phase was extracted with ethyl acetate (20 mL×3). The combined organic phases were dehydrated using anhydrous sodium sulfate and filtered, and the filtrate was concentrated under reduced pressure to give product A1. $^1$H NMR (400 MHz, CDCl$_3$) δ=5.38 (br s, 2H), 3.13 (td, J=6.8, 13.8 Hz, 1H), 1.33 (d, J=6.8 Hz, 6H).

Intermediate A2

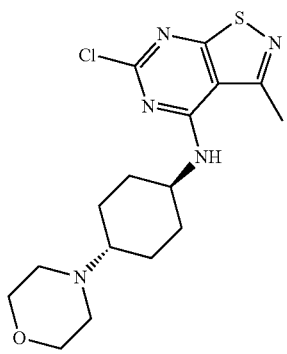 [SMILES: Cc1nsc2nc(Cl)nc(N[C@H]3CC[C@H](N4CCOCC4)CC3)c12]

Synthetic route:

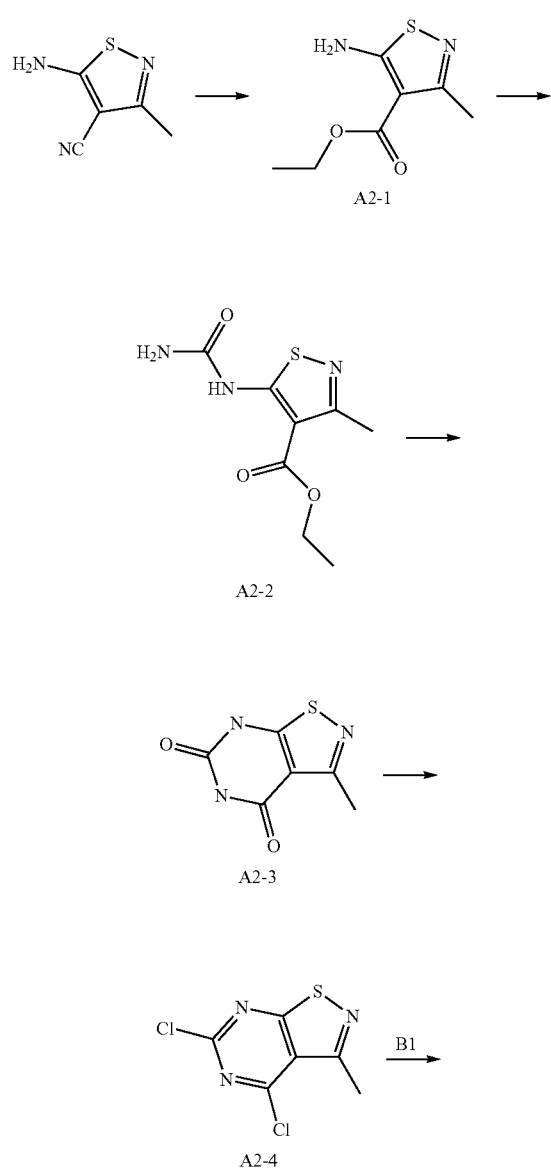

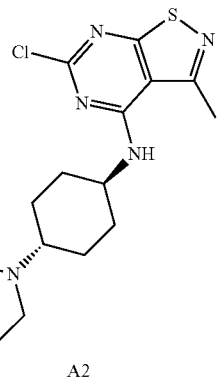

A2

Step 1: Synthesis of Compound A2-1

To a 100-mL round-bottom single-neck flask with a magnetic stirrer were added 5-amino-3-methylisothiazole-4-carbonitrile (1.00 g) and absolute ethanol (25 mL). Concentrated sulfuric acid (7.05 g) was slowly added to the reaction system at 20° C. The reaction flask was stirred and incubated in an oil bath at 100° C. for 16 hours. After the reaction was completed, the reaction system was cooled to room temperature, and was slowly added to 100 mL of sodium bicarbonate solution. The mixture was adjusted to pH 8, added with ethyl acetate (30 mL) for three extractions, dehydrated using anhydrous sodium sulfate, and filtered, and the filtrate was concentrated under reduced pressure to give a yellow crude product. The crude product was separated and purified by column chromatography (SiO$_2$, petroleum ether:ethyl acetate=10:1-3:1, v/v) to give compound A2-1. $^1$H NMR (400 MHz, CDCl$_3$) δ=6.49 (br s, 2H), 4.35 (q, J=7.2 Hz, 2H), 2.53 (s, 3H), 1.40 (t, J=7.0 Hz, 3H).

Step 2: Synthesis of Compound A2-2

A solution of A2-1 (2.5 g) in dry dichloromethane (25 mL) was added to a 50-mL single-neck flask with a magnetic stirrer in nitrogen atmosphere, cooled to −60° C., and chlorosulfonic isocyanate (1.79 g) was added dropwise to the reaction. Then the reaction solution was slowly warmed to 25° C. and stirred for 30 minutes, until the solution became clear. The reaction mixture was concentrated under reduced pressure to give a yellow solid, which was suspended with water (10 mL), and the suspension was stirred at 75° C. for 30 minutes, filtered and dried to give compound A2-2.

Step 3: Synthesis of Compound A2-3

To a solution of A2-2 (1.7 g) in n-butanol (20 mL) in a 50-mL single-neck flask with a magnetic stirrer potassium carbonate (3.07 g) was added in N2 atmosphere, and the mixture was incubated at 130° C. for 16 hours. The solvent was removed using a rotary evaporator. The residue was slurried with 10 mL of water, filtered and dried to give compound A2-3. LCMS (ESI) m/z: 183.8[M+H]+, $^1$H NMR (400 MHz, DMSO-d$_6$) δ=9.43 (br s, 2H), 2.39-2.34 (m, 3H).

Step 4: Synthesis of Compound A2-4

Phosphorus oxychloride (2.93 g) was added to a solution of dimethylaniline (330.75 mg) and A2-3 (0.5 g) in toluene (5 mL) in a 100-mL sealed tube and the mixture was incubated at 120° C. for 16 hours. The reaction system was added slowly to 30 mL of water, and extracted with dichloromethane (20 mL×3). The organic phases were combined, dehydrated using anhydrous sodium sulfate, filtered and concentrated to give a crude product. The crude product was chromatographed to give compound A2-4. LCMS (ESI) m/z: 219.8[M+H]+.

Step 5: Synthesis of Compound A2

A2-4 (0.2 g), intermediate B1 (303.85 mg) and sodium carbonate (385.28 mg) were dissolved in acetonitrile (4 mL) in a 50-mL single-neck flask with a magnetic stirrer. The reaction system was incubated and stirred at 80° C. for 16 hours. The reaction system was cooled to room temperature, and concentrated under reduced pressure to give a residue. To the residue were added dichloromethane (10 mL) and water (10 mL) for redissolving. The aqueous phase was extracted with dichloromethane (5 mL). The combined organic phases were washed with saturated brine, dehydrated using anhydrous sodium sulfate and filtered. The filtrate was concentrated under reduced pressure to give a pale yellow solid. The solid was slurried using PE/EtOAc=10:1 (10 mL), stirred for 1 hour and filtered to give compound A2. LCMS (ESI) m/z: 368.1[M+H]+.

Intermediate A3

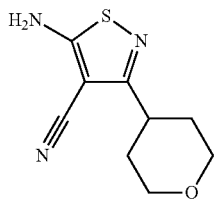 [SMILES: N#Cc1c(C2CCOCC2)nsc1N]

Synthesis of intermediate A3 was similar to that of A1, except that the starting material isobutyryl chloride in step 1 was replaced by tetrahydropyran-4-carbonyl chloride.

1H NMR (400 MHz, DMSO-d6) δ=8.16-7.89 (m, 2H), 3.99-3.80 (m, 2H), 3.40 (dt, J=3.9, 10.9 Hz, 2H), 2.99-2.84 (m, 1H), 1.82-1.60 (m, 4H).

Intermediate A4

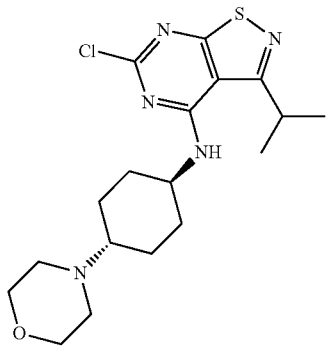 [SMILES: CC(C)c1nsc2nc(Cl)nc(N[C@H]3CC[C@H](N4CCOCC4)CC3)c12]

Synthesis of intermediate A4 starting with A1 was similar to the synthesis of A2, except that the starting material 5-amino-3-methylisothiazole-4-carbonitrile in step 1 was replaced by A1.

LCMS (ESI) m/z: 396.2, 398.2 [M+H]+.

1H NMR (400 MHz, CHLOROFORM-d) δ=5.52 (br d, J=7.6 Hz, 1H), 4.31-4.19 (m, 1H), 4.16-4.09 (m, 1H), 4.16-4.09 (m, 1H), 3.79-3.70 (m, 4H), 3.22-3.13 (m, 1H), 2.65-2.56 (m, 4H), 2.41-2.27 (m, 3H), 2.06- 1.96 (m, 2H), 1.60-1.48 (m, 2H), 1.46 (d, J=6.8 Hz, 4H), 1.39-1.29 (m, 2H).

Intermediate A5

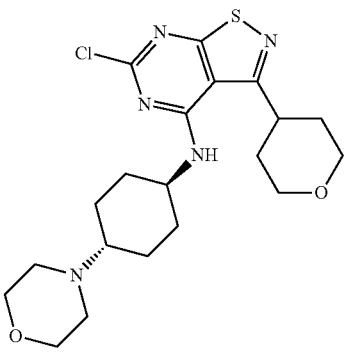 [SMILES: Clc1nc(N[C@H]2CC[C@H](N3CCOCC3)CC2)c2c(C3CCOCC3)nsc2n1]

Synthesis of intermediate A5 starting with A3 was similar to the synthesis of A2, except that the starting material 5-amino-3-methylisothiazole-4-carbonitrile in step one was replaced by A3.

LCMS (ESI) m/z: 438.2, 440.2 [M+H]+

Intermediate A6

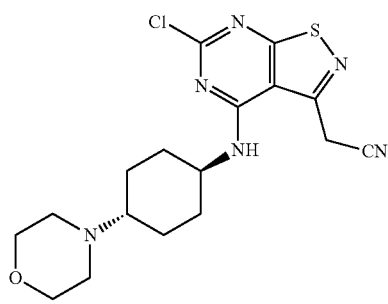 [SMILES: N#CCc1nsc2nc(Cl)nc(N[C@H]3CC[C@H](N4CCOCC4)CC3)c12]

Synthetic route:

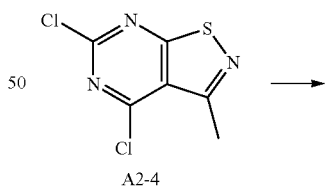

A2-4

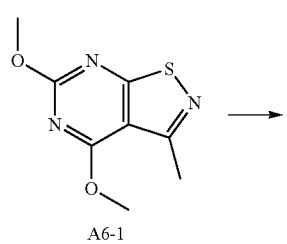

A6-1

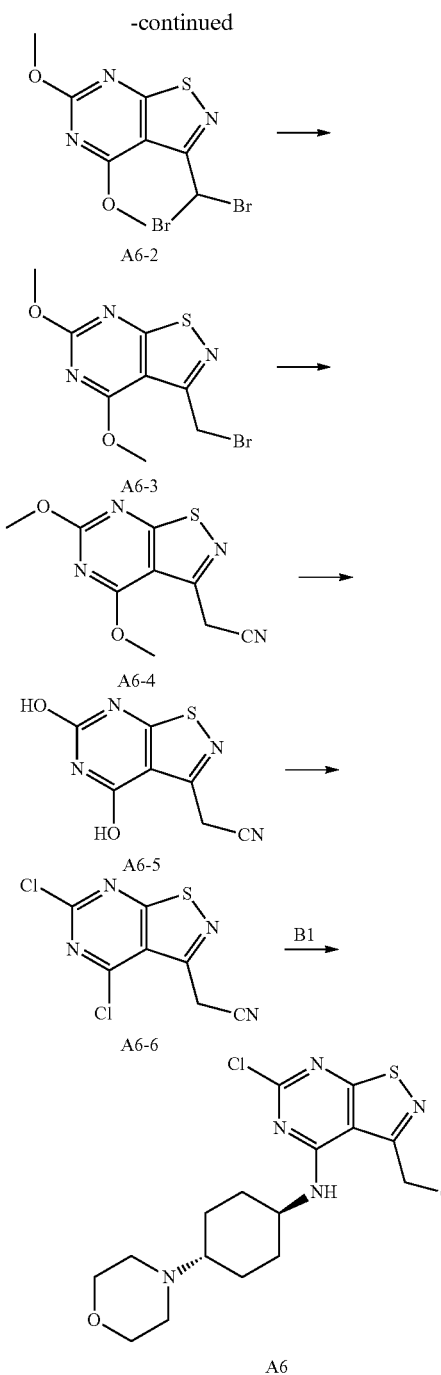

zoyl peroxide (453.58 mg) in a flask. After three nitrogen purges, the mixture was incubated at 80° C. for 12 hours and was added into saturated aqueous sodium thiosulfate (200 mL), and the phases were separated. The aqueous phase was extracted with dichloromethane (50 mL×2), and the combined organic phases were dried, filtered, and concentrated under reduced pressure. The crude product was purified by column chromatograph (ISCO® for crude products; 80 g column; eluent: 0-60% ethyl acetate/petroleum ether)) to give compound A6-2.

Step 3: Synthesis of Compound A6-3

A6-2 (4 g) was dissolved in acetonitrile (20 mL), added with diethyl phosphite (1.95 g) and N,N-diisopropylethylamine (2.80 g) and the mixture was incubated at 25° C. for 3 hours. The reaction solution was concentrated under reduced pressure, and the crude product was purified by column chromatograph (ISCO® for crude products; 80 g column; eluent: 0-60% ethyl acetate/petroleum ether)) to give compound A6-3.

Step 4: Synthesis of Compound A6-4

A6-3 (1.5 g) was dissolved in acetonitrile (40 mL) in a flask, and was sequentially added with trimethylsilyl cyanide (564.20 mg) and potassium carbonate (786.00 mg). The mixture was stirred at 10° C. for 12 hours. The reaction system was added into 200 mL of saturated aqueous ammonium chloride, and extracted with ethyl acetate (200 mL×2). The organic phases were combined, dehydrated using anhydrous sodium sulfate, filtered and concentrated under reduced pressure. The resulting crude product was purified on a silica gel column (eluent: dichloromethane:ethyl acetate=100:0-10:1) to give compound A6-4. LCMS (ESI) m/z: 237.1 [M+H]. $^1$H NMR (400 MHz, CDCl$_3$) δ=4.22 (s, 3H), 4.21 (s, 2H), 4.13 (s, 3H).

Step 5: Synthesis of Compound A6-5

A6-4 (0.5 g) was mixed with N,N-dimethylformamide (10 mL) and then pyridine hydrochloride (1.22 g) in a flask, and the mixture was purged with nitrogen three times. The mixture was stirred at 100° C. for 12 hours. The solvent was completely removed under reduced pressure. The residue was slurried with 10 mL of dichloromethane and the mixture was filtered. The filter cake was dried under reduced pressure to give compound A6-5. LCMS (ESI) m/z: 209.1 [M+H].

Step 6: Synthesis of Compound A6-6

Synthesis of intermediate A6-6 starting with A6-5 was similar to the step four of A2 synthesis, except that the starting material A2-3 in step 4 was replaced with A6-5.

Step 7: Synthesis of Compound A6

Synthesis of intermediate A6 starting with A6-6 was similar to the fifth step of A2 synthesis, except that starting material A2-4 in step 5 was replaced with A6-6.

Intermediate A7

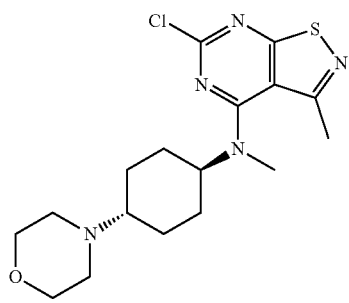 [SMILES: Cc1nsc2nc(Cl)nc(N(C)[C@H]3CC[C@H](N4CCOCC4)CC3)c12]

Step 1: Synthesis of Compound A6-1

A2-4 (10 g) was dissolved in methanol (200 mL) and added with a solution of sodium methoxide in methanol (5 M, 36.35 mL). The mixture was incubated at 68° C. for 12 hours, and then added into a saturated ammonium chloride solution (500 mL) and extracted with ethyl acetate (150 mL). The organic phase was dehydrated, filtered, and concentrated under reduced pressure. The crude product was purified by column chromatograph (ISCO®; 80 g column; eluent: 0-50% ethyl acetate/petroleum ether; flow rate: 40 mL/min) to give a compound A6-1.

Step 2: Synthesis of Compound A6-2

Compound A6-1 (8.79 g) was mixed with 1,2-dichloroethane (100 mL), N-bromosuccinimide (26.66 g) and ben-

Synthetic route

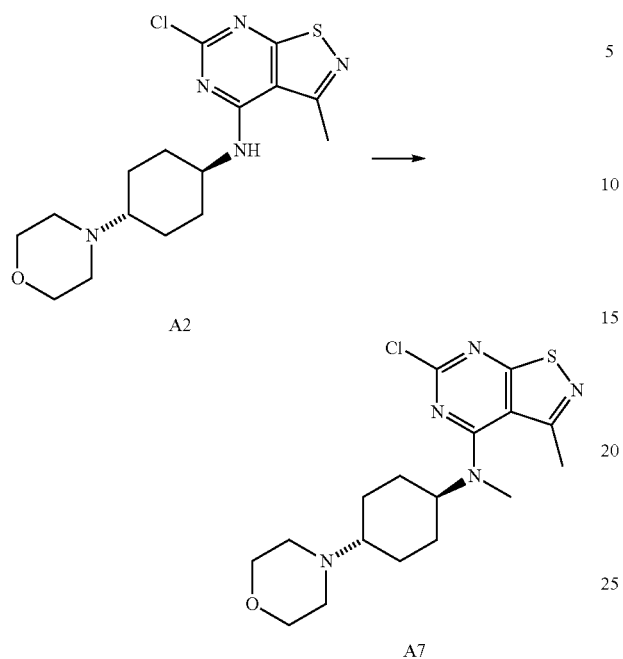

Compound A2 (0.3 g) was added to N,N-dimethylformamide (3 mL), and the mixture was cooled to 0° C. before sodium hydride (48.93 mg, purity: 60%) was added. The mixture was stirred for 0.5 hour, before iodomethane (150.47 mg) was added. The mixture was then warmed to 15° C., followed by 2.5 hours of stirring. The resulting solution was added into water (80 mL) and extracted with ethyl acetate (90 mL×2). The organic phases were combined and washed with saturated brine (40 mL×3). Then the organic phase was dehydrated using anhydrous sodium sulfate, and filtered to remove the desiccant. The filtrate was subjected to vacuum evaporation to give compound A7. LCMS (ESI) m/z: 382 [M+H]+.

Intermediates in the table below are commercially available reagents.

| Number | Structure | CAS |
|---|---|---|
| B1 | | 412356-24-2 |
| B2 | | 1190380-49-4 |
| B3 | | 1063734-49-5 |
| B4 | 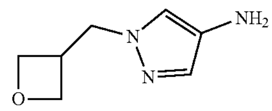 [SMILES: Nc1cnn(CC2COC2)c1] | 118280755 |
| B5 | 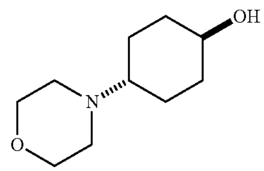 [SMILES: O[C@H]1CC[C@H](N2CCOCC2)CC1] | 1228947-14-5 |
| B15 | 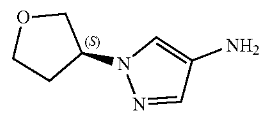 | 1258558-35-8 |
| B16 | 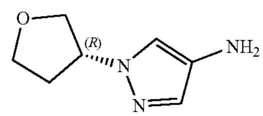 | 1258558-36-9 |
| B17 | 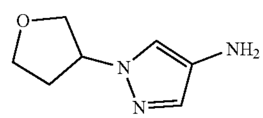 [SMILES: Nc1cnn(C2CCOC2)c1] | 1311369-72-8 |
| B18 | 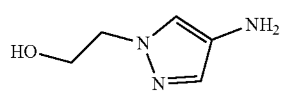 | 948571-47-9 |
| B19 | 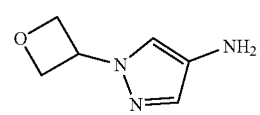 | 1338719-26-8 |

Intermediate B20

Synthetic route:

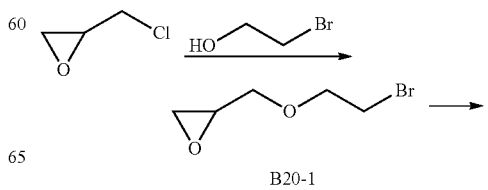

B20-1

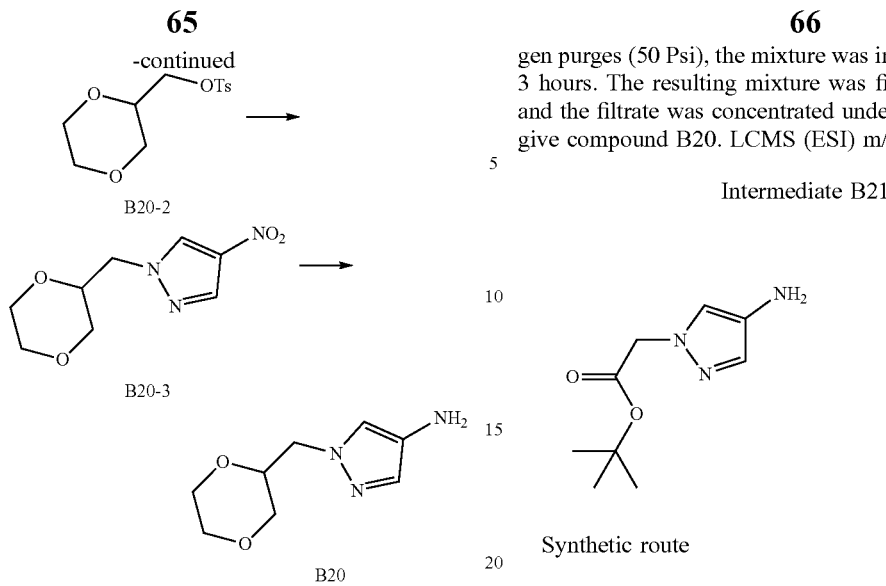

Step 1: Synthesis of Compound B20-1

2-bromoethanol (40.52 g) and boron trifluoride diethyl etherate (1.53 g) was added to toluene (80 mL). The mixture was heated to 70° C., added with epichlorohydrin (20 g) dropwise, and incubated at 70° C. for 1 hour. The reaction system was cooled to 10° C. Aqueous sodium hydroxide (21.61 g, 100 mL) was slowly added dropwise, before the mixture was incubated at 25° C. for 12 hours. The phases were separated. The aqueous phase was extracted with 2-methyltetrahydrofuran (20 mL×3), and the organic phases were combined. The combined organic phases were washed with water (100 mL), dehydrated, filtered and concentrated under reduced pressure to give compound B20-1.

Step 2: Synthesis of Compound B20-2

Aqueous sodium hydroxide (21.61 g, 150 mL) was added with compound B20-1 (29.52 g) and incubated at 90° C. for 1 hour before cooling to 15° C. Then a solution of p-toluensulfonyl chloride (41.21 g) in anhydrous tetrahydrofuran (150 mL) was dropwise added, and the mixture was incubated at 25° C. for 12 hours. Phases were separated. The aqueous phase was extracted with 2-methyltetrahydrofuran (100 mL×2), and the resulting organic phases were combined and added with 4 g of dimethylaminopyridine and 30 mL of triethylamine before 10 minutes of stirring. Saturated aqueous ammonium chloride (200 mL) was added and the organic phase was separated and concentrated to give a crude product, which was then subjected column chromatograph (ISCO®; 220 g column; eluent: 0-80% ethyl acetate/petroleum ether; flow rate: 60 mL/min) to give compound B20-2.

Step 3: Synthesis of Compound B20-3

Compound B20-2 (2 g, 7.34 mmol, 1 eq), 4-nitropyrrole (1.25 g) and cesium carbonate (4.79 g) were added to N,N-dimethylformamide (20 mL) and the mixture was incubated at 70° C. for 2 hours. The resulting solution was added into water (100 mL) and extracted with ethyl acetate (180 mL). The resulting organic phase was dehydrate using anhydrous sodium sulfate, filtered and concentrated under reduced pressure. The crude product was purified on a silica gel column (petroleum ether:ethyl acetate=100:0 to 4:1) to give compound B20-3. LCMS (ESI) m/z: 214.0 [M+H]$^+$

Step 4: Synthesis of Compound B20

Wet palladium on carbon (1 g, 10%) was added with methanol (5 mL) and B20-3 (1.5 g) sequentially in a hydrogenation flask in argon atmosphere. After three hydrogen purges (50 Psi), the mixture was incubated at 30° C. for 3 hours. The resulting mixture was filtered through celite, and the filtrate was concentrated under reduced pressure to give compound B20. LCMS (ESI) m/z: 184.1 [M+H]$^+$

Intermediate B21

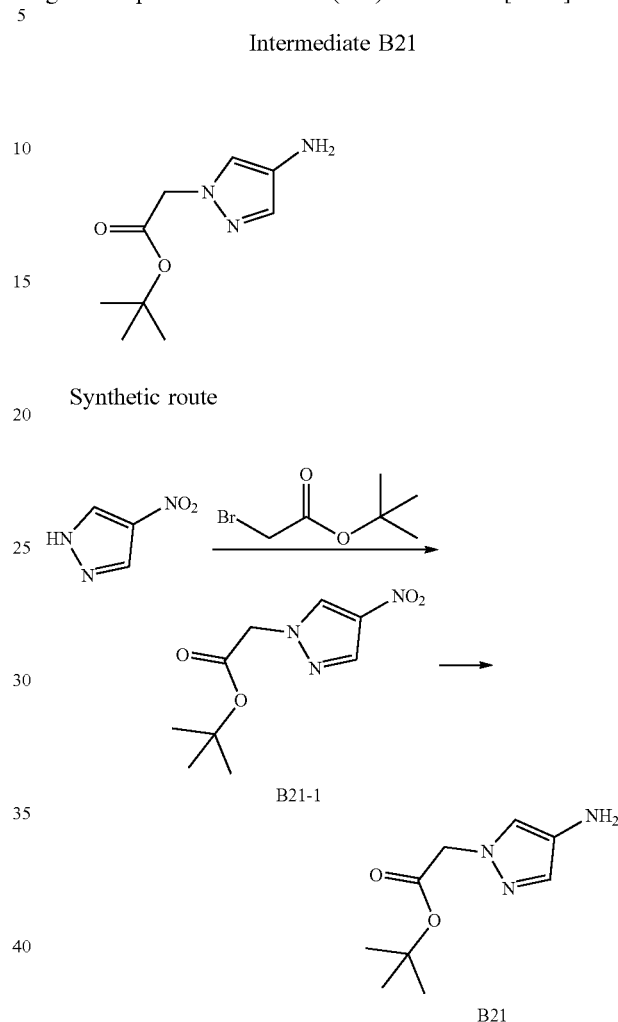

Synthetic route

Step 1: Synthesis of Compound B21-1

4-Nitropyrrole (10 g) and tert-butyl bromoacetate (17.25 g) were added to a reactor containing acetonitrile (100 mL), and potassium carbonate (14.67 g) was then added. The mixture was stirred at 80° C. for 5 hours. The reaction system was added into 100 mL of saturated aqueous ammonium chloride, and extracted with ethyl acetate (200 mL×2). The organic phases were combined, dehydrated using anhydrous sodium sulfate, filtered and concentrated under reduced pressure. The crude product was purified by column chromatograph (ISCO®; 220 g column; eluent: 0-60% ethyl acetate/petroleum ether; flow rate: 80 mL/min) to give compound B21-1.

Step 2: Synthesis of Compound B21

In argon atmosphere, wet palladium on carbon (3 g, 10%) was added with methanol (50 mL) in a hydrogenation flask, and then mixed with B21-1 (10 g), followed by three hydrogen purges (50 psi). The mixture was stirred at 25° C. for 3 hours. The resulting solution was filtered through celite. Solvent in the filtrate was completely removed under reduced pressure, and the crude product was purified by column chromatograph (ISCO®; 12 g column; eluent:

0-50% DCM/MeOH; flow rate: 40 mL/min) to give compound B21. LCMS (ESI) m/z: 198.2[M+1]+

Intermediate B22

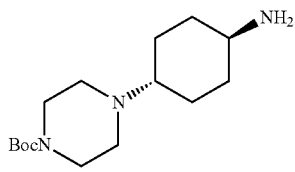 [SMILES: CC(C)(C)OC(=O)N1CCN([C@H]2CC[C@H](N)CC2)CC1]

Synthetic route

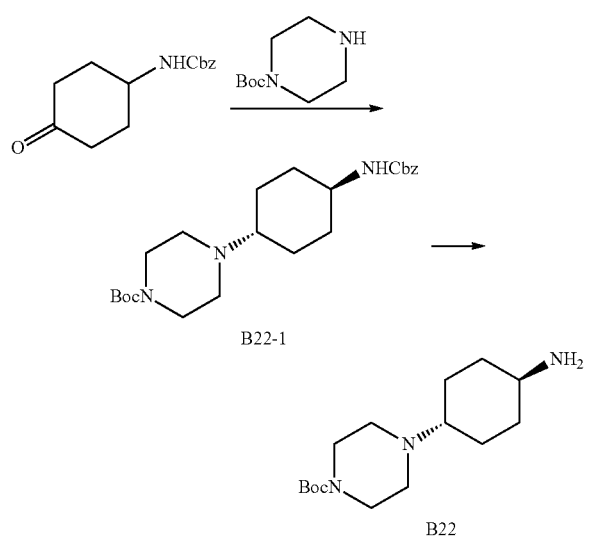

Step 1: Synthesis of Compound B22-1

Methanol (80 mL) was added with 4-N-benzyloxycarbonylaminocyclohexanone (5 g) and N-Boc piperazine (3.77 g), and then slowly added with sodium triacetoxyborohydride (6.43 g). The mixture was stirred at 25° C. for 12 hours. The solvent was completely removed under reduced pressure, and the residue was added with dichloromethane (100 mL) and water (100 mL) for extraction. The organic phase was dehydrated, filtered and concentrated under reduced pressure to give a crude product. The crude product was subjected to partition chromatograph (column: Agela Durashell 10 μm 250×50 mm; mobile phase: [water (10 mM NH₄HCO₃)-ACN]; B %: 35%-55%, 20 min) to separate the cis-trans isomers. (HPLC Shimadzu 20AD, X-bridge Shield RP18 2.1×50 mm, 5 μm, mobile phase [water+10 mmol/L ammonium bicarbonate-acetonitrile]; B %: 10%-80%, 4.5 min, Rt=2.615 min) the target fraction was concentrated to remove acetonitrile, and was added with dichloromethane (500 mL) for extraction. The organic phase was dehydrated, filtered and concentrated under reduced pressure to give compound B22-1. The product was used in the next step without purification.

Step 2: Synthesis of Compound B22

In argon atmosphere, wet palladium on carbon (0.2 g, 10%) was added to a hydrogenation flask, and methanol (5 mL) and compound B22-1 (0.2 g) were sequentially added to the reaction system, which was stirred in hydrogen atmosphere (50 Psi) at 30° C. for 2 hours. The reaction system was filtered through celite, the filter cake was rinsed with methanol (50 mL×3), and the solvent of the filtrate was removed under reduced pressure to give product B22. LCMS (ESI) m/z: 284.1[M+1]+

Intermediate B23

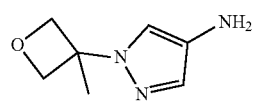

Synthetic route:

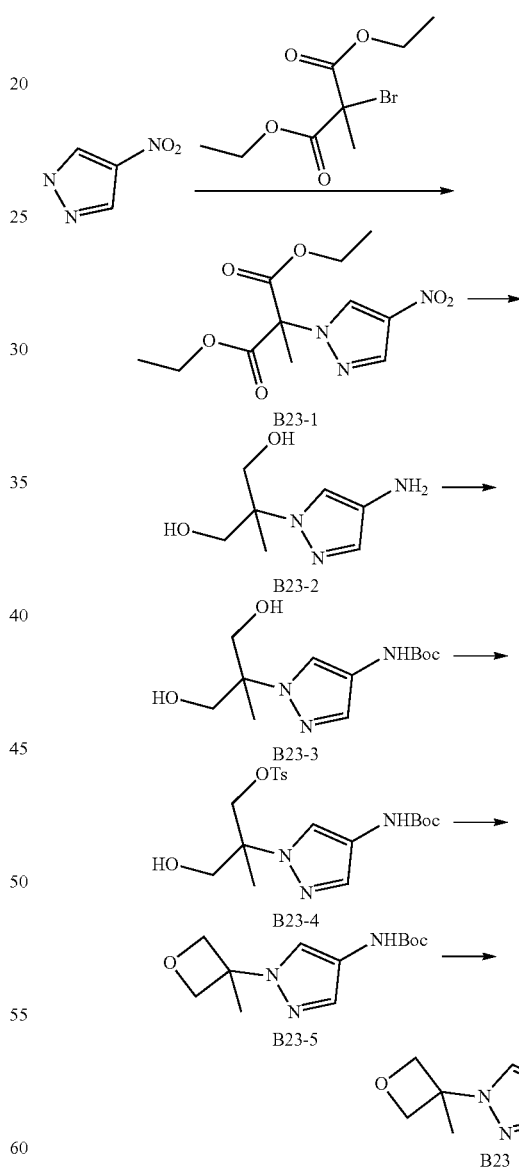

Step 1: Synthesis of Compound B23-1

4-nitropyrrole (1 g) and diethyl 2-bromo-2-methyl maleate (2.69 g) were dissolved in N,N-dimethylformamide (10 mL), and potassium carbonate (2.44 g) was added for reaction. The mixture was stirred at 100° C. for 15 hours.

The reaction system was added to ethyl acetate (20 mL), and washed with half-saturated brine (20 mL). The organic phase was dehydrated using anhydrous sodium sulfate, filtered, and concentrated under reduced pressure. The crude product was purified by column chromatograph (ISCO®; 20 g of SepaFlash® Silica Flash Column, Eluent of 0-60% DCM/MeOH gradient @ 40 mL/min) to give compound B23-1. LCMS (ESI) m/z: 286.1[M+1]+

Step 2: Synthesis of Compound B23-2

Compound B23-1 (1 g) was dissolved in methanol (10 mL), and sodium borohydride (265.26 mg) was added. The reaction system was stirred at 25° C. for 2 hours. The reaction system was added with 2 mL of saturated ammonium chloride, let stand until no bubbles were generated, and concentrated under reduced pressure. The crude product was purified by column chromatograph (ISCO®; 20 g of columns; eluent: 0-50% DCM/MeOH, 40 mL/min) to give compound B23-2. LCMS (ESI) m/z: 172.1[M+1]+

Step 3: Synthesis of Compound B23-3

Compound B23-2 (500 mg), di-tert-butyl dicarbonate (956.12 mg), and triethylamine (886.61 mg) were dissolved in anhydrous tetrahydrofuran (10 mL), and the mixture was stirred at 40° C. for 3 hours. The reaction system was concentrated under reduced pressure, and the crude product was purified by column chromatograph (ISCO®; 20 g; eluent: 0-50% DCM/MeOH @ 30 mL/min) to give compound B23-3. LCMS (ESI) m/z: 272.1[M−100+1]+

Step 4: Synthesis of Compound B23-4

Compound B23-3 (340 mg) was dissolved in a mixture of pyridine (10 mL) and dichloromethane (20 mL). The solution was cooled to 0° C., and then added with p-toluenesulfonyl chloride (238.91 mg, 1.25 mmol, 1 eq). The mixture was stirred at 0° C. for 3 hours. The resulting mixture was concentrated and purified by chromatograph (column: Welch Xtimate C18 150×25 mm×5 μm; mobile phase: [water (10 mM NH$_4$HCO$_3$)-ACN]; B %: 38%-68%, 10.5 min) to give compound B23-4. LCMS (ESI) m/z: 426.2[M+1]+

Step 5: Synthesis of Compound B23-5

Compound B23-4 (75 mg) was dissolved in anhydrous tetrahydrofuran (3 mL) and added with sodium hydride (21.15 mg, 60% purity) at 0° C. The reaction system was heated to 67° C. and stirred for 2 hours. The reaction was quenched by adding water (0.1 mL) and directly stirred using a silica gel stirrer. The crude product was purified by column chromatograph (ISCO®; 12 g of column; eluent: 0-80% ethyl acetate/petroleum ether; 20 mL/min) to give compound B23-5. LCMS (ESI) m/z: 254.2[M+1]+

Step 6: Synthesis of Compound B23

Compound B23-5 (20 mg) was dissolved in dichloromethane (1.5 mL), and trifluoroacetic acid (1.5 mL) was added. The mixture was stirred at 25° C. for 1 hour. The solvent of the resulting mixture was removed under reduced pressure to give compound B23. LCMS (ESI) m/z: 154.2 [M+1]+

Synthesis of intermediates in the table below was similar to that of intermediate B22, except that N-Boc piperazine was replaced with starting material one.

| Number | Structure | Starting material one | $^1$H NMR & MS |
|---|---|---|---|
| B24 | 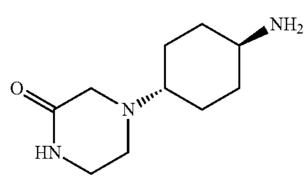 [SMILES: N[C@H]1CC[C@H](N2CCNC(=O)C2)CC1] | | $^1$H NMR (400 MHz, MeOD-d$_4$) δ = 3.25-3.31 (m, 2H), 3.14-3.21 (m, 2H), 2.70-2.79 (m, 2H), 2.59-2.69 (m, 1H), 2.27-2.42 (m, 1H), 1.88-1.98 (m, 2H), 1.72-1.88 (m, 2H), 1.54-1.67 (m, 2H), 1.12-1.39 (m, 2H). LCMS (ESI) m/z: 198.2 [M + 1]+ |
| B25 | 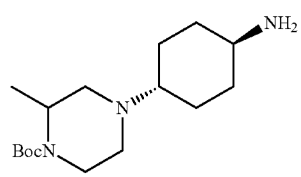 [SMILES: CC1CN([C@H]2CC[C@H](N)CC2)CCN1C(=O)OC(C)(C)C] | | $^1$H NMR (400 MHz, METHANOL-d4) δ = 4.19 (s, 1H), 3.82-3.78 (d, J = 16.0 Hz, 1H), 3.34 (s, 2H), 3.10-3.09 (m, 1H), 2.75-2.73 (d, J = 8.0 Hz, 2H), 2.40-2.37 (m, 1H), 2.29-2.23 (m, 3H), 1.97-1.90 (m, 4H), 1.5 (s, 9H), 1.35-1.23 (m, 7H). LCMS (ESI) m/z: 298.1 [M + 1]+ |
| B26 | 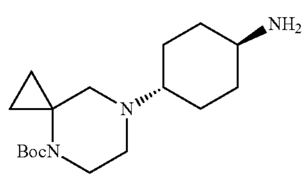 [SMILES: CC(C)(C)OC(=O)N1CCN([C@H]2CC[C@H](N)CC2)CC12CC2] | | LCMS (ESI) m/z: 310.2 [M + 1]+ |
| B27 | 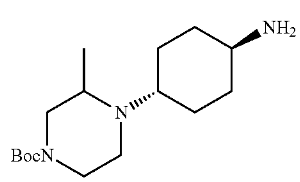 [SMILES: CC1CN(C(=O)OC(C)(C)C)CCN1[C@H]1CC[C@H](N)CC1] | | $^1$H NMR (400 MHz, MeOD-d$_4$) δ = 3.60-3.79 (m, 1H), 3.41-3.58 (m, 1H), 3.20-3.29 (m, 2H), 2.93-3.16 (m, 2H), 2.67-2.77 (m, 2H), 2.24-2.51 (m, 1H), 1.50-1.88 (m, 6H), 1.36-1.43 (m, 9H), 1.10-1.33 (m, 2H), 0.88-1.09 (m, 3H). LCMS (ESI) m/z: 298.1 |

-continued
| Number | Structure | Starting material one | ¹H NMR & MS |
|---|---|---|---|
| B28 | 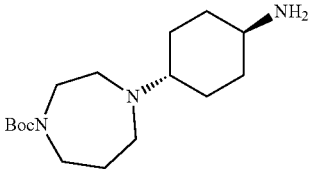 [SMILES: CC(C)(C)OC(=O)N1CCCN([C@H]2CC[C@H](N)CC2)CC1] | 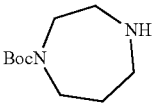 | ¹H NMR (400 MHz, DMSO-d$_6$) δ = 7.84-7.81 (m, 1H), 7.48-7.32 (m, 4H), 5.75-5.24 (m, 10H), 3.58-3.54 (m, 3H), 2.91-2.88 (m, 2H), 2.81-2.70 (m, 2H), 2.65 (s, 7H), 1.55 (s, 1H), 1.43-1.23 (m, 1H). LCMS (ESI) m/z: 298.3 |
| B29A | 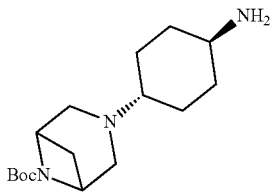 [SMILES: CC(C)(C)OC(=O)N1C2CC1CN([C@H]1CC[C@H](N)CC1)C2] | 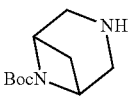 | LCMS (ESI) m/z: 296.2 [M + 1]+ |
| B29B | 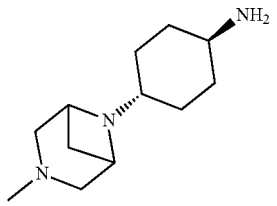 | 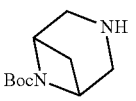 | LCMS (ESI) m/z: 210.2 [M + 1]+ |
| B30 | 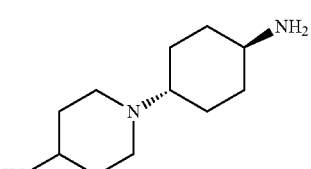 | 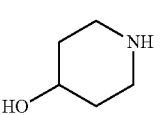 | LCMS (ESI) m/z: 199.3 [M + 1]+ |
| B31 | 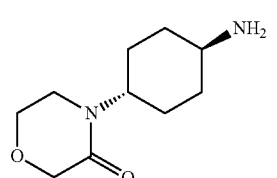 | 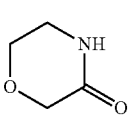 | LCMS (ESI) m/z: 199.1 [M + 1]+ |
| B32 | 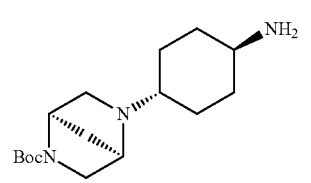 [SMILES: CC(C)(C)OC(=O)N1C[C@H]2C[C@@H]1CN2[C@H]1CC[C@H](N)CC1] |  | ¹H NMR (400 MHz, METHANOL-d4) δ = 4.35-4.27 (m, 1H), 3.93-3.74 (m, 1H), 3.54-3.43 (m, 1H), 3.37-3.34 (m, 1H), 3.26-3.11 (m, 2H), 3.10-3.01 (m, 1H), 2.65-2.59 (m, 1H), 2.53-2.41 (m, 1H), 2.12-2.03 (m, 2H), 1.92 (s, 4H), 1.87-1.75 (m, 3H), 1.68-1.58 (m, 1H), 1.49 (S, 9H). LCMS (ESI) m/z: 296.3 [M + 1]+ |
| B33 | 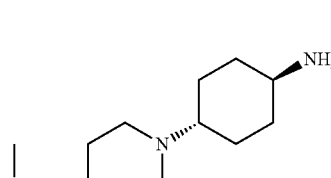 | 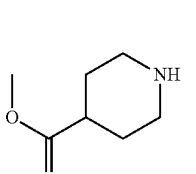 | LCMS (ESI) m/z: 241.2 [M + 1]+ |

| Number | Structure | Starting material one | ¹H NMR & MS |
|---|---|---|---|
| B34 | 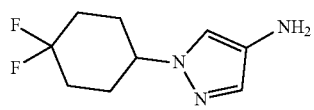 [SMILES: Nc1cnn(C2CCC(F)(F)CC2)c1] | 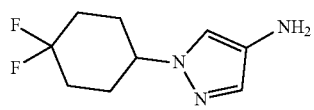 [SMILES: Nc1cnn(C2CCC(F)(F)CC2)c1] | LCMS (ESI) m/z: 226.3 [M + 1]+ |

Intermediate B35

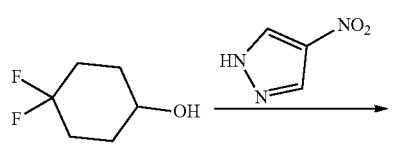

Synthetic route:

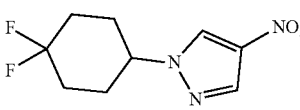

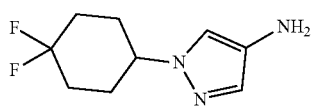

B35

Step 1: Synthesis of Compound B35-1

Diisopropyl azodicarboxylate (854.05 mg) was added to a solution of 4,4-difluorocyclohexanol (0.5 g), 4-nitropyrazole (415.29 mg) and triphenylphosphine (1.06 g) in tetrahydrofuran (20 mL), and the mixture was stirred at 20° C. for 12 hours. The solvent was completely removed under reduced pressure, and the crude product was purified by column chromatograph (petroleum ether to petroleum ether:ethyl acetate=3:1) to give compound B35-1.

Step 2: Synthesis of Compound B35

Compound B35-1 (2 g) was added to methanol (70 mL), and wet palladium on carbon (1 g, purity: 10%) was added. After three hydrogen purges, the mixture was stirred at 30° C. for 2 hours in hydrogen atmosphere (30 Psi), and filtered through celite. The solvent of the filtrate was completely removed under reduced pressure to give compound B35. LCMS (ESI) m/z: 202.2[M+H].

Reference Example 1: WXR1

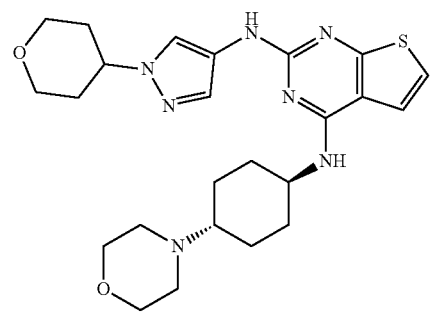 [SMILES: c1cc2c(N[C@H]3CC[C@H](N4CCOCC4)CC3)nc(Nc3cnn(C4CCOCC4)c3)nc2s1]

Compound WXR1 was synthesized according to the route reported in Patent No. WO2017205762.

Reference Example 2: WXR2

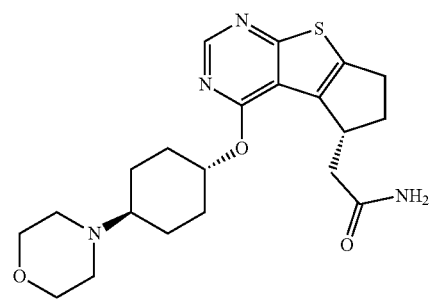 [SMILES: NC(=O)C[C@H]1CCc2sc3ncnc(O[C@H]4CC[C@H](N5CCOCC5)CC4)c3c21]

Compound WXR2 (ND-2110) was synthesized according to the route reported in Patent No. WO2012097013.

Reference Example 3: WXR3

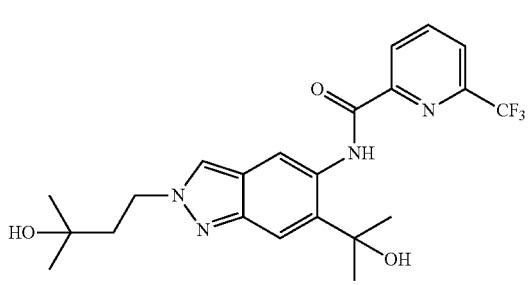 [SMILES: CC(C)(O)CCn1cc2cc(NC(=O)c3cccc(C(F)(F)F)n3)c(C(C)(C)O)cc2n1]

Compound WXR3 (BAY-1830839) was synthesized according to the route reported in Patent No. WO2017186700.

LCMS (ESI) m/z: 451.2[M+H]$^+$. $^1$H NMR (400 MHz, DMSO-d$_6$) δ=12.35 (s, 1H), 8.71 (s, 1H), 8.45 (d, J=7.6 Hz, 2H), 8.37 (t, J=6.0 Hz, 1H), 8.16 (d, J=6.8 Hz, 1H), 7.57 (s, 1H), 5.93 (d, J=8.0 Hz, 1H), 4.51 (s, 1H), 4.49-4.45 (m, 2H), 2.05-2.01 (m, 2H), 1.62 (s, 6H), 1.15 (s, 6H)

Reference Example 4: WXR4

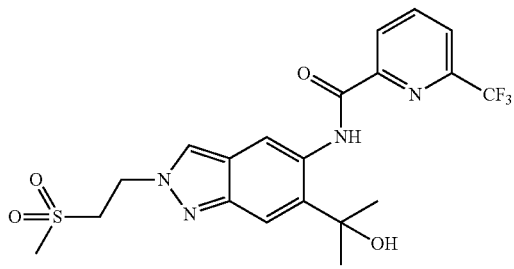 [SMILES: CC(C)(O)c1cc2nn(CCS(C)(=O)=O)cc2cc1NC(=O)c1cccc(C(F)(F)F)n1]

Compound WXR4 (BAY-1834845) was synthesized according to the route reported in Patent No. WO2017186689.

LCMS (ESI) m/z: 471.2[M+H]$^+$. $^1$H NMR (400 MHz, DMSO-d$_6$) δ=12.37 (s, 1H), 8.73 (s, 1H), 8.48-8.42 (m, 2H), 8.40-8.32 (m, 1H), 8.16 (d, J=7.8 Hz, 1H), 7.59 (s, 1H), 5.99 (s, 1H), 4.86 (t, J=6.6 Hz, 2H), 3.85 (t, J=6.6 Hz, 2H), 2.90 (s, 3H), 1.62 (s, 6H).

Example 1: Synthesis of Compound WX001

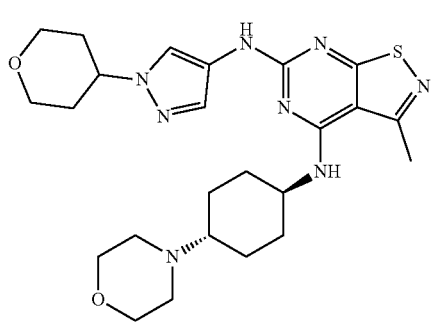 [SMILES: Cc1nsc2nc(Nc3cnn(C4CCOCC4)c3)nc(N[C@H]3CC[C@H](N4CCOCC4)CC3)c12]

Synthetic route:

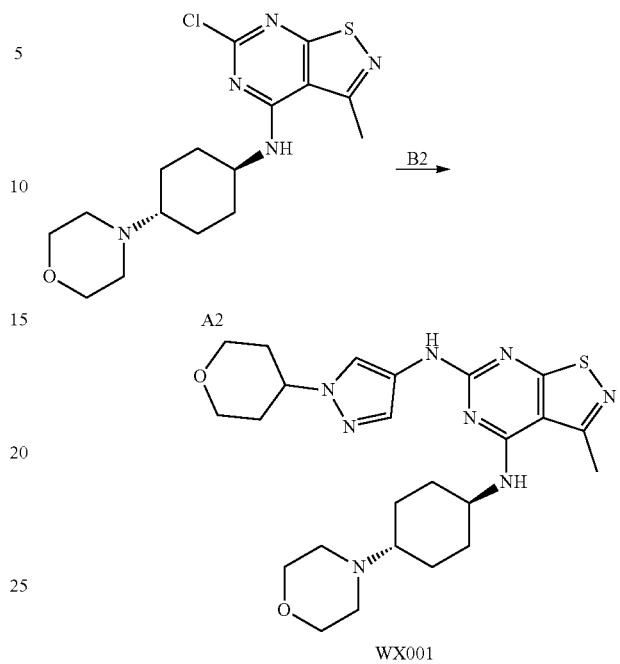

Example 1: Synthesis of Compound WX001

Intermediate A2 (0.15 g) was dissolved in n-butanol (1 mL), followed by addition of hydrochloric acid/ethyl acetate (4 M, 1.02 mL) and intermediate B2 (81.81 mg). The mixture was stirred at 120° C. for 16 h. The resulting mixture was filtered. The filter cake was washed with ethyl acetate (2 mL×3) and the filter cake was dried to give a crude product. The crude product was purified by preparative chromatograph (dichloromethane:methanol=10:1) to give crude WX001, which was slurried with 2 mL of methanol to give compound WX001.

LCMS (ESI) m/z: 499.2 [M+H]$^+$. $^1$H NMR (400 MHz, DMSO-d$_6$) δ=9.05 (s, 1H), 7.90 (s, 1H), 7.55 (s, 1H), 6.10 (d, J=7.2 Hz, 1H), 4.40-4.31 (m, 1H), 4.16-4.05 (m, 1H), 4.01-3.94 (m, 2H), 3.83-3.77 (m, 1H), 3.63-3.57 (m, 4H), 3.48 (dt, J=3.2, 11.2 Hz, 2H), 2.68 (s, 3H), 2.34-2.24 (m, 2H), 2.18-2.10 (m, 2H), 2.03-1.91 (m, 7H), 1.60-1.48 (m, 2H), 1.44-1.32 (m, 2H).

Example 2: Synthesis of Compound WX002

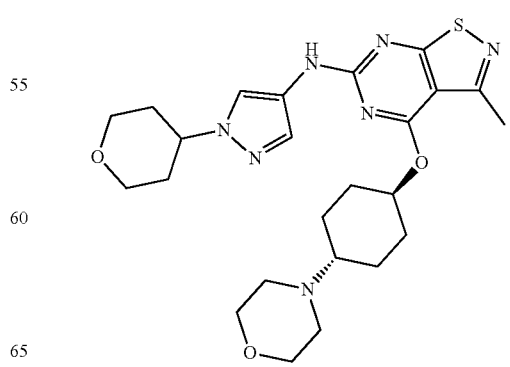

Synthetic route:

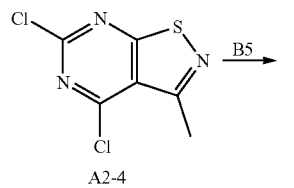

A2-4

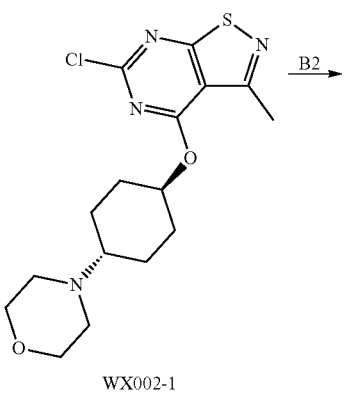

WX002-1

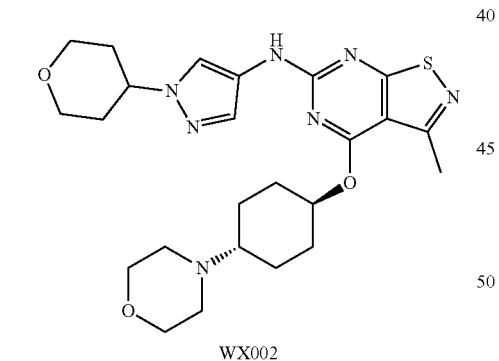

WX002

Synthesis of compound WX002 starting from intermediates A2-4, B5, and B2 was similar to the step 5 of A2 synthesis and the steps of compound WX001 synthesis.

LCMS (ESI) m/z: 500.2 [M+H]$^+$. $^1$H NMR (400 MHz, CHLOROFORM-d) δ=8.03 (s, 1H), 7.64-7.37 (m, 1H), 7.09-6.83 (m, 1H), 4.27 (td, J=8.0, 15.7 Hz, 1H), 4.15-4.12 (m, 2H), 4.06 (br d, J=11.8 Hz, 2H), 3.74-3.72 (m, 2H), 3.54-3.40 (m, 2H), 2.60 (s, 3H), 2.52 (br s, 3H), 2.56-2.47 (m, 1H), 2.24 (br d, J=13.1 Hz, 2H), 2.06 (br s, 4H), 1.97 (br d, J=10.8 Hz, 2H), 1.58-1.49 (m, 2H), 1.46-1.38 (m, 2H), 0.84-0.74 (m, 2H).

Example 3: Synthesis of Compound WX003

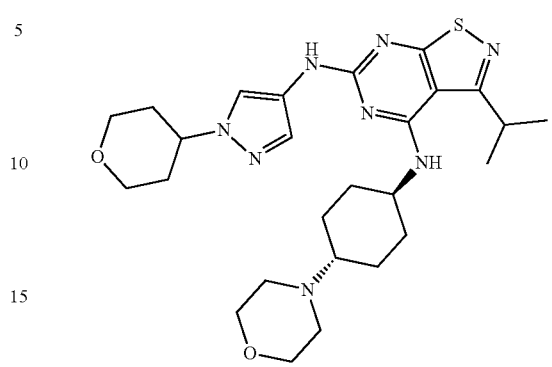

Synthetic route:

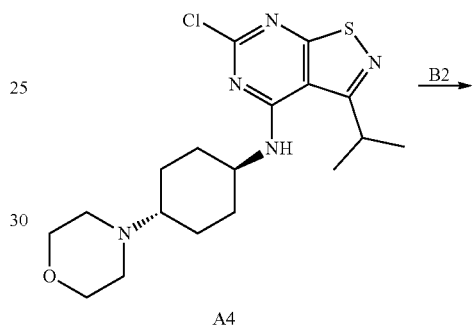

A4

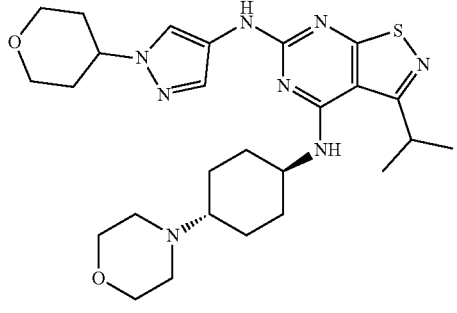

WX003

Synthesis of compound WX003 starting from intermediates A4 and B2 was similar to the steps of compound WX001 synthesis.

LCMS (ESI) m/z: 527.2 [M+H]$^+$. $^1$H NMR (400 MHz, DMSO-d6) δ=9.04 (br s, 1H), 7.88 (s, 1H), 7.52 (s, 1H), 6.06 (br s, 1H), 4.38-4.27 (m, 1H), 4.20-4.08 (m, 1H), 4.00-3.89 (m, 2H), 3.60-3.40 (m, 11H), 2.33-2.22 (m, 1H), 2.15-2.05 (m, 2H), 2.03-1.87 (m, 6H), 1.60-1.46 (m, 2H), 1.42-1.25 (m, 8H).

Example 4: Synthesis of Compound WX004

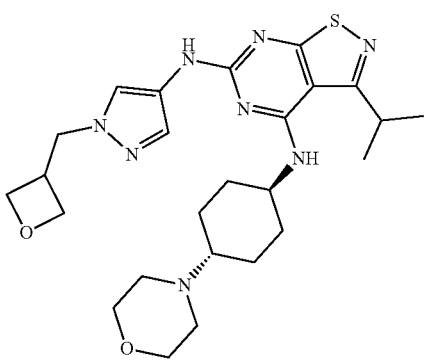 [SMILES: CC(C)c1nsc2nc(Nc3cnn(CC4COC4)c3)nc(N[C@H]3CC[C@H](N4CCOCC4)CC3)c12]

Synthetic route:

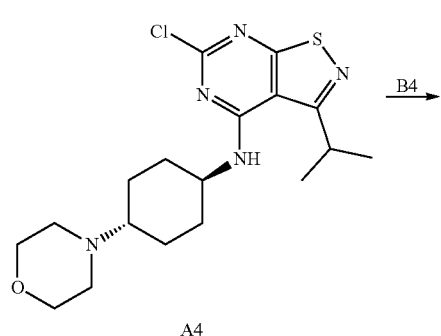

A4

Example 5: Synthesis of Compound WX005

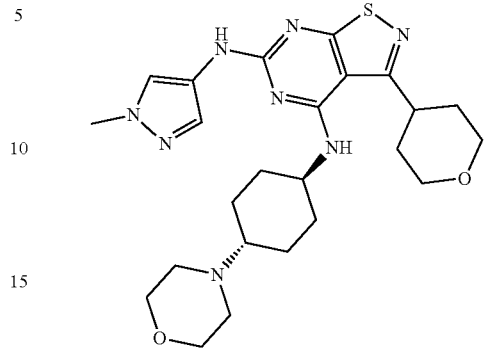

Synthetic route:

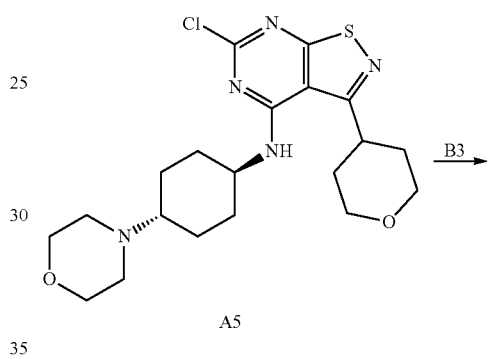

A5

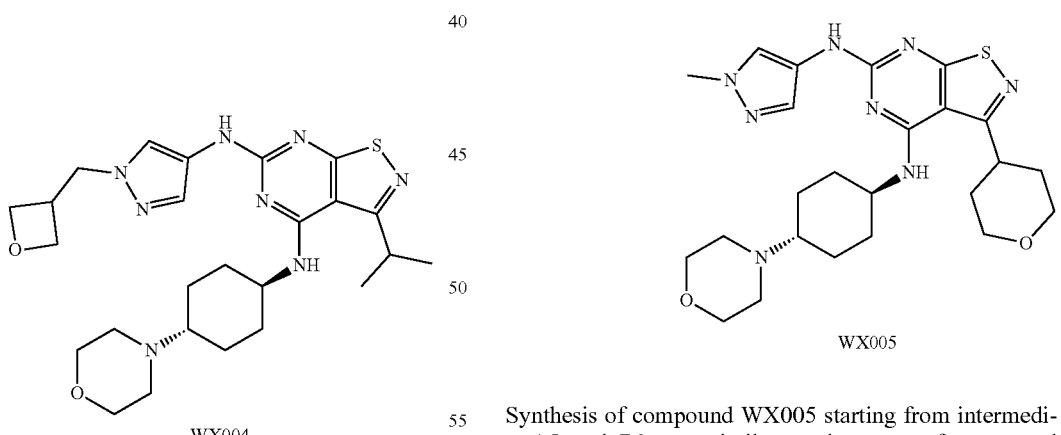

WX004

Synthesis of compound WX004 starting from intermediates A4 and B4 was similar to the steps of compound WX001 synthesis.

LCMS (ESI) m/z: 513.3 [M+H]$^+$. $^1$H NMR (400 MHz, METHANOL-d$_4$) δ=8.60 (s, 2H), 4.89-4.79 (m, 2H), 4.73-4.60 (m, 2H), 4.45-4.33 (m, 1H), 4.14-4.05 (m, 2H), 4.02-3.91 m, 2H), 3.82 (d, J=5.2 Hz, 2H), 3.72-3.52 (m, 5H), 3.28-3.18 (m, 2H), 2.44-2.25 (m, 4H), 2.25-2.25 (m, 1H), 1.94-1.73 (m, 4H), 1.39 (d, J=6.8 Hz, 6H)

Synthesis of compound WX005 starting from intermediates A5 and B3 was similar to the steps of compound WX001 synthesis.

LCMS (ESI) m/z: 499.3 [M+H]$^+$. $^1$H NMR (400 MHz, DMSO-d6) δ=9.54-9.22 (m, 1H), 8.04-7.70 (m, 1H), 7.50 (br s, 1H), 6.51-6.09 (m, 1H), 4.12-4.00 (br s, 1H), 3.96-3.86 (m, 3H), 3.80 (s, 3H), 3.72-3.49 (m, 7H), 2.67 (s, 3H), 2.32-2.22 (m, 1H), 2.17-2.07 (m, 2H), 1.99-1.82 (m, 4H), 1.81-1.65 (m, 2H), 1.60-1.45 (m, 2H), 1.37 (br s, 2H)

Referring to the synthetic procedures in Example 1, the following examples were synthesized starting from fragment 1 and fragment 2 in the following table.

| Examples | Fragment 1 | Fragment 2 | Compound | Structure | ¹H NMR | MS m/z [M + H]⁺ |
|---|---|---|---|---|---|---|
| 6 | B15 | A2 | WX006 | 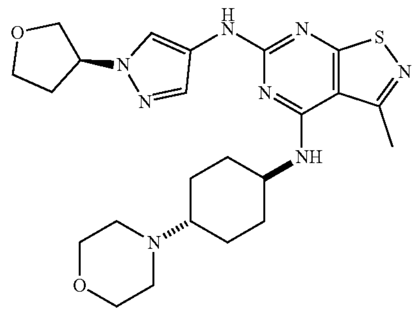 [SMILES: Cc1nsc2nc(Nc3cnn([C@H]4CCOC4)c3)nc(N[C@H]3CC[C@H](N4CCOCC4)CC3)c12] | ¹H NMR (400 MHz, DMSO-d₆) δ = 9.03 (s, 1H), 7.85 (s, 1H), 7.54 (s, 1H), 6.07-6.05 (m, 1H), 4.95-4.92 (m, 1H), 3.99-3.96 (m, 1H), 3.95-3.94 (m, 2H), 3.90-3.89 (m, 1H), 3.82-3.79 (m, 1H), 3.57-3.55 (m, 4H), 2.65 (s, 3H), 2.59-2.69 (m, 3H), 2.24-2.44 (m, 4H), 2.11-2.08 (m, 2H), 1.92-1.89 (m, 2H), 1.51-1.48 (m, 2H), 1.36-1.30 (m, 2H) | 485.4 |
| 7 | B16 | A2 | WX007 | 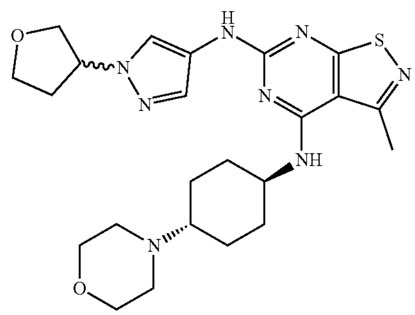 [SMILES: Cc1nsc2nc(Nc3cnn(C4CCOC4)c3)nc(N[C@H]3CC[C@H](N4CCOCC4)CC3)c12] | ¹H NMR (400 MHz, DMSO-d₆) δ = 9.04 (s, 1H), 7.85 (s, 1H), 7.54 (s, 1H), 6.15 (br s, 1H), 4.94 (br s, 1H), 4.20-4.06 (m, 1H), 3.96-3.95 (m, 2H), 3.91-3.82 (m, 1H), 3.78 (m, 1H), 3.57-3.56 (m, 4H), 2.64 (s, 3H), 2.47-2.46 (m, 3H), 2.29-2.24 (m, 4H), 2.10-2.07 (m, 2H), 1.92-1.89 (m, 2H), 1.51-1.48 (m, 2H), 1.36-1.32 (m, 2H) | 485.4 |
| 8 | B17 | A2 | WX008 | 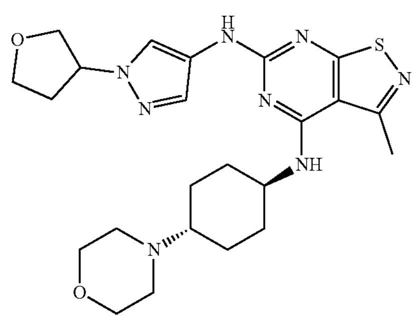 [SMILES: Cc1nsc2nc(Nc3cnn(C4CCOC4)c3)nc(N[C@H]3CC[C@H](N4CCOCC4)CC3)c12] | ¹H NMR (400 MHz, DMSO-d₆) δ = 9.44 (s, 1 H), 7.80-8.09 (m, 1H), 7.560 (s, 1H), 6.10-6.43 (m, 1H), 5.00 (s, 1H), 4.08 (s, 1H), 3.99-4.00 (m, 2H), 3.96-9.98 (m, 1H), 3.83-3.81 (m, 1H), 3.59 (m, 4H), 2.69 (s, 3H), 2.37-2.34 (m, 3H), 2.27-2.24 (m, 2H), 2.09 (br s, 2H), 1.92 (m, 2H), 1.55-1.52 (m, 2H), 1.49-1.37 (m, 2H), 1.20-1.18 (m, 2H) | 485.4 |
| 9 | B19 | A2 | WX009 | 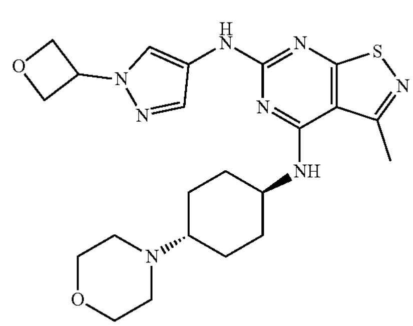 [SMILES: Cc1nsc2nc(Nc3cnn(C4COC4)c3)nc(N[C@H]3CC[C@H](N4CCOCC4)CC3)c12] | ¹H NMR (400 MHz, D₂O) δ = 8.67 (s, 2H), 8.01 (s, 1H), 7.92 (s, 1H), 5.68-5.71 (t, J = 6.4 Hz, 1H), 5.37-5.41 (t, J = 7.5 Hz, 2H), 5.17-5.20 (t, J = 6.6 Hz, 2H), 4.10-4.27 (m, 5H), 3.54-3.65 (m, 5H), 2.71 (s, 3H), 2.49-2.52 (d, J = 10 Hz, 4H), 1.72-1.88 (m, 4H). | 471.1 |

-continued
| Examples | Fragment 1 | Fragment 2 | Compound | Structure | ¹H NMR | MS m/z [M + H]⁺ |
|---|---|---|---|---|---|---|
| 10 | B18 | A2 | WX010 | 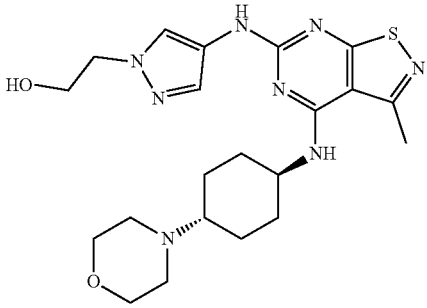 [SMILES: Cc1nsc2nc(Nc3cnn(CCO)c3)nc(N[C@H]3CC[C@H](N4CCOCC4)CC3)c12] | ¹H NMR (400 MHz, DMSO-d₆) δ = 11.15 (s, 1H), 10.14 (s, 1H), 7.95 (s, 1H), 7.52 (s, 1H), 6.88 (s, 1H), 4.16 (s, 3H), 3.89-4.03 (m, 4H), 3.71-3.75 (t, J = 5.6 Hz, 2H), 3.45-3.51 (d, J = 11.2 Hz, 2H), 3.13 (s, 3H), 2.67-2.72 (m, 3H), 2.00-2.37 (m, 4H), 1.55-1.83 (m, 4H). | 459.3 |
| 11 | B21 | A2 | WX011 | 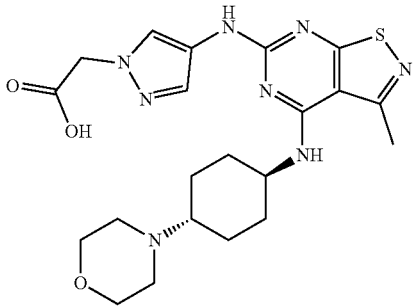 [SMILES: Cc1nsc2nc(Nc3cnn(CC(=O)O)c3)nc(N[C@H]3CC[C@H](N4CCOCC4)CC3)c12] | ¹H NMR (400 MHz, DMSO-d₆) δ = 11.80-11.42 (m, 1H), 8.11-7.91 (m, 1H), 7.61-7.41 (m, 1H), 7.28-6.97 (m, 1H), 5.13-5.04 (m, 2H), 4.28-4.03 (m, 1H), 3.99-3.88 (m, 4H), 3.55-3.31 (m, 2H), 3.24-2.98 (m, 3H), 2.85-2.70 (m, 3H), 2.37-2.23 (m, 3H), 2.19-2.00 (m, 2H), 1.80-1.56 (m, 4H) | 473.3 |
| 13 | B2 | A7 | WX013 | 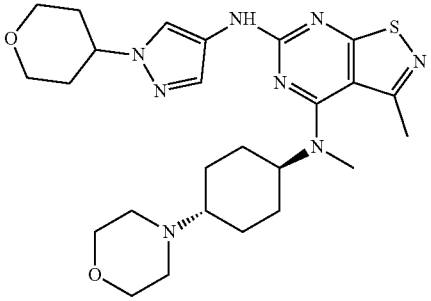 [SMILES: Cc1nsc2nc(Nc3cnn(C4CCOCC4)c3)nc(N(C)[C@H]3CC[C@H](N4CCOCC4)CC3)c12] | ¹H NMR (400 MHz, CDCl₃) δ = 7.91 (s, 1H), 7.56 (s, 1H), 6.77 (s, 1H), 4.37-4.32 (m, 1H), 4.15-4.12 (m, 2H), 3.95-3.89 (m, 1H), 3.74-3.72 (m, 4H), 3.59-3.53 (m, 2H), 3.01 (s, 3H), 2.66 (s, 3H), 2.58-2.56 (m, 4H), 2.29-2.23 (m, 1H), 2.14-1.93 (m, 8H), 1.71 (q, 2H), 1.38 (q, 2H). | 513.4 |
| 14 | B20 | A2 | WX014 | 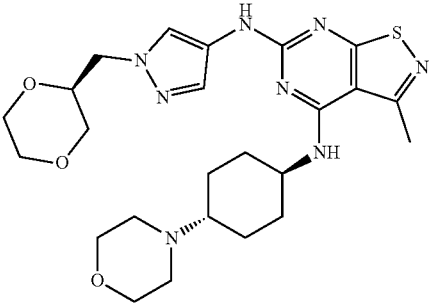 [SMILES: Cc1nsc2nc(Nc3cnn(C[C@H]4COCCO4)c3)nc(N[C@H]3CC[C@H](N4CCOCC4)CC3)c12] | ¹H NMR (400 MHz, DMSO-d₆) δ = 9.49 (s, 1H), 7.87 (s, 1H), 7.50 (s, 1H), 6.19-6.39 (m, 1H), 4.01-4.13 (m, 3H), 3.37-3.85 (m, 12H), 3.19-3.25 (m, 1H), 2.57-2.68 (m, 4H), 1.92-2.33 (m, 4H), 1.15-1.58 (m, 6H). | 515.3 |
| 15 | B20 | A2 | WX015 | 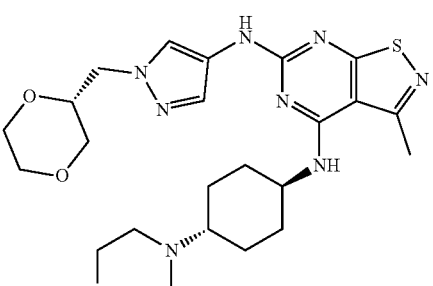 | ¹H NMR (400 MHz, DMSO-d₆) δ = 9.50 (s, 1H), 7.87 (s, 1H), 7.50 (s, 1H), 6.15-6.29 (m, 1H), 3.96-4.16 (m, 3H), 3.40-3.82 (m, 12H), 3.17-3.25 (m, 1H), 2.68 (s, 4H), 1.85-2.18 (m, 5H), 1.19-1.57 (m, 5H). | 515.3 |

-continued
| Examples | Fragment 1 | Fragment 2 | Compound | Structure | ¹H NMR | MS m/z [M + H]⁺ |
|---|---|---|---|---|---|---|
| 24 | B23 | A2 | WX024 | 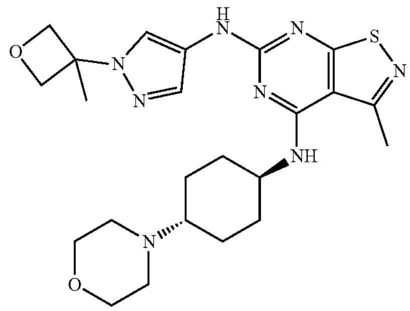 [SMILES: Cc1nsc2nc(Nc3cnn(C4(C)COC4)c3)nc(N[C@H]3CC[C@H](N4CCOCC4)CC3)c12] | ¹H NMR (400 MHz, MeOD-d₄) δ = 8.05-7.65 (m, 2H), 5.15-5.05 (m, 2H), 4.7-4.65 (m, 2H), 4.2 (m, 1H), 3.70-3.65 (m, 4H), 2.95 (s, 3H), 2.70-2.65 (m, 4H), 2.30 (m, 1H), 2.26-2.20 (m, 2H), 2.05 (m, 2H), 1.92 (s, 3H), 1.50-1.48 (m, 4H) | 484.6 |
| 55 | B2 | A6 | WX055 | 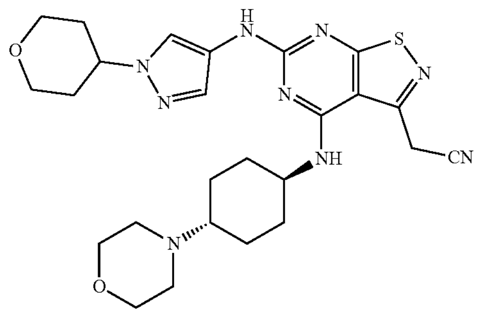 [SMILES: N#CCc1nsc2nc(Nc3cnn(C4CCOCC4)c3)nc(N[C@H]3CC[C@H](N4CCOCC4)CC3)c12] | ¹H NMR (400 MHz, CDCl₃) δ = 7.97 (s, 1H), 7.56 (m, 1H), 6.84 (s, 1H), 5.20 (s, 1H), 4.37-4.33 (m, 1H), 4.15-4.12 (m, 2H), 4.09 (s, 2H), 3.76-3.74 (m, 4H), 3.60-3.53 (m, 3H), 2.61-2.59 (m, 4H), 2.33 (m, 3H), 2.14-2.13 (m, 4H), 2.07-2.04 (m, 2H), 1.49-1.26 (m, 4H). | 524.3 |
| 56 | B2 | A6 | WX056 | 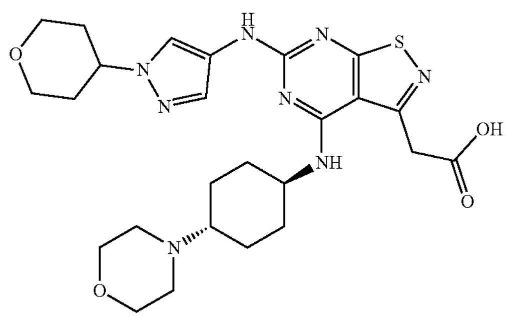 [SMILES: O=C(O)Cc1nsc2nc(Nc3cnn(C4CCOCC4)c3)nc(N[C@H]3CC[C@H](N4CCOCC4)CC3)c12] | ¹H NMR (400 MHz, DMSO-d6) δ = 9.31 (s, 1H), 7.90 (s, 1H), 7.58 (s, 1H), 6.91 (s, 1H), 4.42 (m, 1H), 3.98-3.96 (m, 6H), 3.56-3.42 (m, 5H), 3.20 (m, 4H), 2.67 (m, 1H), 2.33-2.25 (m, 5H), 2.00-1.95 (m, 4H), 1.75-1.72 (m, 2H), 1.53-1.50 (m, 2H). | 543.3 |
Example 25: Synthesis of Compound WX025
Synthetic route:
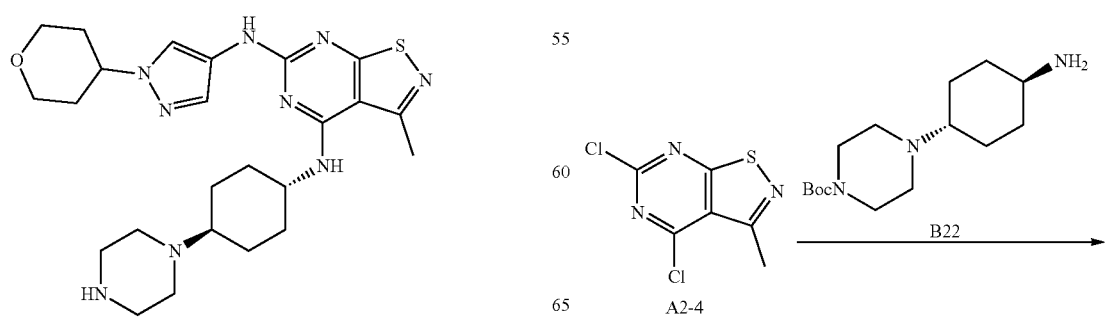

87

-continued

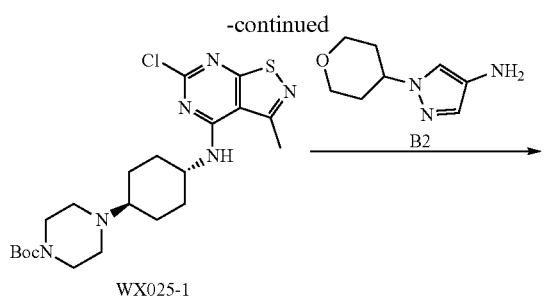

WX025-1

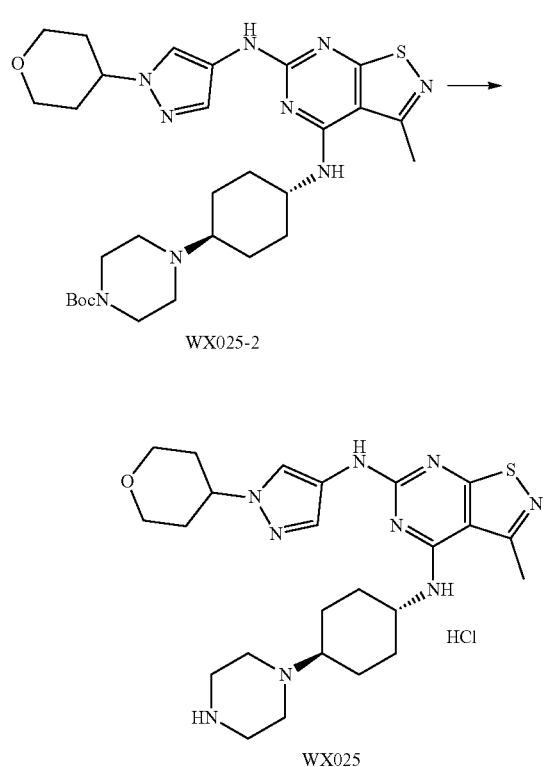

Step 1:

Referring to intermediate A2 synthesis, the compound WX025-1 was synthesized starting with intermediates A2-4 and B22.

Step 2:

Referring to WX001 synthesis, the compound WX025-2 was synthesized starting with intermediates WX025-1 and B2.

Step 3: Synthesis of Compound WX025

Compound WX025-2 (0.18 g) was mixed with a solution of hydrochloric acid in methanol (15 mL, 4 M) in a flask. The mixture was stirred at 15° C. for 12 hours, and the reaction solution was concentrated under reduced pressure. The crude product was purified by chromatograph (column: Boston Prime C18 150×30 mm×5 μm; mobile phase: [water (0.05% HCl)-ACN]; B %: 1%-22%, 10 min) to give compound WX025. LCMS (ESI) m/z: 498.1 [M+H]. $^1$H NMR (400 MHz, MeOD-$d_4$) δ=7.99 (s, 1H), 7.80-7.65 (m, 1H), 4.49-4.23 (m, 2H), 4.10-4.08 (d, J=8.0 Hz, 2H), 3.72-3.50 (m, 11H), 2.80 (s, 3H), 2.40-2.36 (m, 4H), 2.10 (s, 4H), 1.83-1.75 (m, 4H).

88

Example 26: Synthesis of Compound WX026

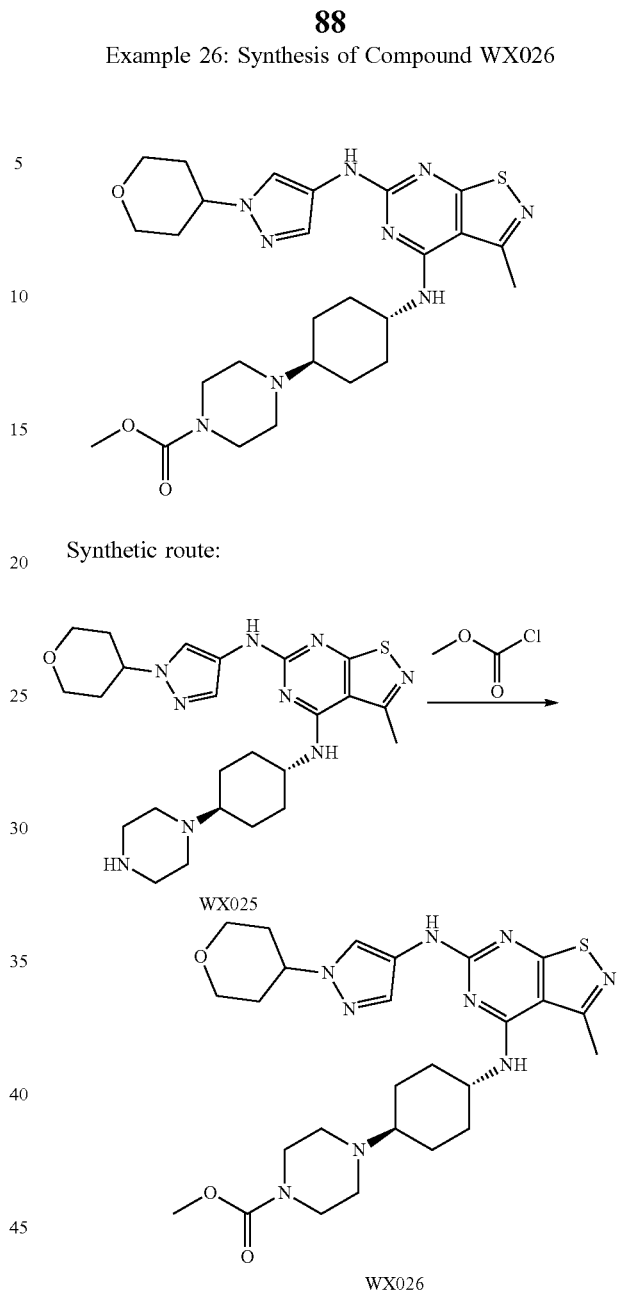

Step 1: Synthesis of Compound WX026

To a reaction flask were added compound WX025 (0.03 g, HCl salt) and dichloromethane (2 mL), followed by triethylamine (14.21 mg). The mixture was stirred, and added dropwise with methyl chloroformate (6.37 mg, 5.22 μL). The resulting mixture was stirred at 15° C. for 2 hours. The reaction was quenched with 30 mL of water, and ethyl acetate (30 mL×2) was added for extraction. The combined organic phases were dehydrated using anhydrous sodium sulfate, filtered and concentrated under reduced pressure. The crude product obtained was purified by chromatograph (column: Xtimate C18 150×25 mm×5 μm; mobile phase: [water (0.04% NH$_3$H$_2$O+10 mM NH$_4$HCO$_3$)-ACN]; B %: 30%-55%, 10.5 min) to give compound WX026. LCMS (ESI) m/z: 556.4 [M+H], $^1$H NMR (400 MHz, CDCl$_3$) δ=8.00 (s, 1H), 7.55 (s, 1H), 6.81 (s, 1H), 5.19 (s, 1H), 4.34 (m, 1H), 4.14-4.11 (m, 3H), 3.72 (s, 3H), 3.55-3.50 (m, 6H), 2.70 (s, 3H), 2.56 (s, 4H), 2.41-2.30 (m, 3H), 2.13 (s, 4H), 2.01-1.98 (m, 2H), 1.50-1.44 (m, 2H), 1.33-1.30 (m, 2H).

Referring to the synthetic procedures of Example 25 and Example 26, the following examples were synthesized starting from intermediate A2-4, fragment 1 and fragment 2 in the following table.

| Examples | Fragment 1 | Fragment 2 | Compound | Structure | NMR | MS m/z [M + H]+ |
|---|---|---|---|---|---|---|
| 27 | B22 | B2 | WX027 | 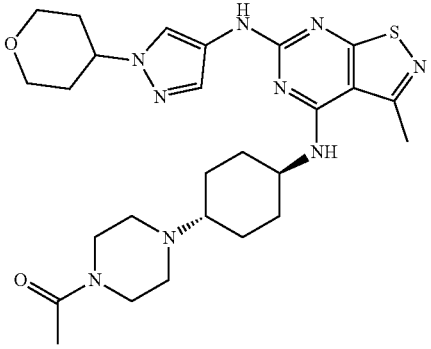 [SMILES: CC(=O)N1CCN([C@H]2CC[C@H](Nc3nc(Nc4cnn(C5CCOCC5)c4)nc4snc(C)c34)CC2)CC1] | ¹H NMR (400 MHz, DMSO-d₆) δ = 9.48-9.37 (m, 1H), 7.94-8.03 (m, 1H), 7.54-7.61 (m, 1H), 6.75-6.83 (m, 1H), 4.31-4.39 (m, 1H), 4.07-4.22 (m, 4H), 3.48-3.69 (m, 6H), 2.68-2.73 (m, 3H), 2.53-2.65 (m, 3H), 2.30-2.44 (m, 3H), 2.00-2.23 (m, 9H), 1.24-1.39 (m, 4H) | 540.3 |
| 28 | B22 | B2 | WX028 | 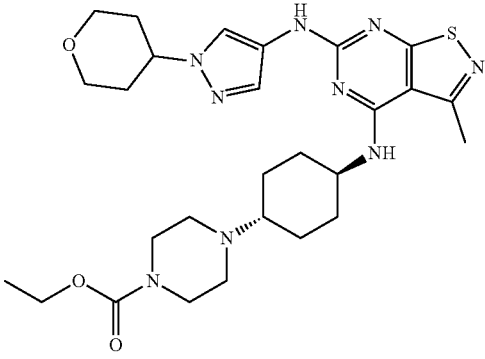 [SMILES: CCOC(=O)N1CCN([C@H]2CC[C@H](Nc3nc(Nc4cnn(C5CCOCC5)c4)nc4snc(C)c34)CC2)CC1] | ¹H NMR (400 MHz, CDCl₃) δ = 8.00 (s, 1H), 7.55 (s, 1H), 6.83 (s, 1H), 5.20 (s, 1H), 4.28-4.36-4.34 (m, 1H), 4.18-4.11 (m, 5H), 3.56-3.49 (m, 6H), 2.69 (s, 3H), 2.57-2.55 (m, 4H), 2.45-2.42 (m, 1H), 2.31-2.29 (m, 2H), 2.14-2.12 (m, 4H), 2.06-1.98 (m, 2H), 1.50-1.47 (m, 2H), 1.33-1.26 (m, 5H) | 570.3 |
| 29 | B22 | B2 | WX029 | 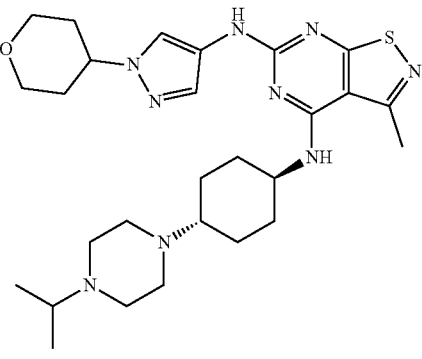 | ¹H NMR (400 MHz, CDCl₃) δ = 8.00 (s, 1H), 7.54 (s, 1H), 6.80 (s, 1H), 5.20 (s, 1H), 4.25-4.33 (m, 1H), 4.14-4.11 (m, 3H), 3.59-3.54 (m, 2H), 2.69-2.60 (m, 10H), 2.32-2.29 (m, 3H), 2.15-2.11 (m, 4H), 2.06-2.03 (m, 2H), 1.65-1.53 (m, 2H), 1.51-1.47 (m, 2H), 1.32-1.29 (m, 2H), 1.08 (d, J = 6.8 Hz, 6H) | 540.3 |
| 30 | B22 | B2 | WX030 | 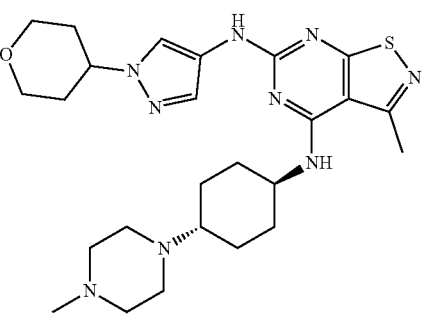 [SMILES: Cc1nsc2nc(Nc3cnn(C4CCOCC4)c3)nc(N[C@H]3CC[C@H](N4CCN(C)CC4)CC3)c12] | ¹H NMR (400 MHz, CDCl₃) δ = 7.94 (s, 1H), 7.54 (s, 1H), 6.76 (s, 1H), 5.20-5.19 (m, 1H), 4.36-4.34 (m, 1H), 4.15-4.12 (m, 3H), 3.57-3.55 (m, 2H), 2.75-2.70 (m, 9H), 2.37-2.33 (m, 6H), 2.14-2.07 (m, 7H), 1.33-1.26 (m, 4H) | 512.3 |

-continued

| Examples | Fragment 1 | Fragment 2 | Compound | Structure | NMR | MS m/z [M + H]+ |
|---|---|---|---|---|---|---|
| 31 | B22 | B2 | WX031 | 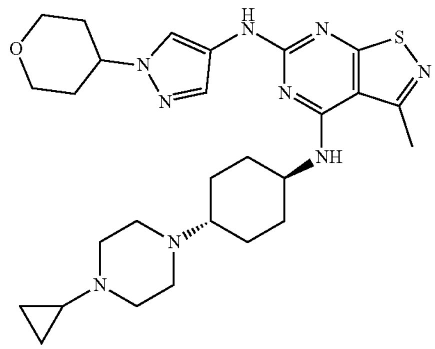 [SMILES: Cc1nsc2nc(Nc3cnn(C4CCOCC4)c3)nc(N[C@H]3CC[C@H](N4CCN(C5CC5)CC4)CC3)c12] | ¹H NMR (400 MHz, MeOD-d₄) δ = 7.95 (s, 1H), 7.60 (s, 1H), 4.62-4.52 (m, 1H), 4.31-4.48 (m, 2H), 4.14-4.27 (m, 2H), 4.08-4.06 (m, 2H), 3.58 (s, 2H), 3.57 (s, 1H), 3.31-3.30 (m, 1H), 2.69 (s, 5H), 2.34-2.46 (m, 2H), 2.19-2.31 (m, 2H), 2.08-2.06 (m, 4H), 1.68 (s, 2H), 1.50 (s, 4H), 0.50-0.49 (m, 4H), 0.43 (s, 1H) | 538.3 |
| 32 | B22 | B17 | WX032 | 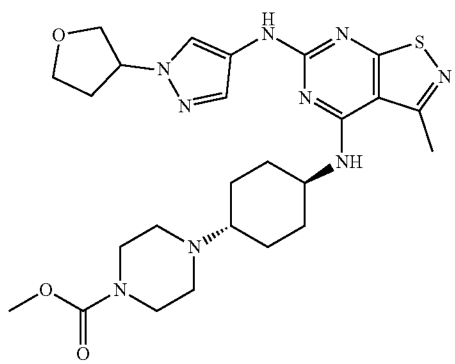 [SMILES: COC(=O)N1CCN([C@H]2CC[C@H](Nc3nc(Nc4cnn(C5CCOC5)c4)nc4snc(C)c34)CC2)CC1] | ¹H NMR (400 MHz, MeOD-d₄) δ = 7.95 (s, 1H), 7.60 (s, 1H), 4.62-4.52 (m, 1H), 4.31-4.48 (m, 1H), 4.14-4.27 (m, 2H), 4.08-4.06 (m, 2H), 3.58 (s, 2H), 3.57 (s, 1H), 3.31-3.30 (m, 1H), 2.69 (s, 4H), 2.34-2.46 (m, 2H), 2.19-2.31 (m, 2H), 2.08-2.06 (m, 4H), 1.68 (s, 2H), 1.50 (s, 4H), 0.50-0.49 (m, 4H), 0.43 (s, 1H) | 542.3 |
| 33 | B22 | B16 | WX033 | 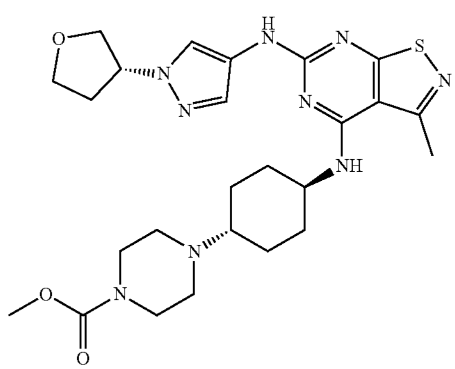 [SMILES: COC(=O)N1CCN([C@H]2CC[C@H](Nc3nc(Nc4cnn([C@@H]5CCOC5)c4)nc4snc(C)c34)CC2)CC1] | ¹H NMR (400 MHz, CDCl₃) δ = 7.93 (s, 1H), 7.56 (s, 1H), 6.84 (s, 1H), 5.20 (s, 1H), 4.98-4.94 (m, 1H), 4.17-4.08 (m, 4H), 3.96-3.94 (m, 1H), 3.72 (s, 3H), 3.50 (s, 4H), 2.69 (s, 3H), 2.56 (s, 4H), 2.46-2.41 (m, 3H), 2.32-2.29 (m, 2H), 1.51-1.45 (m, 2H), 1.32-1.21 (m, 2H) | 542.3 |
| 34 | B22 | B15 | WX034 | 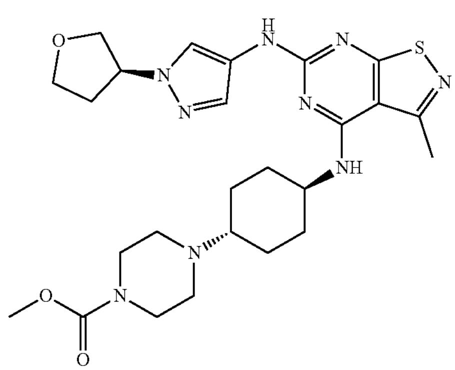 [SMILES: COC(=O)N1CCN([C@H]2CC[C@H](Nc3nc(Nc4cnn([C@H]5CCOC5)c4)nc4snc(C)c34)CC2)CC1] | ¹H NMR (400 MHz, CDCl₃) δ = 7.94 (s, 1H), 7.56 (s, 1H), 6.88 (s, 1H), 5.20 (s, 1H), 4.89-4.93 (m, 1H), 4.16-4.08 (m, 4H), 3.96-3.94 (m, 1H), 3.71 (s, 3H), 3.49 (s, 4H), 2.69 (3, 3H), 2.56-2.55 (m, 4H), 2.46-2.29 (m, 5H), 1.99-1.97 (m, 2H), 1.46-1.16 (m, 4H) | 542.3 |

| Examples | Fragment 1 | Fragment 2 | Compound | Structure | NMR | MS m/z [M + H]+ |
|---|---|---|---|---|---|---|
| 35 | B22 | B3 | WX035 | 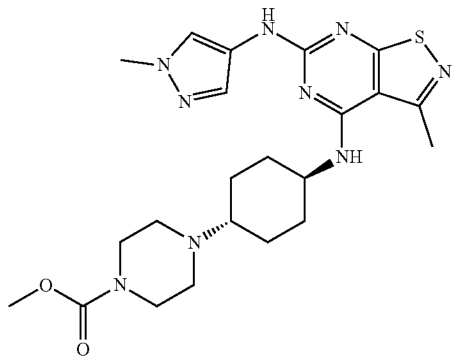 [SMILES: COC(=O)N1CCN([C@H]2CC[C@H](Nc3nc(Nc4cnn(C)c4)nc4snc(C)c34)CC2)CC1] | ¹H NMR (400 MHz, DMSO-d₆) δ = 9.41-9.28 (m, 1H), 7.93-7.77 (m, 1H), 7.48 (s, 1H), 6.36-6.16 (m, 1H), 4.06 (s, 2H), 3.80 (s, 3H), 3.63-3.56 (m, 3H), 3.36-3.28 (m, 4H), 2.67 (s, 3H), 2.35-2.28 (m,. 2H), 2.10 (s, 2H), 1.87 (s, 2H), 1.54-1.48 (m, 3H), 1.39-1.33 (m, 3H) | 486.3 |
| 36 | B28 | B2 | WX036 | 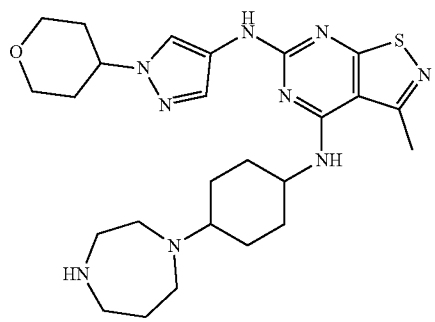 [SMILES: Cc1nsc2nc(Nc3cnn(C4CCOCC4)c3)nc(NC3CCC(N4CCCNCC4)CC3)c12] | ¹H NMR (400 MHz, DMSO-d₆) δ ppm 9.45-9.29 (m, 1H), 8.02-7.93 (m, 1H), 7.52-7.48 (m, 1H), 6.34-6.16 (m, 1H), 4.38-4.34 (m, 1H). 4.06-3.96 (m, 3H), 3.47-3.41 (m, 3H), 2.79-2.68 (m, 8H), 2.10-1.82 (m, 10H), 1.63-1.41 (m, 8H) | 512.4 |
| 37 | B28 | B2 | WX037 | 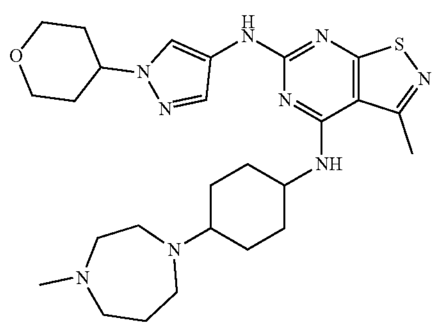 [SMILES: Cc1nsc2nc(Nc3cnn(C4CCOCC4)c3)nc(NC3CCC(N4CCCN(C)CC4)CC3)c12] | ¹H NMR (400 MHz, DMSO-d₆) δ = 12.08-11.92 (m, 1H), 9.55-9.50 (m, 1H), 7.92 (s, 1H), 7.58-7.55 (s, 1H), 6.54-6.43 (m, 1H), 4.42 (s, 1H), 4.41 (s, 1H), 4.00-3.97 (m, 3H), 3.54-3.51 (m, 5H), 3.49-3.48 (m, 1H), 2.81 (s, 3H), 2.71 (s, 3H), 2.53 (s, 3H), 2.32-2.23 (m, 6H), 1.99-1.98 (m, 4H), 1.70-1.67 (m, 4H) | 526.4 |
| 38 | B28 | B2 | WX038 | 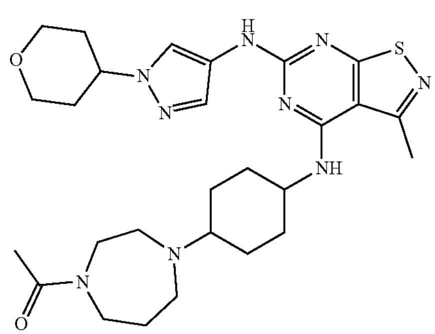 [SMILES: CC(=O)N1CCCN(C2CCC(Nc3nc(Nc4cnn(C5CCOCC5)c4)nc4snc(C)c34)CC2)CC1] | ¹H NMR (400 MHz, DMSO-d₆) δ = 9.47-9.30 (m, 1H), 8.02-7.91 (m, 1H), 7.54-7.50 (s, 1H), 6.26 (s, 1H), 4.39-4.37 (m, 1H), 3.99-3.96 (m, 3H), 3.48-3.42 (m, 6H), 2.79-2.69 (m, 7H), 2.13-2.11 (m, 2H), 1.99-1.85 (m, 12H), 1.56-1.50 (m, 4H) | 554.4 |

-continued

| Examples | Fragment 1 | Fragment 2 | Compound | Structure | NMR | MS m/z [M + H]+ |
|---|---|---|---|---|---|---|
| 39 | B28 | B2 | WX039 | 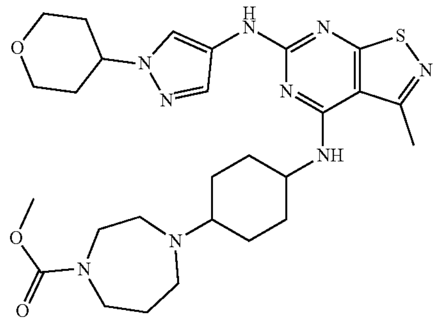 [SMILES: COC(=O)N1CCCN(C2CCC(Nc3nc(Nc4cnn(C5CCOCC5)c4)nc4snc(C)c34)CC2)CC1] | 1H NMR (400 MHz, DMSO-d6) δ = 9.47-9.38 (m, 1H), 8.04-8.01 (m, 1H), 7.87-7.56 (s, 1H), 6.32-6.01 (m, 1H), 4.37-4.29 (d, 2H), 3.99-3.96 (m, 2H), 3.59 (s, 3H), 3.50-3.41 (m, 6H), 2.78-2.63 (m, 7H), 2.07-1.96 (m, 7H), 1.82-1.40 (m, 8H) | 570.3 |
| 40 | B29A | B2 | WX040 | 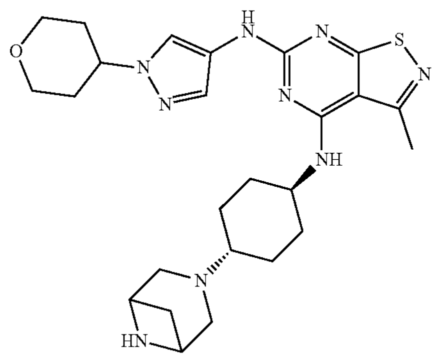 [SMILES: Cc1nsc2nc(Nc3cnn(C4CCOCC4)c3)nc(N[C@H]3CC[C@H](N4CC5CC(C4)N5)CC3)c12] | 1H NMR (400 MHz, MeOD-d4) δ = 8.03 (s, 2H), 7.77-7.63 (m, 2H), 4.60-4.53 (m, 2H), 4.51-4.35 (m, 1H), 4.24-4.03 (m, 7H), 3.77-3.55 (m, 3H), 3.16-3.07 (m, 1H), 2.83 (s, 3H), 2.74-2.66 (m, 1H), 2.51-2.41 (m, 2H), 2.40-2.30 (m, 2H), 2.17-2.04 (m, 5H), 2.04-1.89 (m, 2H), 1.87-1.71 (m, 2H) | 510.4 |
| 41 | B29A | B2 | WX041 | 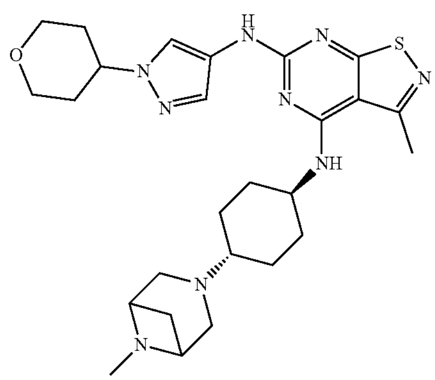 [SMILES: Cc1nsc2nc(Nc3cnn(C4CCOCC4)c3)nc(N[C@H]3CC[C@H](N4CC5CC(C4)N5C)CC3)c12] | 1H NMR (400 MHz, MeOD-d4) δ = 8.00-7.64 (m, 2H), 4.87 (m, 1H), 4.32 (m, 1H), 4.08-4.06 (m, 3H), 3.19-3.16 (m, 3H), 2.71-2.66 (m, 6H), 2.16-2.04 (m, 14H), 1.58-1.56 (m, 5H). | 524.3 |
| 42 | B29B | B2 | WX042 | 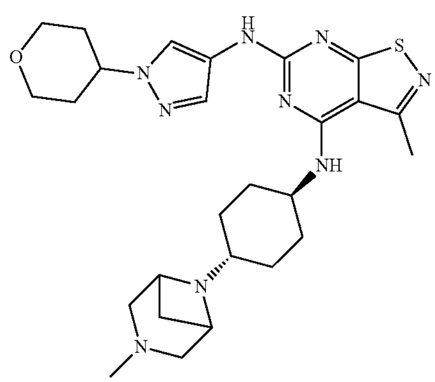 [SMILES: Cc1nsc2nc(Nc3cnn(C4CCOCC4)c3)nc(N[C@H]3CC[C@H](N4C5CC4CN(C)C5)CC3)c12] | 1H NMR (400 MHz, MeOD-d4) δ = 8.09 (s, 1H), 7.89-7.67 (m, 1H), 4.80-4.70 (m, 2H), 4.63-4.46 (m, 3H), 4.28-4.20 (m, 1H), 4.13-4.03 (m, 3H), 4.00-3.91 (m, 1H), 3.66-3.46 (m, 3H), 3.22 (s, 3H), 2.98 (s, 3H), 2.59-2.51 (m, 1H), 2.50-2.41 (m, 1H), 2.20-1.87 (m, 12H). | 524.1 |

-continued
| Examples | Fragment 1 | Fragment 2 | Compound | Structure | NMR | MS m/z [M + H]+ |
|---|---|---|---|---|---|---|
| 43 | B29A | B2 | WX043 | 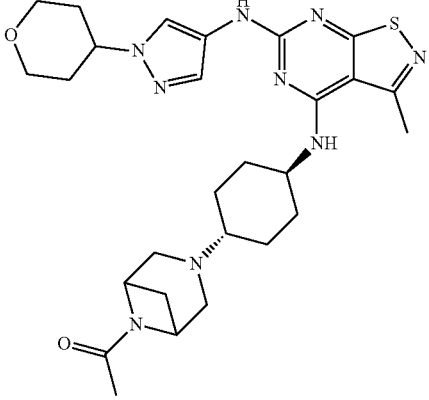 | $^1$H NMR (400 MHz, DMSO-d$_6$) δ = 9.46-9.44 (m, 1H), 7.88-7.86 (m, 1H), 7.51 (s, 1H), 6.38-6.17 (m, 1H), 4.34 (s, 2H), 4.16-4.10 (m, 2H), 3.97-3.94 (m, 2H), 3.43-3.26 (m, 2H), 2.98-2.96 (m, 3H), 2.68-2.66 (m, 1H), 2.5 (s, 3H), 2.40-2.35 (m, 2H), 2.33-1.93 (m, 8H), 1.84 (s, 4H), 1.57-1.40 (m, 4H). | 552.4 |
| 44 | B29A | B2 | WX044 | 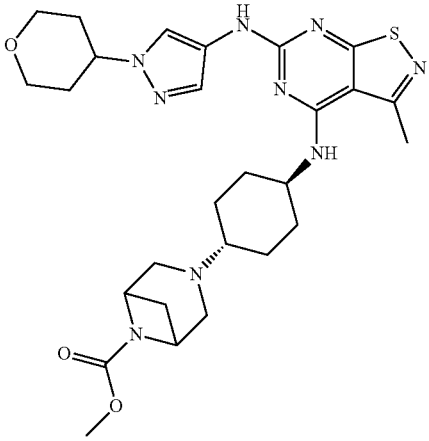 [SMILES: COC(=O)N1C2CC1CN([C@H]1CC[C@H](Nc3nc(Nc4cnn(C5CCOCC5)c4)nc4snc(C)c34)CC1)C2] | $^1$H NMR (400 MHz, MeOD-d$_4$) δ = 8.07-7.90 (m, 1H), 7.87-7.61 (m, 1H), 4.57-4.28 (m, 4H), 4.22-4.02 (m, 2H), 3.84-3.53 (m, 10H), 2.82 (s, 4H), 2.34 (s, 4H), 2.21-1.99 (m, 5H), 1.91-1.68 (m, 4H). | 568.0 |
| 45 | B32 | B2 | WX045 | 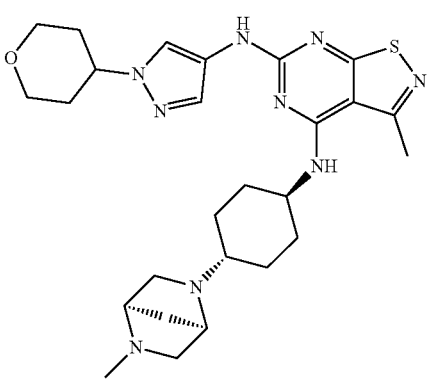 [SMILES: Cc1nsc2nc(Nc3cnn(C4CCOCC4)c3)nc(N[C@H]3CC[C@H](N4C[C@H]5C[C@@H]4CN5C)CC3)c12] | $^1$H NMR (400 MHz, MeOD-d$_4$) δ = 8.10-7.63 (m, 2H), 5.14-5.13 (m, 1H), 4.94-4.93 (m, 1H), 4.58-4.46 (m, 4H), 4.10-4.04 (m, 3H), 3.92-3.56 (m, 6H), 3.32-3.31 (m, 2H), 3.09-3.06 (m, 2H), 2.82 (s, 2H), 2.52-2.50 (m, 2H), 2.30 (s, 3H), 2.13-2.05 (m, 4H), 1.93-1.86 (m, 3H). | 524.3 |

-continued

| Examples | Fragment 1 | Fragment 2 | Compound | Structure | NMR | MS m/z [M + H]+ |
|---|---|---|---|---|---|---|
| 46 | B32 | B2 | WX046 | 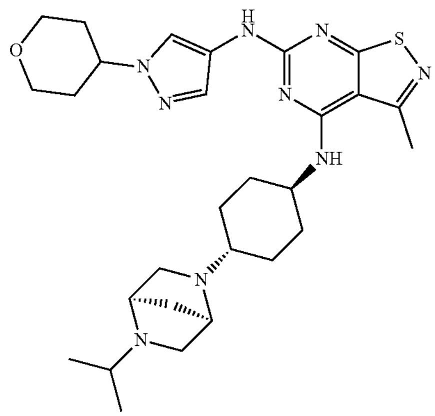 [SMILES: Cc1nsc2nc(Nc3cnn(C4CCOCC4)c3)nc(N[C@H]3CC[C@H](N4C[C@H]5C[C@@H]4CN5C(C)C)CC3)c12] | ¹H NMR (400 MHz, MeOD-d₄) δ = 8.12-7.54 (m, 2H), 4.50-3.91 (m, 5H), 3.67-3.61 (m, 3H), 2.92-2.63 (m, 10H), 2.59-2.39 (m, 1H), 2.30-1.91 (m, 10H), 1.85-1.73 (m, 3H), 1.62-1.30 (m, 5H). | 551.7 |
| 47 | B32 | B2 | WX047 | 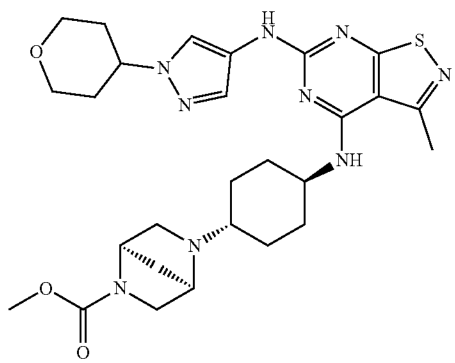 [SMILES: COC(=O)N1C[C@H]2C[C@@H]1CN2[C@H]1CC[C@H](Nc2nc(Nc3cnn(C4CCOCC4)c3)nc3snc(C)c23)CC1] | ¹H NMR (400 MHz, MeOD-d₄) δ = 8.07-7.58 (m, 2H), 4.78-4.61 (m, 2H), 4.58-4.36 (m, 1H), 4.14-4.03 (m, 2H), 3.81-3.48 (m, 10H), 3.44-3.34 (m, 1H), 2.83-2.77 (m, 3H), 2.38-2.16 (m, 6H), 2.14-2.02 (m, 5H), 1.82-1.68 (m, 5H). | 568.3 |
| 48 | B24 | B2 | WX048 | 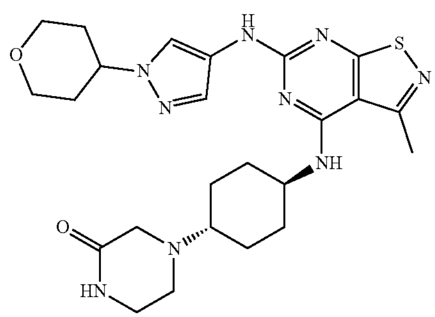 [SMILES: Cc1nsc2nc(Nc3cnn(C4CCOCC4)c3)nc(N[C@H]3CC[C@H](N4CCNC(=O)C4)CC3)c12] | ¹H NMR (400 MHz, DMSO-d₆) δ = 9.48-9.29 (m, 1H) 8.10-7.82 (m, 1H), 7.79-7.73 (m, 1H), 7.62-7.49 (m, 1H), 6.39-6.03 (m, 1H), 4.43-4.32 (m, 1H), 4.31-4.23 (m, 1H), 4.02-3.90 (m, 2H), 3.53-3.41 (m, 2H), 3.32-3.28 (m, 1H), 3.22-3.11 (m, 2H), 3.07-2.98 (m, 2H), 2.78-2.70 (m, 3H), 2.67-2.62 (m, 2H), 2.39-2.28 (m, 2H), 1.99-1.90 (m, 4H), 1.84-1.66 (m, 4H), 1.65-1.50 (m, 2H) | 512.3 |
| 49 | B25 | B2 | WX049 | 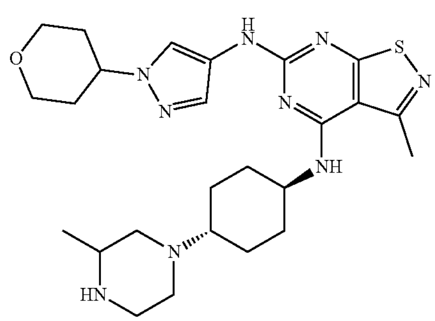 [SMILES: Cc1nsc2nc(Nc3cnn(C4CCOCC4)c3)nc(N[C@H]3CC[C@H](N4CCNC(C)C4)CC3)c12] | ¹H NMR (400 MHz, MeOD-d₄) δ = 8.01 (s, 1H), 7.86-7.63 (m, 1H), 4.62-4.24 (m, 2H), 4.15-4.04 (m, 2H), 4.01-3.84 (m, 4H), 3.83-3.36 (m, 7H), 2.81 (s, 3H), 2.49-2.29 (m, 4H), 2.18-2.06 (m, 4H), 1.93-1.76 (m, 4H), 1.53-1.45 (m, 3H). | 512.4 |

| Examples | Fragment 1 | Fragment 2 | Compound | Structure | NMR | MS m/z [M + H]+ |
|---|---|---|---|---|---|---|
| 50 | B26 | B2 | WX050 | 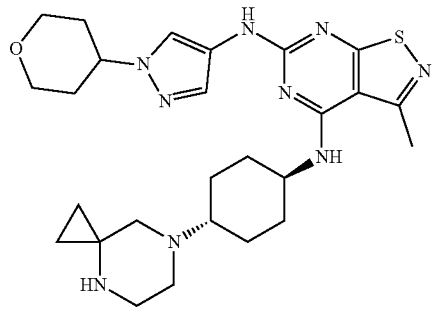 [SMILES: Cc1nsc2nc(Nc3cnn(C4CCOCC4)c3)nc(N[C@H]3CC[C@H](N4CCNC5(CC5)C4)CC3)c12] | ¹H NMR (400 MHz, DMSO-d₆) δ = 9.42 (s, 1H), 7.89 (s, 1H), 7.50 (s, 1H), 6.33 (s, 1H), 4.44 (s, 1H), 4.13-3.91 (m, 3H), 3.48-3.39 (m, 2H), 2.75-2.61 (m, 6H), 2.35-2.19 (m, 4H), 2.16-1.81 (m, 9H), 1.57-1.27 (m, 4H), 0.41-0.32 (m, 4H). | 524.4 |
| 51 | B27 | B2 | WX051 | 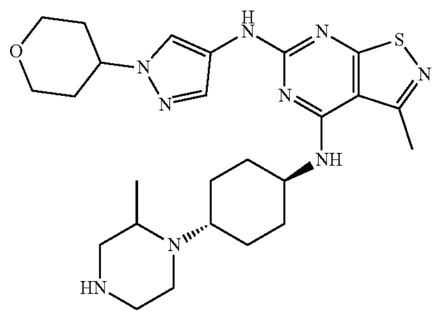 [SMILES: Cc1nsc2nc(Nc3cnn(C4CCOCC4)c3)nc(N[C@H]3CC[C@H](N4CCNCC4C)CC3)c12] | ¹H NMR (400 MHz, DMSO-d₆) δ = 9.96 (s, 1H), 9.56 (s, 1H), 7.94-7.90 (m, 1H), 7.54-7.50 (m, 1H), 6.67 (s, 1H), 4.38 (s, 1H), 4.09 (s, 1H), 3.94 (s, 2H), 3.61 (s, 2H), 3.52-3.43 (m, 4H), 2.68 (s, 2H), 2.64 (s, 1H), 2.49-2.47 (m, 7H), 2.20-2.30 (m, 4H), 1.93-1.91 (m, 2H), 1.73 (m, 2H), 1.57-1.41 (m, 2H), 1.21 (s, 2H) | 512.4 |
| 52 | B30 | B2 | WX052 | 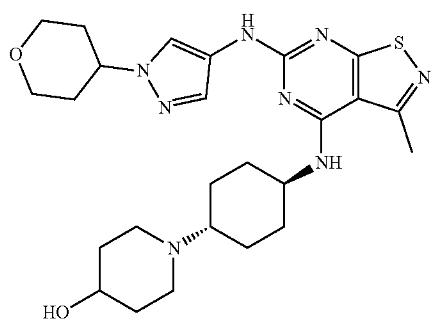 [SMILES: Cc1nsc2nc(Nc3cnn(C4CCOCC4)c3)nc(N[C@H]3CC[C@H](N4CCC(O)CC4)CC3)c12] | ¹H NMR (400 MHz, DMSO-d₆) δ = 8.02-7.58 (m, 2H), 4.44-4.42 (m, 1H), 4.25 (s, 1H), 4.24-4.23 (m, 3H), 3.64-3.57 (m, 2H), 3.47-3.42 (m, 3H), 2.73 (s, 3H), 2.27 (s, 2H), 2.24 (d, 3H), 2.12-2.07 (m, 8H), 1.79-1.62 (m, 8H) | 513.3 |
| 54 | B31 | B2 | WX054 | 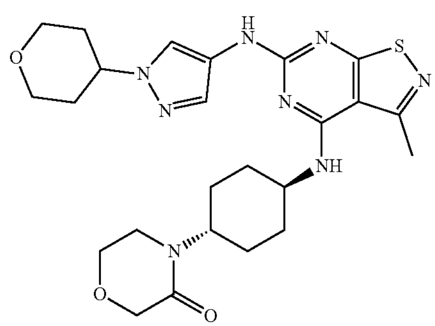 [SMILES: Cc1nsc2nc(Nc3cnn(C4CCOCC4)c3)nc(N[C@H]3CC[C@H](N4CCOCC4=O)CC3)c12] | ¹H NMR (400 MHz, CDCl₃) = 8.06-7.94 (m, 1H), 7.53 (s, 1H), 6.77 (s, 1H), 5.21 (s, 1H), 4.60 (s, 1H), 4.57 (s, 1H), 4.21 (s, 2H), 4.14-4.11 (m, 3H), 3.92-3.90 (m, 2H), 3.59-3.53 (m, 2H), 3.36-3.33 (m, 2H), 2.71 (s, 3H), 2.35-2.33 (m, 2H), 2.13 (m, 4H), 1.86-1.73 (m, 2H), 1.69-1.57 (m, 2H), 1.51-1.48 (m, 2H) | 513.3 |

| Examples | Fragment 1 | Fragment 2 | Compound | Structure | NMR | MS m/z [M + H]+ |
|---|---|---|---|---|---|---|
| 57 | B33 | B2 | WX057 | 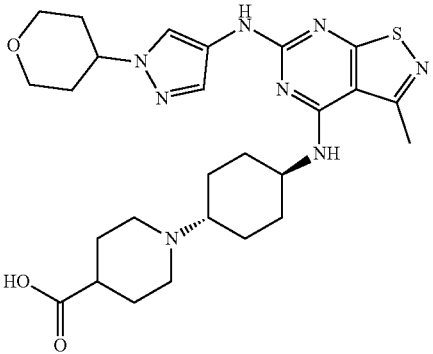 [SMILES: Cc1nsc2nc(Nc3cnn(C4CCOCC4)c3)nc(N[C@H]3CC[C@H](N4CCC(C(=O)O)CC4)CC3)c12] | $^1$H NMR (400 MHz, DMSO-d$_6$) δ = 9.26-9.51 (m, 1H), 7.87-8.06 (m, 1H), 7.42-7.56 (m, 1H), 6.14-6.42 (m, 1H), 4.30-4.44 (m, 1H), 4.01-4.14 (m, 1H), 3.90-4.00 (m, 2H), 3.40-3.48 (m, 2H), 2.75-2.87 (m, 2H), 2.65-2.72 (m, 3H), 2.30-2.40 (m, 2H), 2.20-2.30 (m, 2H), 2.02-2.18 (m, 3H), 1.90-2.00 (m, 4H), 1.73-1.88 (m, 4H), 1.32-1.59 (m, 6H) | 541.3 |
| 58 | B34 | B2 | WX058 | 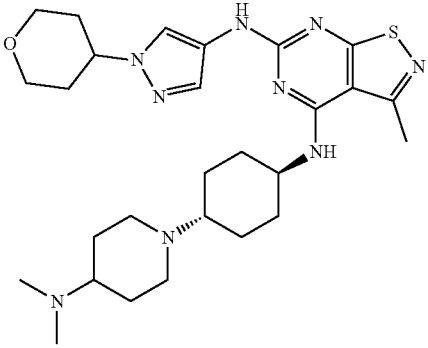 [SMILES: Cc1nsc2nc(Nc3cnn(C4CCOCC4)c3)nc(N[C@H]3CC[C@H](N4CCC(N(C)C)CC4)CC3)c12] | $^1$H NMR (400 MHz, DMSO-d$_6$) δ = 9.28-9.46 (m, 1H), 7.85-7.95 (m, 1H), 7.46-7.54 (m, 1H), 6.17-6.36 (m, 1H), 4.30-4.42 (m, 1H), 4.01-4.12 (m, 1H), 3.92-4.00 (m, 2H), 3.39-3.49 (m, 2H), 2.81-2.91 (m, 2H), 2.73-2.79 (m, 1H), 2.62-2.72 (m, 3H), 2.27-2.38 (m, 1H), 2.10-2.21 (m, 8H), 1.90-2.04 (m, 6H), 1.80-1.89 (m, 2H), 1.68-1.76 (m, 2H), 1.43-1.60 (m, 3H), 1.24-1.37 (m, 3H) | 540.3 |
| 59 | B35 | WX025-1 | WX059 | 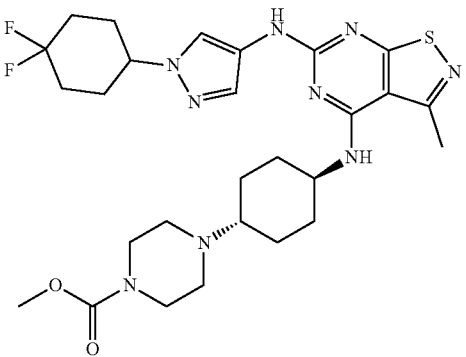 [SMILES: COC(=O)N1CCN([C@H]2CC[C@H](Nc3nc(Nc4cnn(C5CCC(F)(F)CC5)c4)nc4snc(C)c34)CC2)CC1] | $^1$H NMR (400 MHz, CDCl$_3$) δ = ppm 7.97 (s, 1H), 7.54 (s, 1H), 6.79 (s, 1H), 5.19 (s, 1H), 4.27-4.24 (m, 1H), 4.10-4.06 (m, 1H), 3.72 (s, 3H), 3.50 (m, 4H), 2.70 (s, 3H), 2.56 (m, 4H), 2.43-2.37 (m, 1H), 2.32-2.14 (m, 8H), 2.01-1.88 (m, 4H), 1.52-1.43 (m, 2H), 1.35-1.26 (m, 2H). | 590.3 |

Example 60: Synthesis of Compound WX060

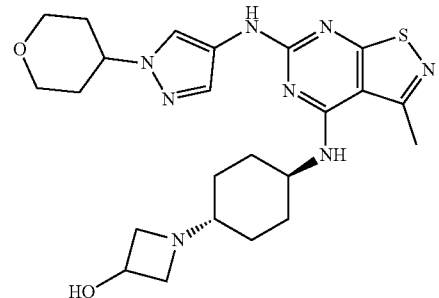 [SMILES: Cc1nsc2nc(Nc3cnn(C4CCOCC4)c3)nc(N[C@H]3CC[C@H](N4CC(O)C4)CC3)c12]

Synthetic route:

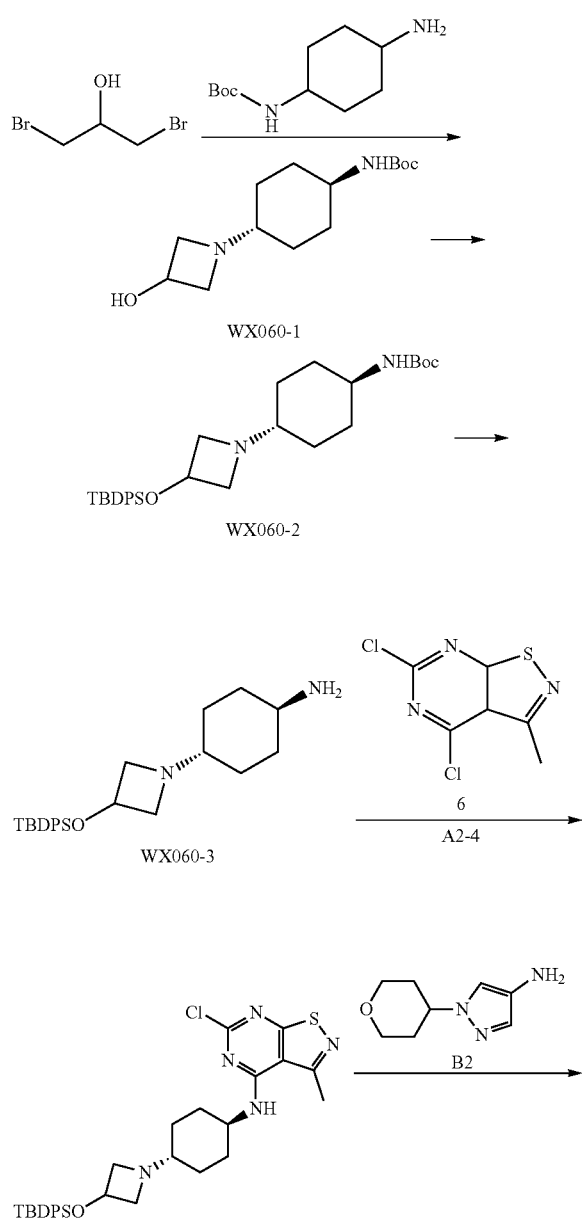

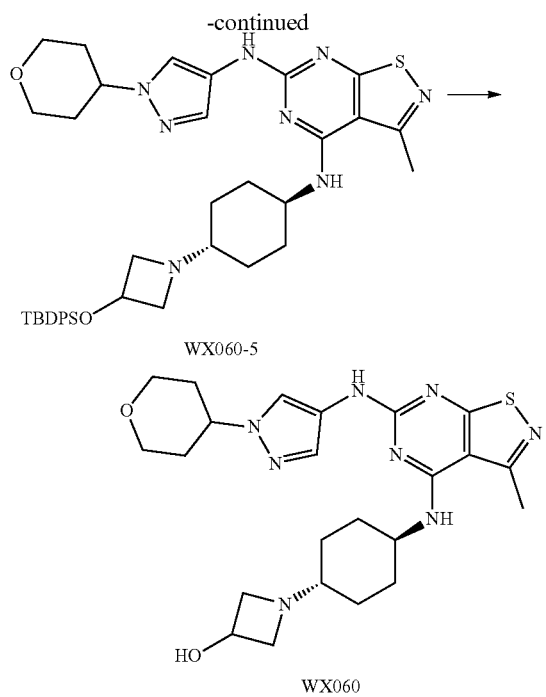

Step 1: Synthesis of Compound WX060-1

1,3-dibromo-2-propanol (5 g), N-Boc-1,4-cyclohexanediamine (4.47 g), and sodium carbonate (19.90 g) were mixed in a flask containing ethanol (300 mL), and the mixture was stirred at 80° C. for 12 hours. The solvent in the mixture was completely removed under reduced pressure. The crude product was slurried using ethyl acetate (100 mL) and filtered. The solvent in the filtrate was completely removed under reduced pressure to give compound WX060-1.

Step 2: Synthesis of Compound WX060-2

Compound WX060-1 (8 g) was dissolved in N,N-dimethylformamide (100 mL) at 0° C. and then t-butyldiphenylchlorosilane (6.31 g) and imidazole (3.44 g) were added. The mixture was incubated at 25° C. for 4 hours. The resulting mixture was filtered, and 200 mL of water was added to the filtrate, followed by extraction with ethyl acetate (150 mL×4). The organic phases were combined and dehydrated using an appropriate amount of anhydrous sodium sulfate. The dehydrated organic phase was filtered to remove the desiccant, and the solvent in the filtrate was completely removed under reduced pressure to give a crude product. The crude product was separated using an automated chromatographic system COMBI-FLASH (Sepa-Flash® Silica Flash Column, mobile phase: 0-80% petroleum ether/ethyl acetate, flow rate: 80 mL/min), and purified to give compound WX060-2.

Step 3: Synthesis of Compound WX060-3

Compound WX060-2 (1 g) was dissolved in dichloromethane (10 mL) at 0° C. and added with trifluoroacetic acid (2 mL). After 1 hour of incubation, additional trifluoroacetic acid (2 mL) was added and the reaction system was incubated for another 2 hours. After that, 30 mL of water was added to the reaction system, and the mixture was added with ethyl acetate (4×20 mL) for extraction. The organic phases were combined and dehydrated using an appropriate amount of anhydrous sodium sulfate. The dehydrated organic phase was filtered to remove the desiccant, and the solvent in the filtrate was completely removed under reduced pressure to give a crude product. The crude product was separated using an automated chromatographic system COMBI-FLASH (SepaFlash® silicon FLASH Column, mobile phase: 0-7% dichloromethane/methanol-petroleum ether/ethyl acetate, flow rate: 80 mL/min) to give compound WX060-3. LCMS (ESI) m/z: 409.1 [M+H]$^+$ Step 4: Synthesis of Compound WX060-4

Referring to intermediate A2 synthesis, the compound WX060-4 was synthesized starting with intermediate A2-4 and compound WX060-3.

Step 5: Synthesis of Compound WX060-5

Referring to WX001 synthesis, the compound WX060-5 was synthesized starting with compound WX060-4 and intermediate B2.

Step 6: Synthesis of Compound WX060

Compound WX060-5 (0.03 g) was dissolved in anhydrous tetrahydrofuran (2 mL), and added with a solution of tetrabutylammonium fluoride in tetrahydrofuran (1 M, 82.99 μL). The reaction system was incubated at 15° C. for 12 hours in nitrogen atmosphere. The solvent was completely removed under reduced pressure and the crude product was separated by HPLC (column: Welch XTimate C18 150×25 mm×5 μm; mobile phase: A: 10 mM aqueous NH$_4$HCO$_3$, B: acetonitrile; gradient: B %: 20%-50%, 10.5 min) to give compound WX060. LCMS (ESI) m/z: 485.3 [M+1]+. $^1$H NMR (400 MHz, DMSO-d$_6$) δ=9.48-9.36 (m, 1H), 8.10-7.81 (m, 1H), 7.63 (s, 1H), 6.48-6.43 (m, 1H), 5.29 (d, J=6.8 Hz, 1H), 4.41-4.40 (m, 1H), 4.20-4.13 (m, 2H), 4.04-4.01 (m, 2H), 3.56-3.47 (m, 4H), 3.45-3.42 (m, 3H), 2.74 (s, 5H), 2.08-1.97 (m, 6H), 1.88-1.86 (m, 2H), 1.58-1.55 (m, 1H), 1.11-1.10 (m, 1H).

Experimental Example 1: In Vitro Enzymatic Activity Evaluation

The inhibitory activity of the test compounds against human IRAK4 was evaluated by measuring IC$_{50}$ values in a $^{33}$P-labeled kinase activity assay (Reaction Biology Corp).

Buffer conditions: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO.

Procedures: The test compound was dissolved in DMSO at room temperature to prepare a 10 mM solution for later use. The substrate was dissolved in fresh buffer, to which the kinase was added and mixed well. The DMSO solution containing the test compound was added to the above mixed reaction system by an acoustic technique (Echo 550). The concentrations of the compounds in reaction system were 10 μM, 3.33 μM, 1.11 μM, 0.370 μM, 0.123 μM, 41.2 nM, 13.7 nM, 4.57 nM, 1.52 nM, and 0.508 nM. After 15 minutes of incubation, the reaction was started by adding $^{33}$P-ATP (activity: 0.01 μCi/μL; the corresponding concentration is listed in Table 1). Supplier's catalog number, lot number and concentration information in the reaction system for IRAK4 and its substrate are listed in Table 1. After 120 minutes of reaction at room temperature, the resulting solution was loaded on P81 ion exchange chromatography paper sheet (Whatman #3698-915). After repeated washing with 0.75% phosphoric acid solution, the radioactivity of the phosphorylated substrate residue on the paper sheet was measured. The kinase activity data are shown as a comparison of the kinase activity of the test compound and the kinase activity of the blank (DMSO only) and a curve was fitted using Prism4 software (GraphPad) to give IC$_{50}$ values, with the experimental results shown in Table 2.

TABLE 1

Information related to kinases, substrates and ATP in the in vitro assay

| Kinases | Supplier | Cat # | Lot # | Kinase concentration (nM) in reaction system | ATP concentration (μM) |
|---|---|---|---|---|---|
| IRAK4 | Invitrogen | PV3362 | 404828G | 3 | 20 |

| Substrate | Supplier | Cat # | Lot # | Substrate concentration in reaction system (μM) |
|---|---|---|---|---|
| MBP | Active Motif | | 102641 | 04811001 | 20 |

TABLE 2

Results of in vitro kinase activity screening for compounds disclosed herein

| Compound number | IRAK4/IC$_{50}$ (nM) |
|---|---|
| WX001 | 6.8 |
| WX002 | 89.5 |
| WX003 | 2.9 |
| WX005 | 8.7 |
| WX006 | 9.9 |
| WX007 | 5.7 |
| WX008 | 27.2 |
| WX009 | 21.3 |
| WX010 | 45.9 |
| WX011 | 357.0 |
| WX013 | 60.1 |
| WX014 | 30.3 |
| WX015 | 20.5 |
| WX024 | 13.5 |
| WX025 | 23.6 |
| WX026 | 2.0 |
| WX027 | 3.3 |
| WX028 | 1.6 |
| WX029 | 3.8 |
| WX030 | 7.5 |
| WX031 | 2.4 |
| WX032 | 15.2 |
| WX033 | 12.8 |
| WX034 | 12.8 |
| WX035 | 10.7 |
| WX036 | 5.5 |
| WX037 | 9.2 |
| WX038 | 1.3 |
| WX039 | 7.9 |
| WX040 | 30.0 |
| WX041 | 21.4 |
| WX043 | 12.2 |
| WX044 | 40.7 |
| WX045 | 278.0 |
| WX046 | 231.0 |
| WX047 | 29.6 |
| WX048 | 460.0 |
| WX049 | 11.2 |
| WX050 | 13.4 |
| WX051 | 13.7 |

TABLE 2-continued

Results of in vitro kinase activity screening
for compounds disclosed herein

| Compound number | IRAK4/IC$_{50}$ (nM) |
|---|---|
| WX052 | 1.8 |
| WX054 | 363.0 |
| WX055 | 11.7 |
| WX056 | 17.0 |
| WX057 | 5.0 |
| WX058 | 2.1 |
| WX059 | 1.1 |
| WX060 | 7.3 |

Conclusion: The compounds disclosed herein generally exhibit reasonable inhibitory activity against IRAK4.

Liver-to-body weight ratio: 88 g/kg for mice

Clearance in the whole liver was calculated using $CL_{int}^{mic}$:

$$CL_{int(liver)} = CL \cdot \frac{45 \text{ mg} \cdot \text{microsomes}}{\text{g} \cdot \text{liver}} \cdot \frac{\text{g} \cdot \text{liver}}{\text{kg} \cdot \text{body} \cdot \text{weight}}$$

$CL_{int}^{mic}$: intrinsic microsomal clearance;

Microsomal protein in incubation: microsomal protein in incubation;

Microsomes: microsomes;

Liver: liver;

Body weight: body weight

The results are summarized in Table 3.

TABLE 3

Results of liver microsome metabolic assay in vitro for compounds disclosed herein

| Compound number | Human | | Rat | | Dog | | Mouse | | Monkey | |
|---|---|---|---|---|---|---|---|---|---|---|
| | Cl$_{int}$ | Re$_{1\,h}$ % | Cl$_{int}$ | Re$_{1\,h}$ % | Cl$_{int}$ | Re$_{1\,h}$ % | Cl$_{int}$ | Re$_{1\,h}$ % | Cl$_{int}$ | Re$_{1\,h}$ % |
| WXR1 | 44 | 23.7% | 67 | 32.3% | 139 | 5.5% | 3236 | 0.0% | 1237 | 0.6% |
| WX001 | 23 | 50.0% | 18 | 76.6% | 24 | 60.5% | 132 | 39.1% | 160 | 3.2% |

Cl$_{int}$: intrinsic clearance
Re$_{1\,h}$ %: residue of test compound at 1 hour
Conclusion: The representative compounds disclosed herein have impressive advantages over the reference compound (WXR1) in terms of liver microsome stability in multiple species, and particularly in some species (e.g., mice), have a 20-fold superiority in clearance.

Experimental Example 2: In Vitro Stability Assay in Liver Microsome

Metabolic Stability in Liver Microsome

The test compounds at 1 μM were co-incubated with liver microsomes having a protein concentration of 0.5 mg/mL under the action of a reductive coenzyme II regeneration system in a 37° C. water bath.
1) Positive controls included: testosterone (3A4 substrate), propylamine propiophenone (2D6 substrate), and diclofenac (2C9 substrate). The positive controls were incubated in the same condition as the test compounds.
2) The reaction was stopped using a stop reagent containing the internal standard at time points of 0, 5, 10, 20, 30 and 60 minutes. The compounds were co-incubated with the microsomes for 60 minutes in the absence of the reductive coenzyme II regeneration system and served as negative controls.
3) No replicate was set for each time point (n=1).
4) Samples were analyzed by LC/MS/MS and the concentrations are shown as the ratio of compound peak area to internal standard peak area (non-standard curve).
5) In the summary, the half-life and clearance were calculated
6) The following formula was used to calculate the clearance $$C_t = \frac{1}{2}C_0,\ t_{1/2} = \frac{\ln 2}{k} = \frac{0.693}{k}.\ CL_{int}^{mic} = \frac{0.693}{\text{In vitro } T_{\frac{1}{2}}} \cdot \frac{1}{\text{mg/ml microsomal protein in incubation}}$$

Experimental Example 3: In Vitro Activity Assay in Cells

TNF-α ELISA Assay in THP-1 Cells
1. Materials:
THP-1 human acute unicellular leukemia cells were purchased from ATCC (Cat #TIB-202) and incubated in a 37° C., 5% CO$_2$ incubator.
The medium was RPMI1640 (Gibco, Cat #22400-105), the supplementary was 10% FBS (Gibco, Cat #10091148); 1% PenStrep (Gibco, Cat #15140); 0.05 mM 2-mercaptoethanol (Sigma, Cat #M6250).
2. Method:
TNF-α content in the culture supernatant was measured by a TNF-α Elisa kit. TNF-α was produced by stimulation of THP-1 cells with 150 ng/mL LPS (Sigma, Cat #L6529).
Normal THP-1 cells in logarithmic phase were inoculated in 96-well plates (Corning #3599) at a certain concentration (1×10$^5$/100 μL) and then incubated in an incubator. After two hours, 16.7 μL of test compound of different concentrations (8×final concentration) was added and the mixture was incubated. After one hour, 16.7 μL of 1200 ng/mL LPS was added and the mixture was incubated. After 18 hours, the culture was centrifuged and the supernatant was collected. The TNF-α content was measured by a TNF-α Elisa kit. Finally, the OD signals (OD450-OD570) were read on an envision plate reader.
3. Data Analysis:
The OD450-OD570 signals were converted to percent inhibition.

Inhibition %=(ZPE−sample)/(ZPE−HPE)×100.

"HPE" represents the OD450-OD570 signal value of the control without LPS-stimulated cells, and "ZPE" represents the OD450-OD570 signal value of the control with LPS-stimulated cells. $IC_{50}$ values for compounds were calculated by XLFit in the Excel.

Equation: $Y = Bottom + (Top - Bottom)/(1 + (IC_{50}/X)^{HillSlope})$.

The results are summarized in Table 4.

TABLE 4

Results of in vitro screening for compounds disclosed herein

| Compound number | THP-1/$IC_{50}$ (nM) |
|---|---|
| WX001 | 177 |
| WX003 | 329 |
| WX006 | 486 |
| WX007 | 417 |
| WX008 | 279 |
| WX009 | 649 |
| WX014 | 663 |
| WX015 | 952 |
| WX026 | 156 |
| WX027 | 639 |
| WX028 | 234 |
| WX030 | 308 |
| WX031 | 317 |
| WX036 | 4159 |
| WX037 | 296 |
| WX038 | 216 |

TABLE 4-continued

Results of in vitro screening for compounds disclosed herein

| Compound number | THP-1/$IC_{50}$ (nM) |
|---|---|
| WX039 | 139 |
| WX047 | 889 |
| WX049 | 516 |
| WX050 | 689 |
| WX055 | 165 |

Conclusion: The compounds disclosed herein generally exhibit reasonable inhibitory activity on proliferation of THP-1 cells.

Experimental Example 4: Pharmacokinetic Study

Pharmacokinetic Study of Oral and Intravenous Test Compounds in SD Rats

The test compound was mixed with a solution containing 10% of methyl pyrrolidone, 10% of polyethylene glycol stearate and 80% of water. The mixture was vortexed and sonicated to prepare a 1.5 mg/mL clarified solution, which was then filtered through a microporous membrane for later use. SD male rats aged 7 to 10 weeks were selected and administered intravenously with a dose of the candidate compound at 3 mg/kg. The test compound was mixed with 0.5% aqueous methylcellulose solution. The mixture was vortexed and sonicated to prepare a 2 mg/mL suspension for later use. SD male rats aged 7 to 10 weeks were selected and orally administered with a dose of the candidate compound at 10 mg/kg. Whole blood was collected at certain time points, and plasma was separated. The drug concentration was measured by LC-MS/MS, and pharmacokinetic parameters were calculated using Phoenix WinNonlin software (Pharsight, USA). The experimental results are shown in Table 7.

TABLE 7

Pharmacokinetic results of the test compounds

| Route of administration | Pharmacokinetic parameters | WXR2 | WX001 | WX003 | WX007 | WX009 | WX026 |
|---|---|---|---|---|---|---|---|
| Intravenous | Half life $T_{1/2}$ (h) | 1.3 | 1.4 | 1.0 | 0.9 | 1.8 | 2.2 |
| | Clearance CL (mL/min/kg) | 33.2 | 57.0 | 71.4 | 79.0 | 73.3 | 50.6 |
| | Apparent volume of distribution $Vd_{ss}$ (L/kg) | 1.6 | 4.6 | 4.8 | 3.3 | 5.7 | 4.5 |
| | Area under plasma concentration-time curve $AUC_{0-last}$ (nM·h) | 3679 | 1746 | 1326 | 1330 | 1459 | 1773 |
| Oral | Time to peak $T_{max}$ (h) | 0.6 | 2.3 | 0.8 | 2.0 | 2.5 | 1.5 |
| | Peak concentration $C_{max}$ (nM) | 893 | 397 | 523 | 389 | 540 | 308 |
| | Area under plasma concentration-time curve $AUC_{0-last}$ (nM·h) | 2128 | 2052 | 2010 | 1643 | 2694 | 1356 |
| | Bioavailability F (%) | 18% | 35% | 48% | 38% | 58% | 23% |

The results show that: the total systemic exposure, peak concentration and bioavailability of various compounds of this project orally administered were equivalent or superior to the reference compound WXR2 (ND-2110) at the same dose, demonstrating superior pharmacokinetic properties.

Experimental Example 5: Pharmacodynamic Study

Pharmacodynamic Study Evaluating Lipo-Polycollagen (LPS)-Induced TNF-α Secretion in SD Rats
1. Modeling and Administration
SD rats were orally administered with a solvent, dexamethasone (DEX, 0.5 mg/kg) as positive control, and the test compound, and were intraperitoneally injected with LPS (1 mg/kg) 0.5 hours after the administration Animals were euthanized with $CO_2$ 2 hours after LPS injection. Cardiac blood was collected into EDTA-K2 vacutainers, and a part of the anticoagulated blood was centrifuged and the plasma was frozen at −80° C.

2. Assay of TNF-α and Il-1b

Frozen plasma was thawed at room temperature and the concentration of TNF-α in the plasma was measured using ELISA kit.

3. Statistics

The experimental data were expressed using mean±SEM, and TNF-α levels were analyzed by One-way ANOVA. Significant differences were considered for $p<0.05$. The results of pharmacodynamic study evaluating LPS-induced TNF-α secretion in SD rats are shown in FIGS. 1 and 2.

FIG. 1 shows that: at the same doses, oral WX001 exhibited significant inhibitory effect on lipo-polychollagen (LPS)-induced TNF-α secretion, which was significantly superior to the reference compounds WXR2(ND-2110), WXR3(BAY-1830839) and WXR4 (BAY-1834845). In this experiment, the efficacy of WX001 was equivalent to that of dexamethasone DEX.

Figure 2:
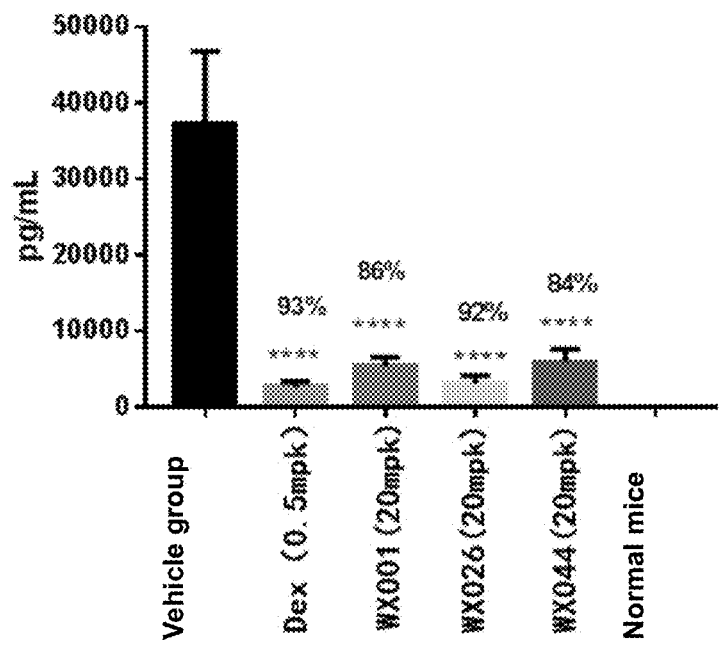
FIG. 2 shows the results of a pharmacodynamic study evaluating lipo-polycollagen (LPS)-induced TNF-α secretion in SD rats with the dose of the compounds being 20 mpk.

FIG. 2 shows that: at the same doses, oral WX001 WX026 and WX044 exhibited significant inhibitory effect on lipo-polychollagen (LPS)-induced TNF-α secretion. In this experiment, the efficacy of WX026 was equivalent to that of dexamethasone DEX.

What is claimed is:

1. A compound of formula (II), an optical isomer or a pharmaceutically acceptable salt thereof,

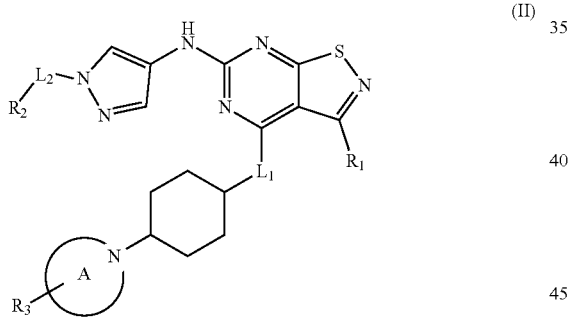

(II)

wherein, $R_1$ is selected from the group consisting of CN, $C_{1-6}$ alkyl and 3-6 membered heterocycloalkyl, wherein the $C_{1-6}$ alkyl and 3-6 membered heterocycloalkyl are optionally substituted with 1, 2 or 3 $R_a$;

$R_2$ is selected from the group consisting of $C_{1-6}$ alkyl and 3-6 membered heterocycloalkyl, wherein the $C_{1-6}$ alkyl and 3-6 membered heterocycloalkyl are optionally substituted with 1, 2 or 3 $R_b$;

$R_3$ is selected from the group consisting of H, F, Cl, Br, I, OH, $NH_2$, CN, $C_{1-6}$ alkyl, —C(=O)—O—$C_{1-6}$ alkyl, —C(=O)—$C_{1-6}$ alkyl and $C_{3-6}$ cycloalkyl, wherein the $C_{1-6}$ alkyl, —C(=O)—O—$C_{1-6}$ alkyl, —C(=O)—$C_{1-6}$ alkyl and $C_{3-6}$ cycloalkyl are optionally substituted with 1, 2 or 3 $R_c$;

ring A is selected from the group consisting of 3-10 membered heterocycloalkyl, and the 3-10 membered heterocycloalkyl is optionally substituted with 1, 2 or 3 $R_d$;

$L_1$ is selected from the group consisting of O and $N(R_4)$;

$L_2$ is selected from the group consisting of a single bond, $CH_2$ and $CH_2CH_2$;

$R_4$ is selected from the group consisting of H and Me;

each $R_a$ is independently selected from the group consisting of F, Cl, Br, I, OH, $NH_2$, CN and COOH;

each $R_b$ is independently selected from the group consisting of F, Cl, Br, I, OH, $NH_2$, COOH and Me;

each $R_c$ is independently selected from the group consisting of F, Cl, Br, I, OH, $NH_2$ and CN;

each $R_d$ is independently selected from the group consisting of F, Cl, Br, I, OH, $NH_2$ and CN;

the 3-6 membered heterocycloalkyl contains 1, 2 or 3 heteroatoms or heteroatom groups independently selected from the group consisting of —O—, —S—, —NH— and N; and the 3-10 membered heterocycloalkyl contains 1, 2 or 3 heteroatoms or heteroatom groups independently selected from the group consisting of —O—, —S—, —NH—, N, and —C(=O)NH—.

2. A compound of formula (III), an optical isomer or a pharmaceutically acceptable salt thereof,

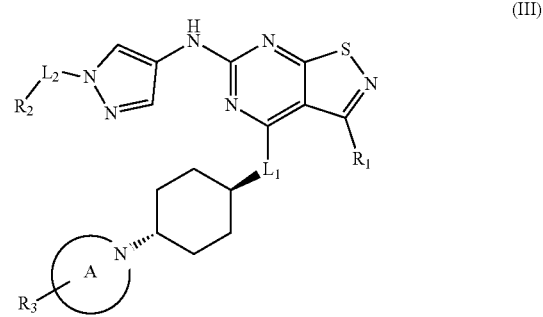

(III)

wherein, $R_1$ is selected from the group consisting of CN, $C_{1-6}$ alkyl and 3-6 membered heterocycloalkyl, wherein the $C_{1-6}$ alkyl and 3-6 membered heterocycloalkyl are optionally substituted with 1, 2 or 3 $R_a$;

$R_2$ is selected from the group consisting of $C_{1-6}$ alkyl, $C_{3-8}$ cycloalkyl and 3-6 membered heterocycloalkyl, wherein the $C_{1-6}$ alkyl, $C_{3-8}$ cycloalkyl and 3-6 membered heterocycloalkyl are optionally substituted with 1, 2 or 3 $R_b$;

$R_3$ is selected from the group consisting of H, F, Cl, Br, I, OH, $NH_2$, CN, COOH, $C_{1-6}$ alkyl, $C_{1-6}$ alkylamino, —C(=O)—O—$C_{1-6}$ alkyl, —C(=O)—$C_{1-6}$ alkyl and $C_{3-6}$ cycloalkyl, wherein the $C_{1-6}$ alkyl, $C_{1-6}$ alkylamino, —C(=O)—O—$C_{1-6}$ alkyl, —C(=O)—$C_{1-6}$ alkyl and $C_{3-6}$ cycloalkyl are optionally substituted with 1, 2 or 3 $R_c$;

ring A is selected from the group consisting of 3-10 membered heterocycloalkyl, and the 3-10 membered heterocycloalkyl is optionally substituted with 1, 2 or 3 $R_d$;

$L_1$ is selected from the group consisting of O and N ($R_4$);

$L_2$ is selected from the group consisting of a single bond, $CH_2$ and $CH_2CH_2$;

$R_4$ is selected from the group consisting of H and Me;

each $R_a$ is independently selected from the group consisting of F, Cl, Br, I, OH, $NH_2$, CN and COOH;

each $R_b$ is independently selected from the group consisting of F, Cl, Br, I, OH, $NH_2$, COOH and Me;

each $R_c$ is independently selected from the group consisting of F, Cl, Br, I, OH, $NH_2$ and CN;
each $R_d$ is independently selected from the group consisting of H, F, Cl, Br, I, OH, $NH_2$ and CN;
the 3-6 membered heterocycloalkyl contains 1, 2 or 3 heteroatoms or heteroatom groups independently selected from the group consisting of —O—, —S—, —NH— and N; and
the 3-10 membered heterocycloalkyl contains 1, 2 or 3 heteroatoms or heteroatom groups independently selected from the group consisting of —O—, —S—, —NH—, N, and —C(=O)NH—.

3. The compound, the optical isomer or the pharmaceutically acceptable salt thereof according to claim 2, wherein $R_1$ is selected from the group consisting of $C_{1-3}$ alkyl and tetrahydropyranyl, wherein the $C_{1-3}$ alkyl and tetrahydropyranyl are optionally substituted with 1, 2 or 3 $R_a$.

4. The compound, the optical isomer or the pharmaceutically acceptable salt thereof according to claim 3, wherein $R_1$ is selected from the group consisting of Me, Et,

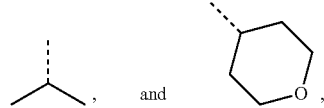

wherein the Me, Et,

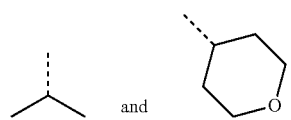

are optionally substituted with 1, 2 or 3 $R_a$.

5. The compound, the optical isomer or the pharmaceutically acceptable salt thereof according to claim 4, wherein $R_1$ is selected from the group consisting of Me, Et,

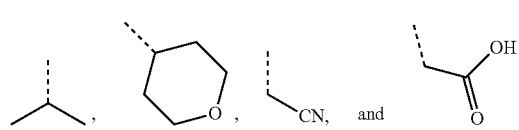

6. The compound, the optical isomer or the pharmaceutically acceptable salt thereof according to claim 2, wherein $R_2$ is selected from the group consisting of $C_{1-3}$ alkyl, $C_{4-6}$ cycloalkyl, tetrahydropyranyl, oxetanyl, tetrahydrofuranyl and 1,4-dioxanyl, wherein the $C_{1-3}$ alkyl, $C_{4-6}$ cycloalkyl, tetrahydropyranyl, oxetanyl, tetrahydrofuranyl and 1,4-dioxanyl are optionally substituted with 1, 2 or 3 $R_b$.

7. The compound, the optical isomer or the pharmaceutically acceptable salt thereof according to claim 6, wherein $R_2$ is selected from the group consisting of Me, Et,

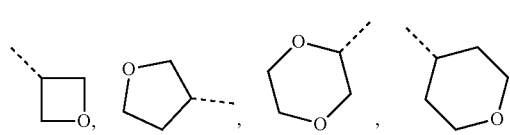

and cyclohexyl, wherein Me, Et,

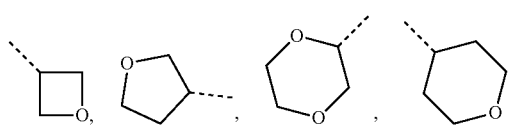

and cyclohexyl are optionally substituted with 1, 2, or 3 $R_b$.

8. The compound, the optical isomer or the pharmaceutically acceptable salt thereof according to claim 7, wherein $R_2$ is selected from the group consisting of Me, —$CH_2OH$, Et,

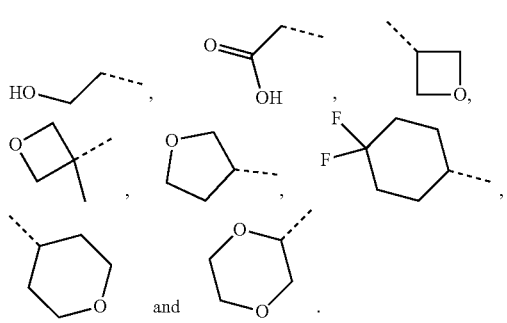

9. The compound, the optical isomer or the pharmaceutically acceptable salt thereof according to claim 1, wherein the structural unit

is selected from the group consisting of Me, Et,

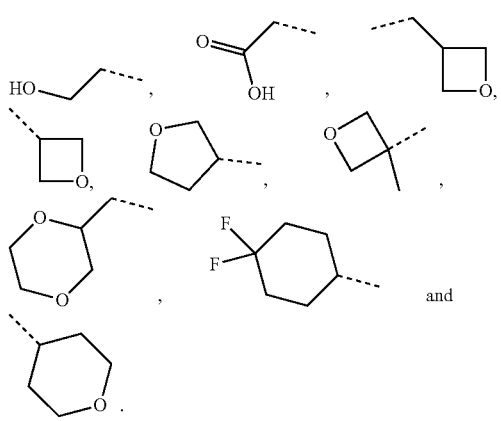

10. The compound, the optical isomer or the pharmaceutically acceptable salt thereof according to claim 2, wherein $R_3$ is selected from the group consisting of H, F, Cl, Br, I, OH, $NH_2$, CN, COOH, $C_{1-3}$ alkyl, —$N(C_{1-3}$ alkyl$)_2$, —C(=O)—O—$C_{1-3}$ alkyl, —C(=O)—$C_{1-3}$ alkyl and $C_{3-6}$ cycloalkyl, wherein the $C_{1-3}$ alkyl, —$N(C_{1-3}$ alkyl$)_2$, —C(=O)—O—$C_{1-3}$ alkyl, —C(=O)—$C_{1-3}$ alkyl and $C_{3-6}$ cycloalkyl are optionally substituted with 1, 2 or 3 $R_c$.

11. The compound, the optical isomer or the pharmaceutically acceptable salt thereof according to claim 10, wherein $R_3$ is selected from the group consisting of H, F, Cl, Br, I, OH, $NH_2$, CN, COOH, Me, Et,

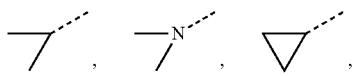

—C(=O)—O-Me, —C(=O)—O-Et and —C(=O)-Me.

12. The compound, the optical isomer or the pharmaceutically acceptable salt thereof according to claim 2, wherein ring A is selected from the group consisting of morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl, 2,5-diazabicyclo[2.2.1]heptyl and azetidinyl, wherein the morpholinyl, piperazinyl, 3-morpholinonyl, 2-piperazinonyl, homopiperazinyl, 4,7-diazaspiro[2,5]octyl, 3,6-diazabicyclo[3,1,1]heptyl, 2-azacyclohexanonyl, 2,5-diazabicyclo[2.2.1]heptyl and azetidinyl are optionally substituted with 1, 2, or 3 $R_d$.

13. The compound, the optical isomer or the pharmaceutically acceptable salt thereof according to claim 12, wherein ring A is selected from the group consisting of

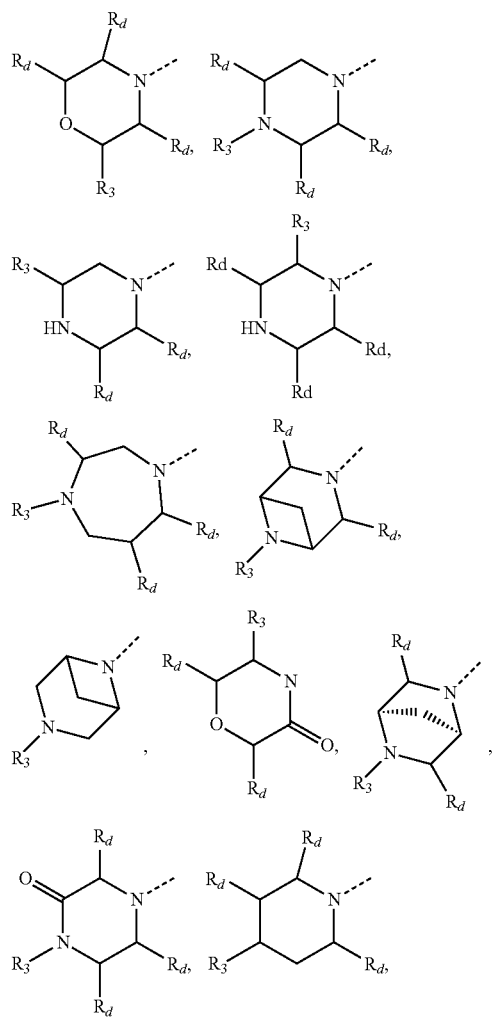

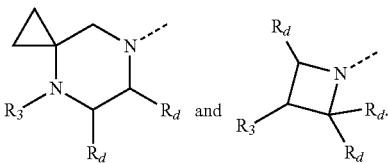

14. The compound, the optical isomer or the pharmaceutically acceptable salt thereof according to claim 13, wherein the structural unit

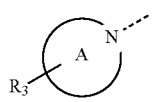

is selected from the group consisting of

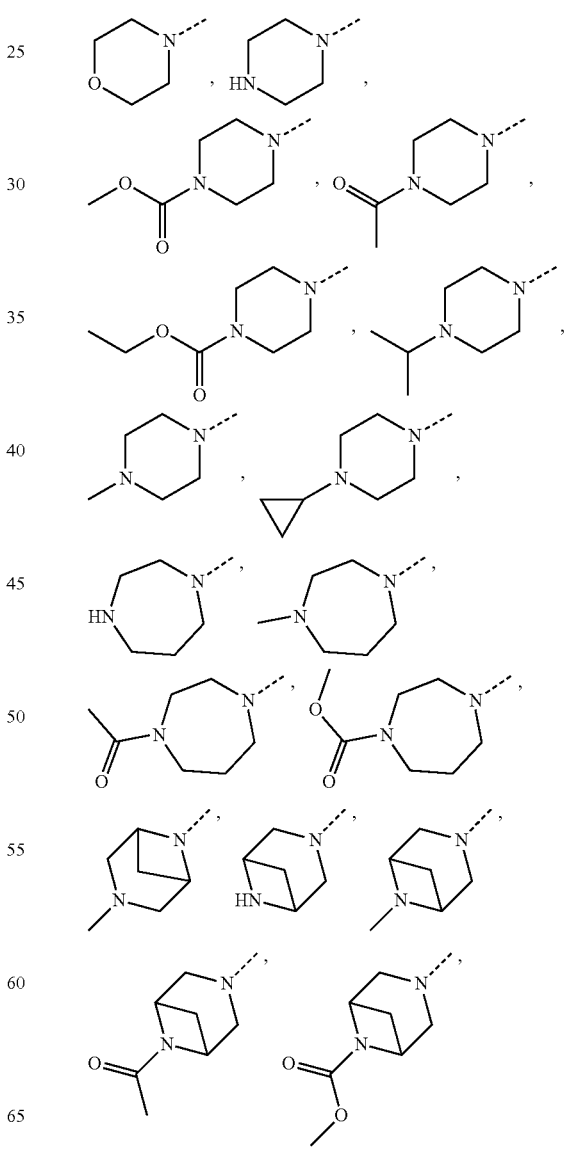

-continued
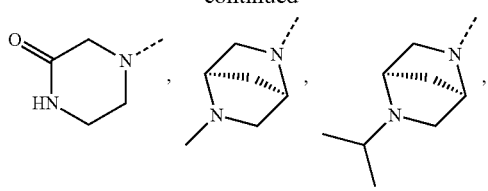
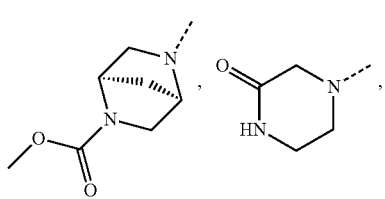
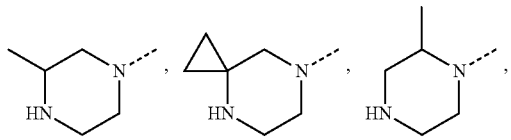
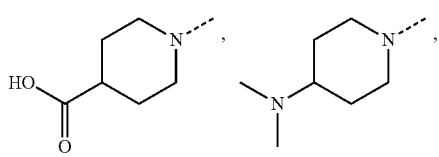
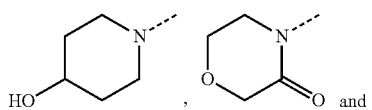
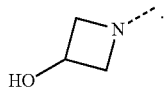
15. The compound, the optical isomer or the pharmaceutically acceptable salt thereof according to claim 2, which is selected from:
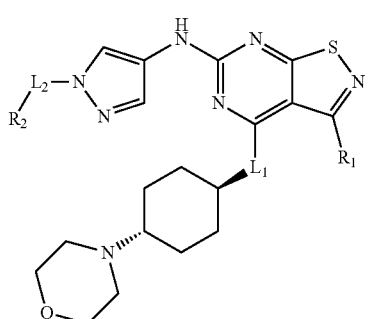
(III-1)
-continued
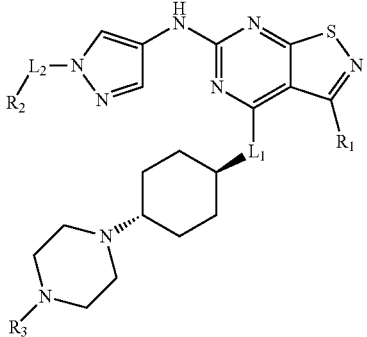
(III-2)
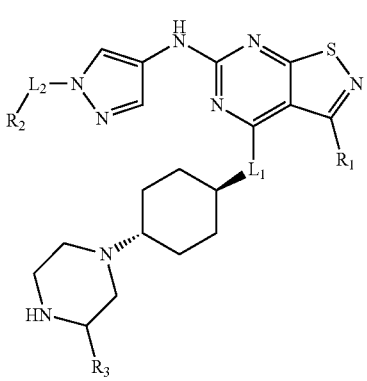
(III-3)
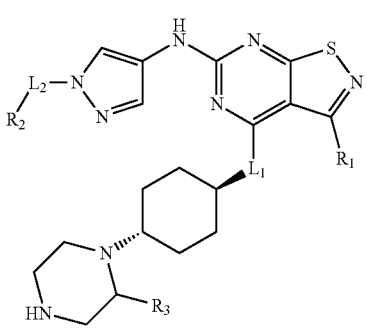
(III-4)
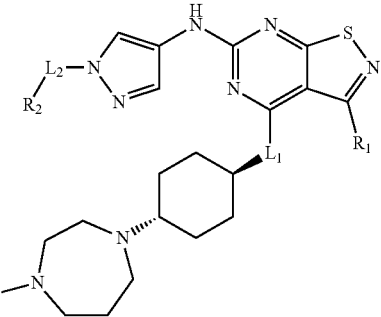
(III-5)

(III-6)
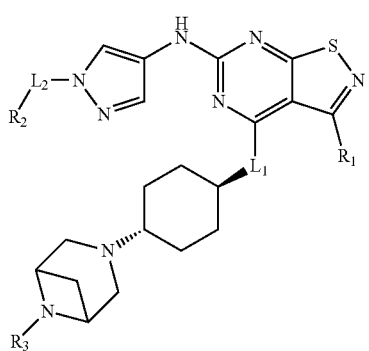
(III-7)
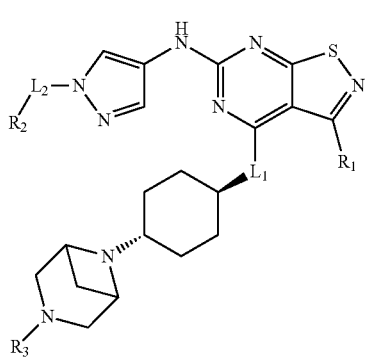
(III-8)
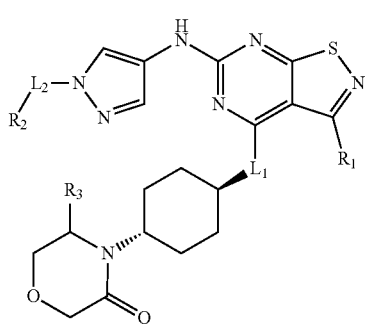
(III-9)
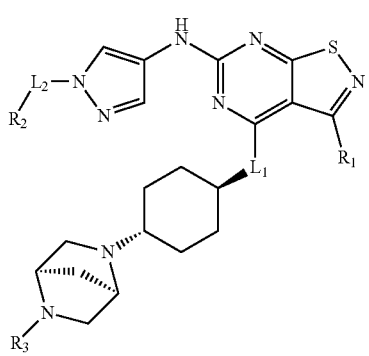
(III-10)
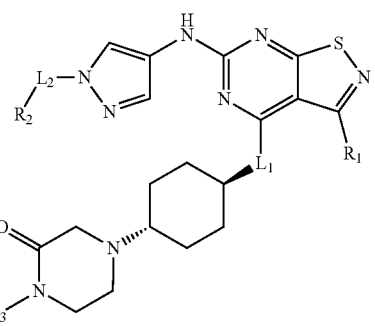
(III-11)
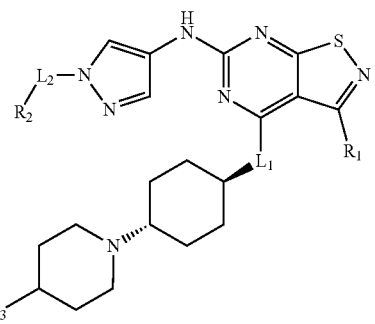
(III-12)
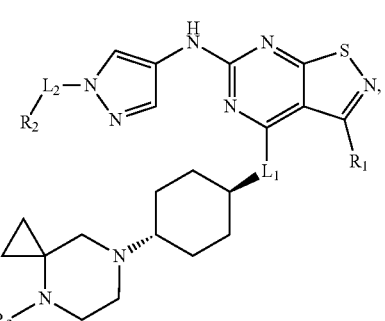
(III-13)
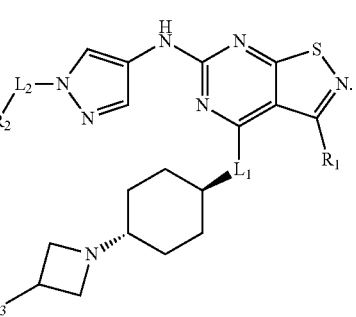
16. A compound of the following formula, an optical isomer or a pharmaceutically acceptable salt thereof, which is selected from:

123
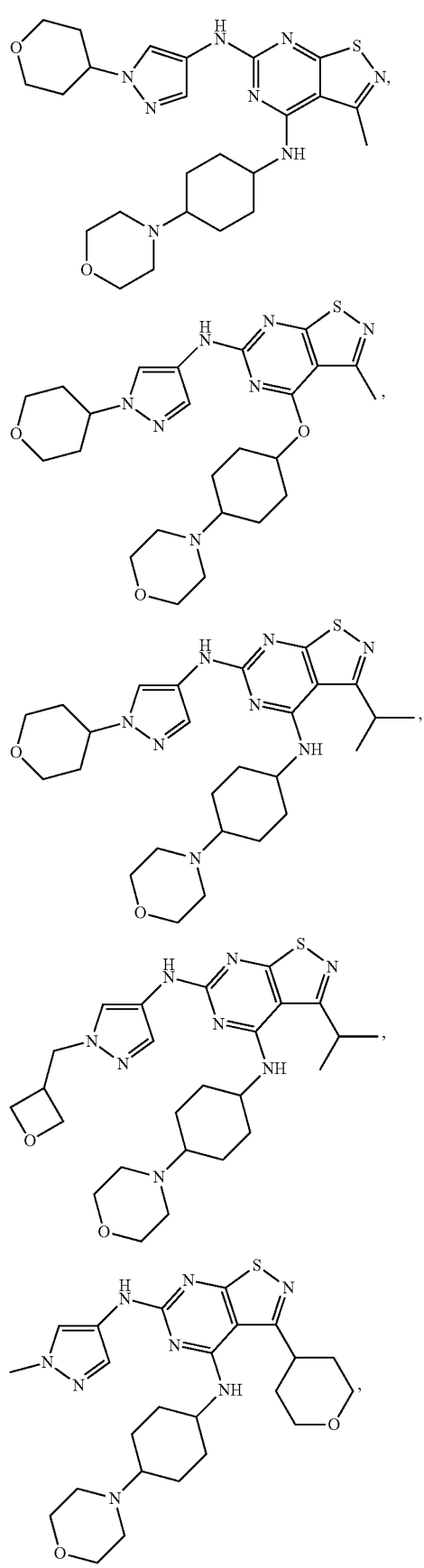
124
-continued
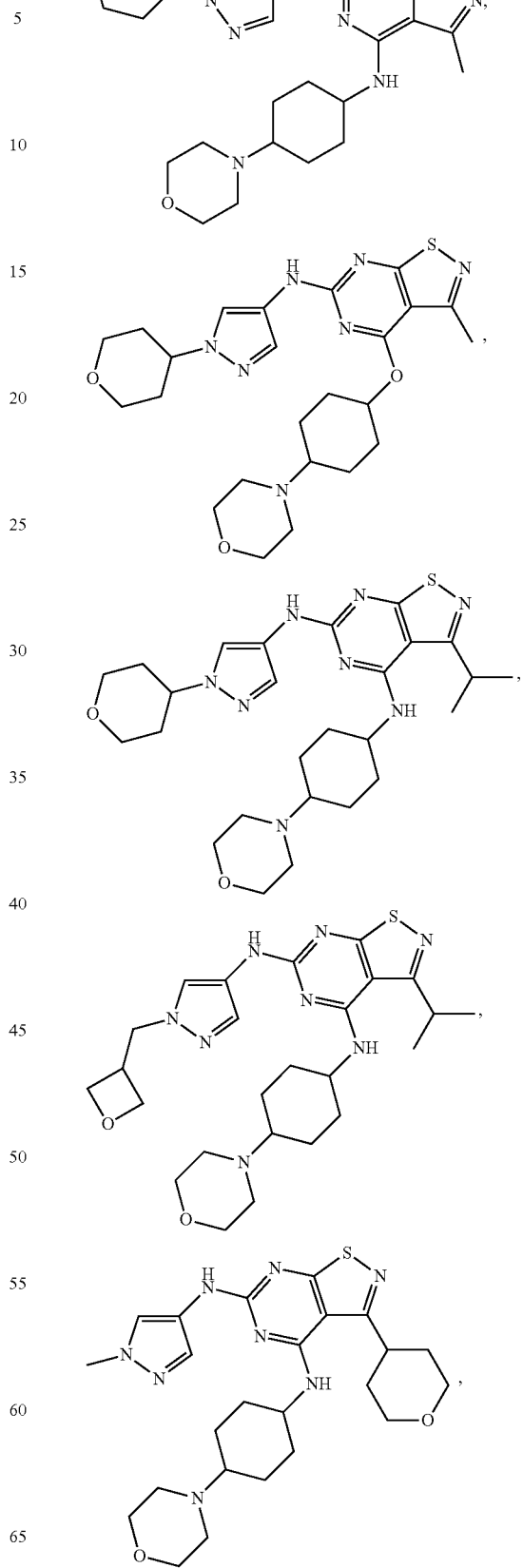

125
-continued
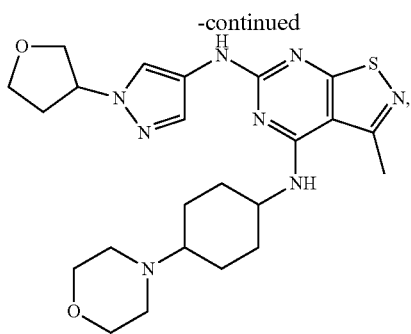
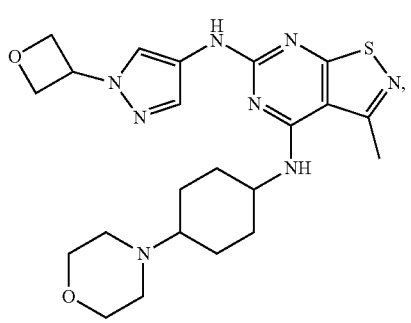
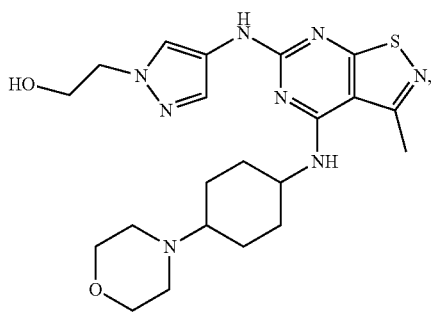
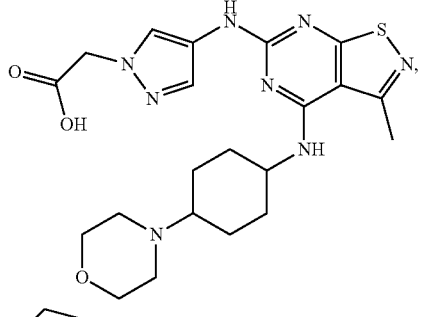
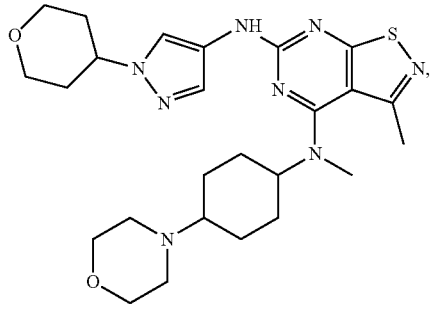
126
-continued
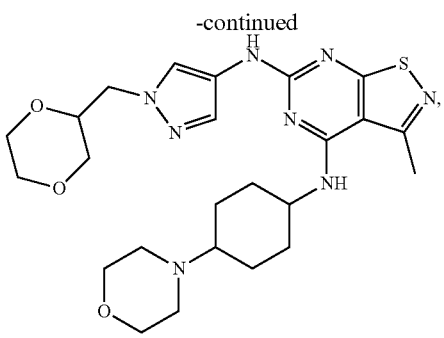
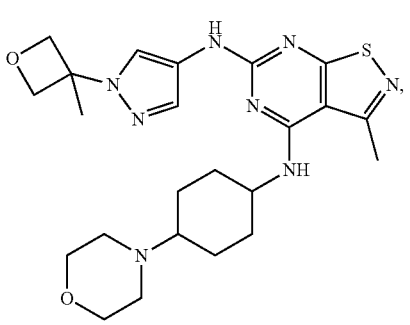
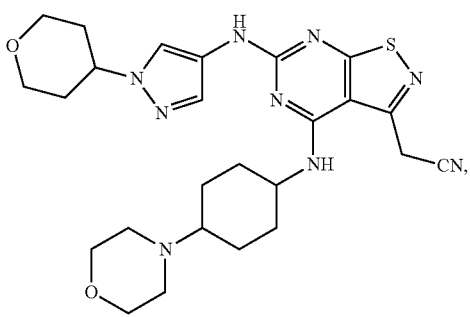
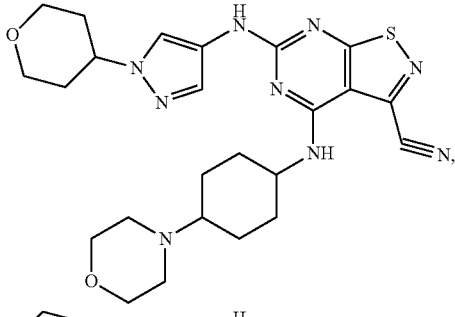
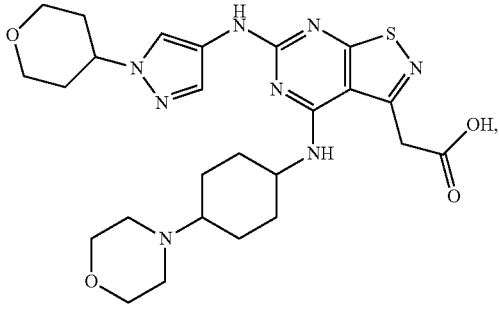

127
-continued
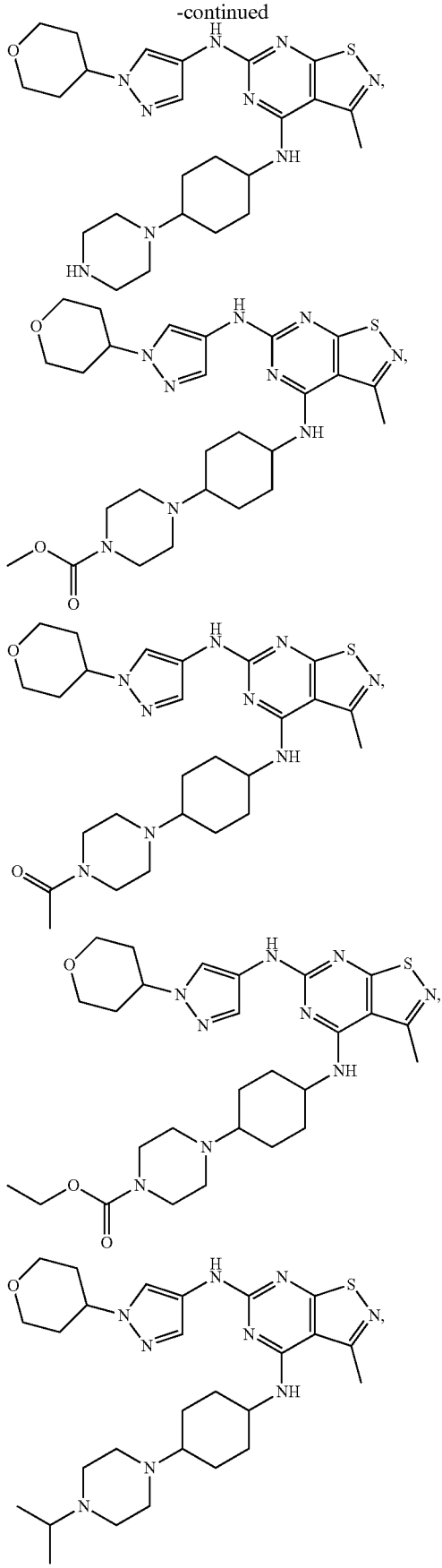
128
-continued
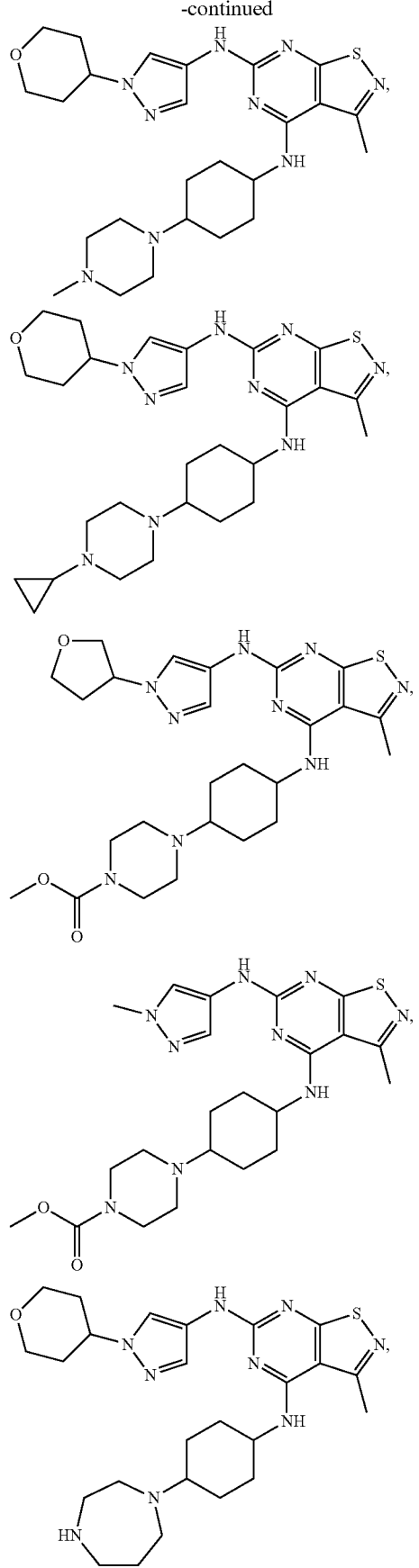

129
-continued
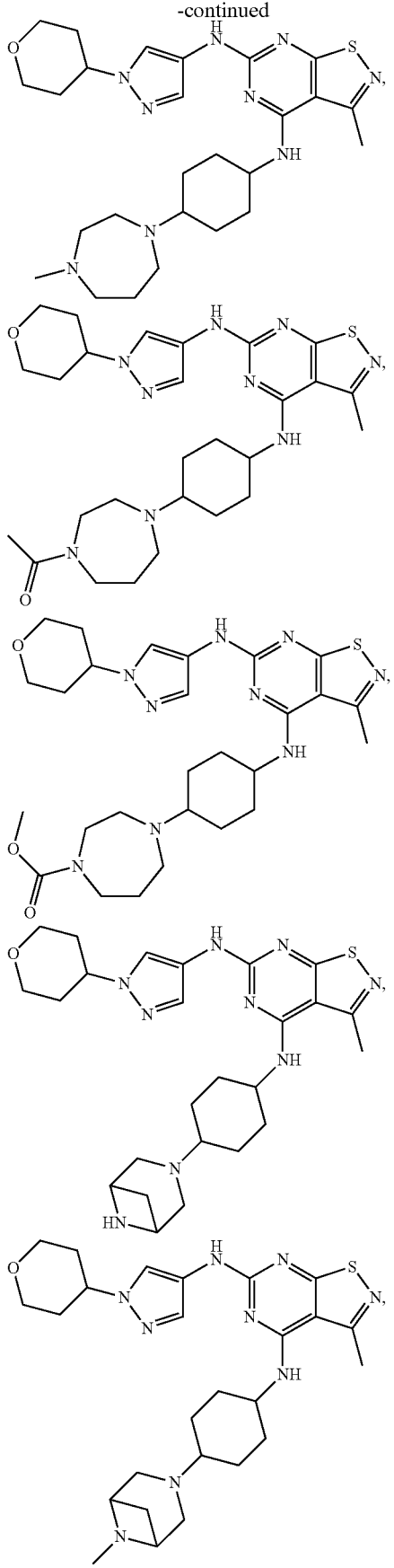
130
-continued
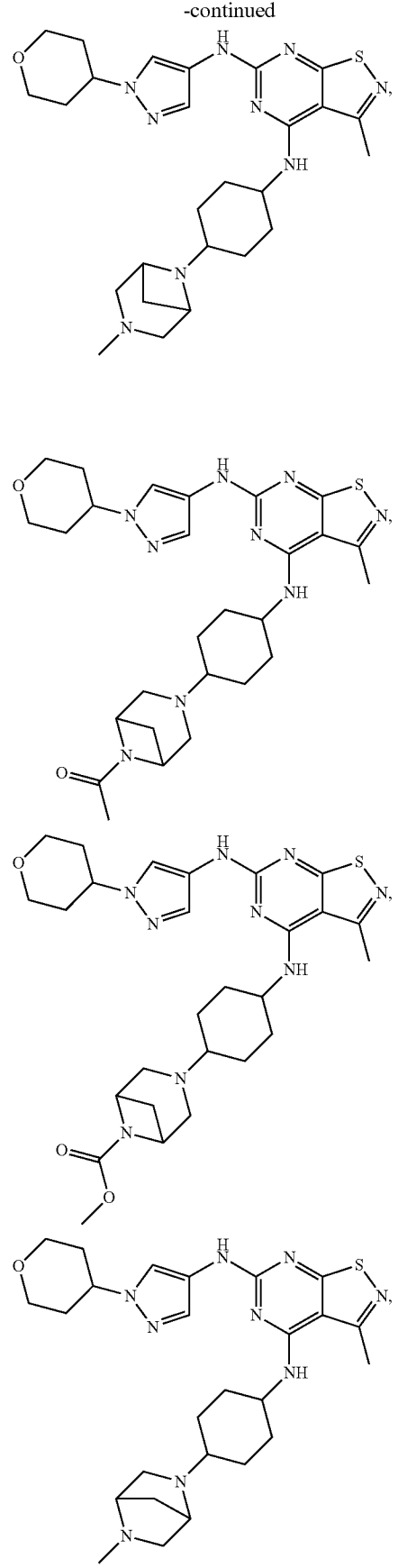

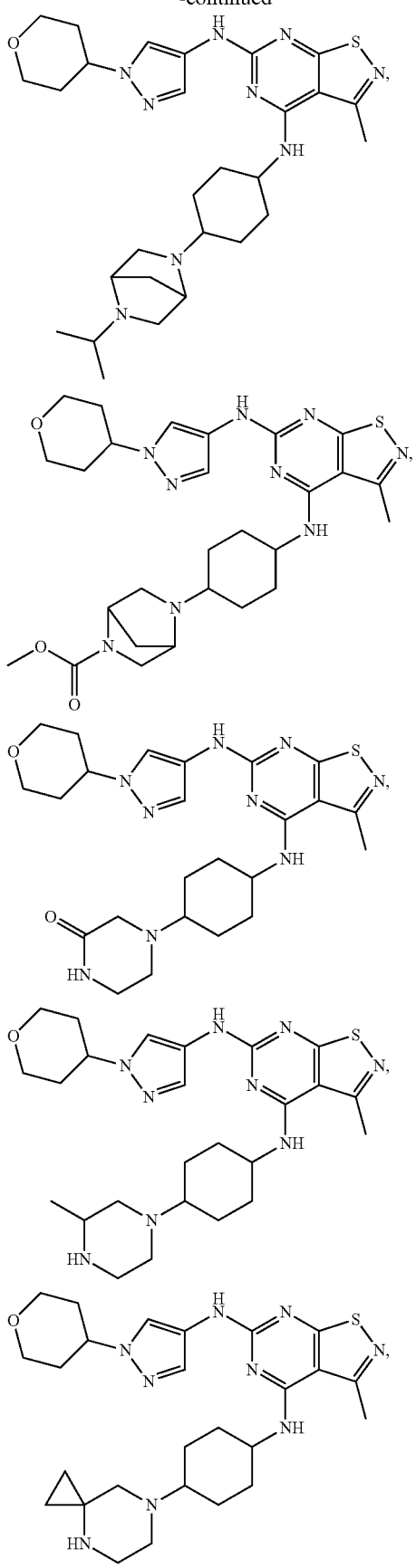
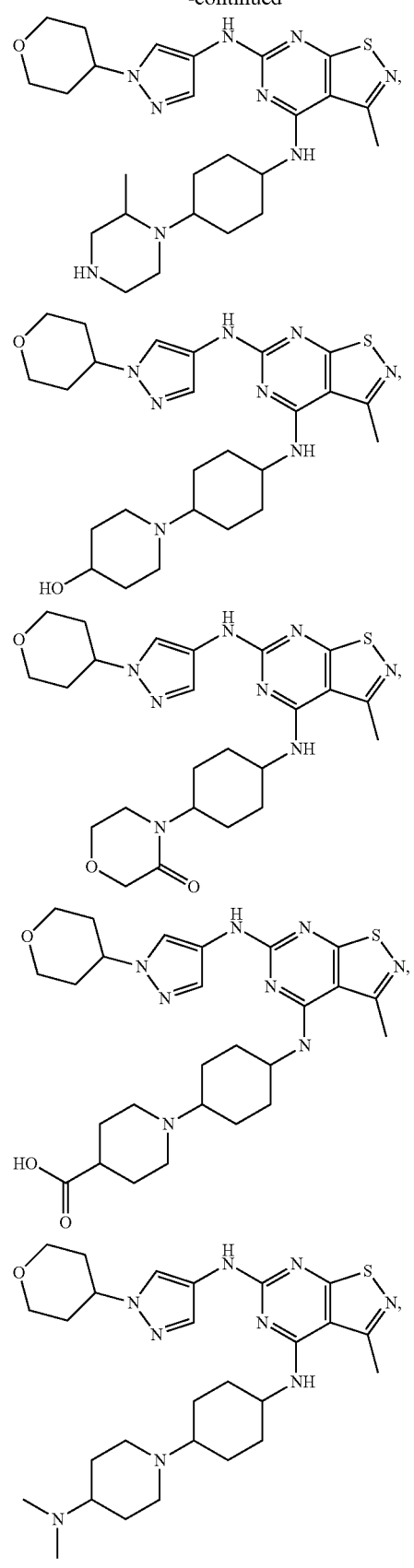

133
-continued
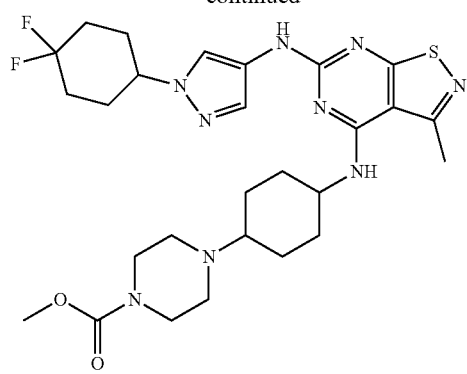 and
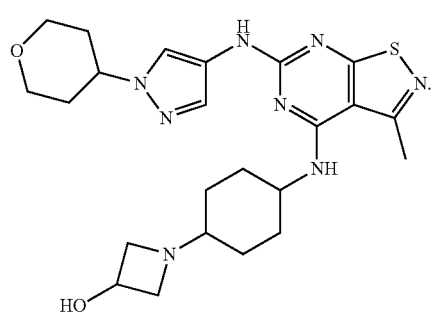 [SMILES: Cc1nsc2nc(Nc3cnn(C4CCOCC4)c3)nc(NC3CCC(N4CC(O)C4)CC3)c12]
17. The compound, the optical isomer or the pharmaceutically acceptable salt thereof according to claim 16, which is selected from:
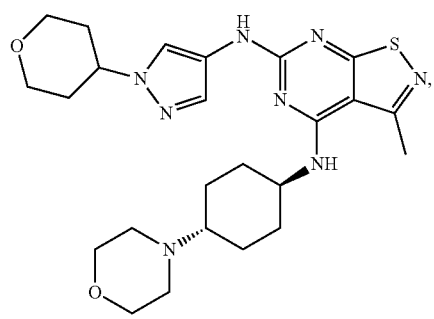
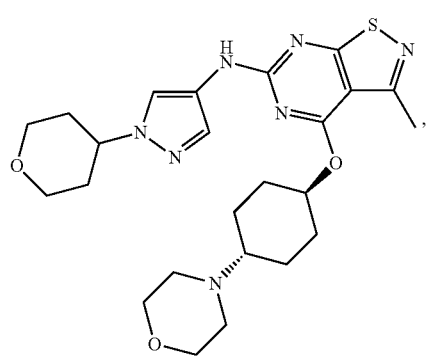
134
-continued
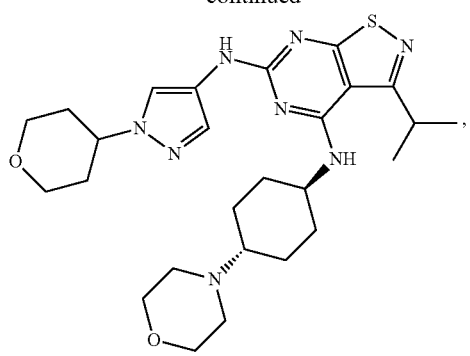
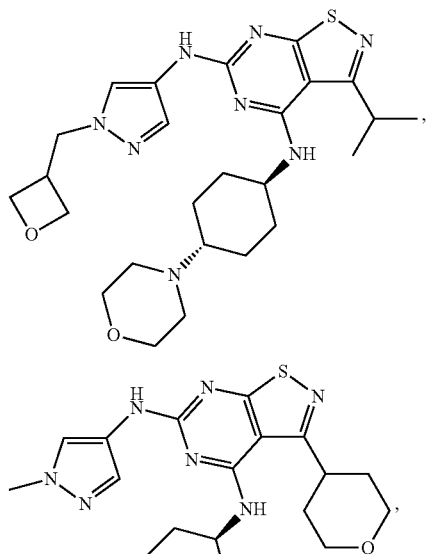
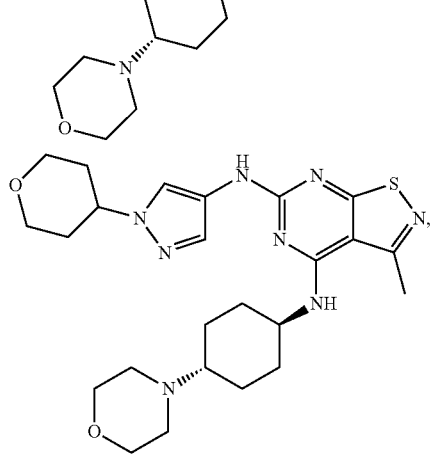
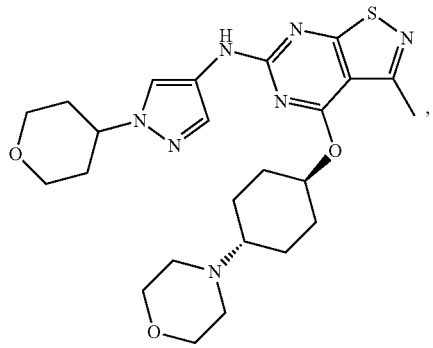

135
-continued
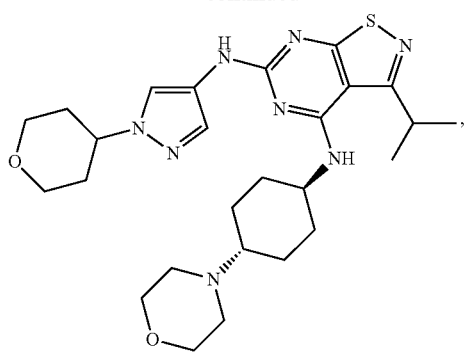
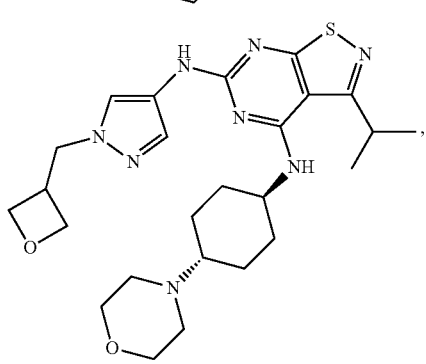
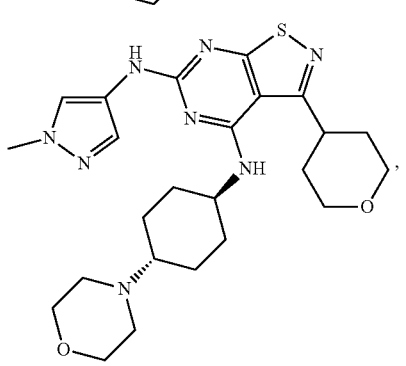
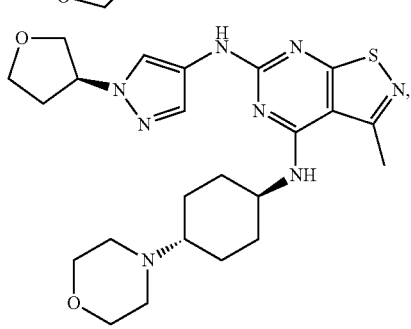
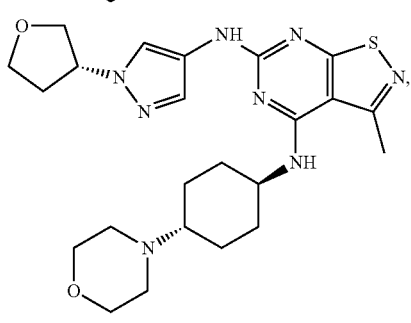
136
-continued
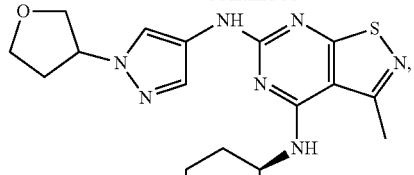
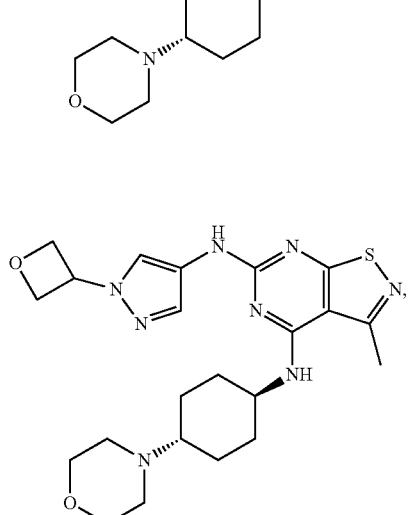
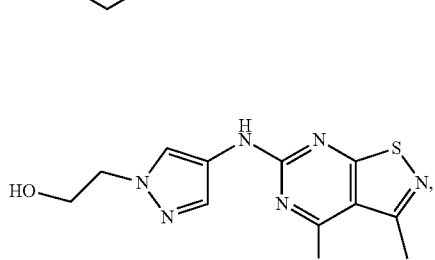
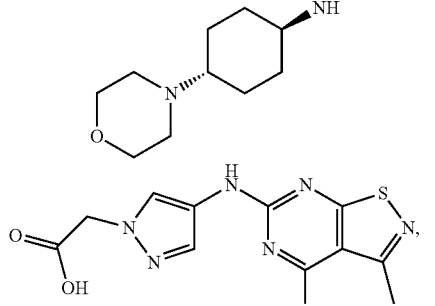
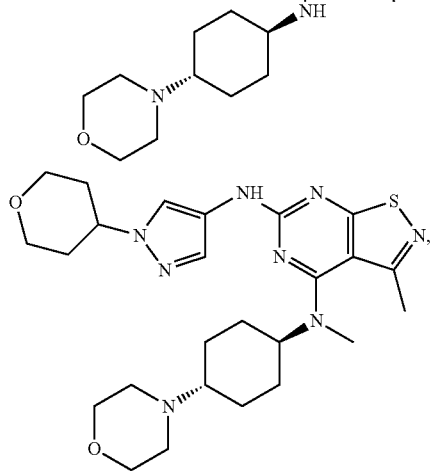

137
-continued
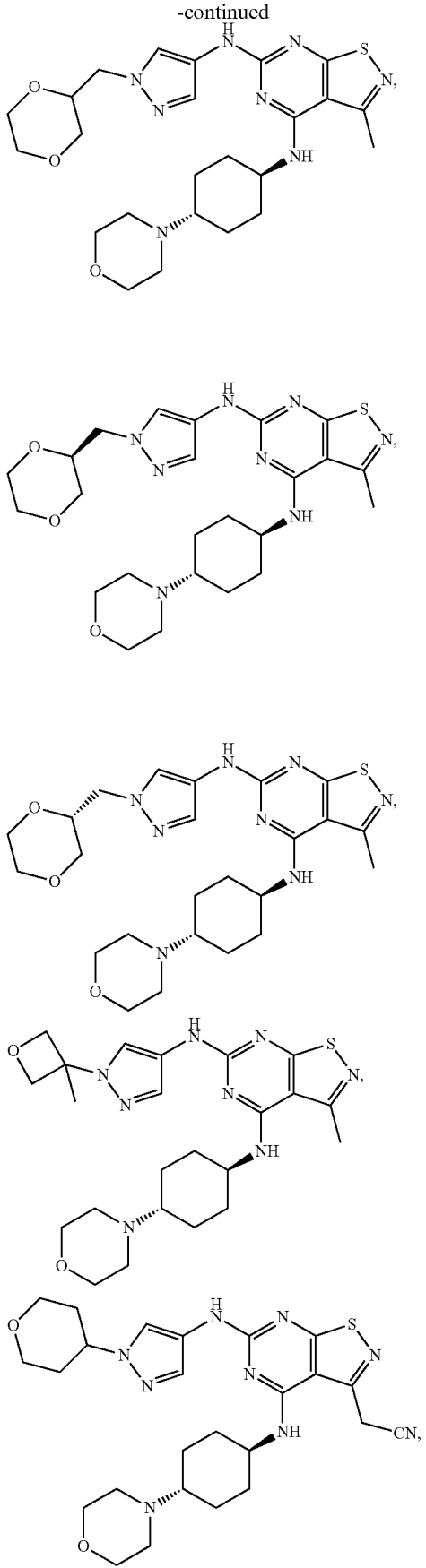
138
-continued
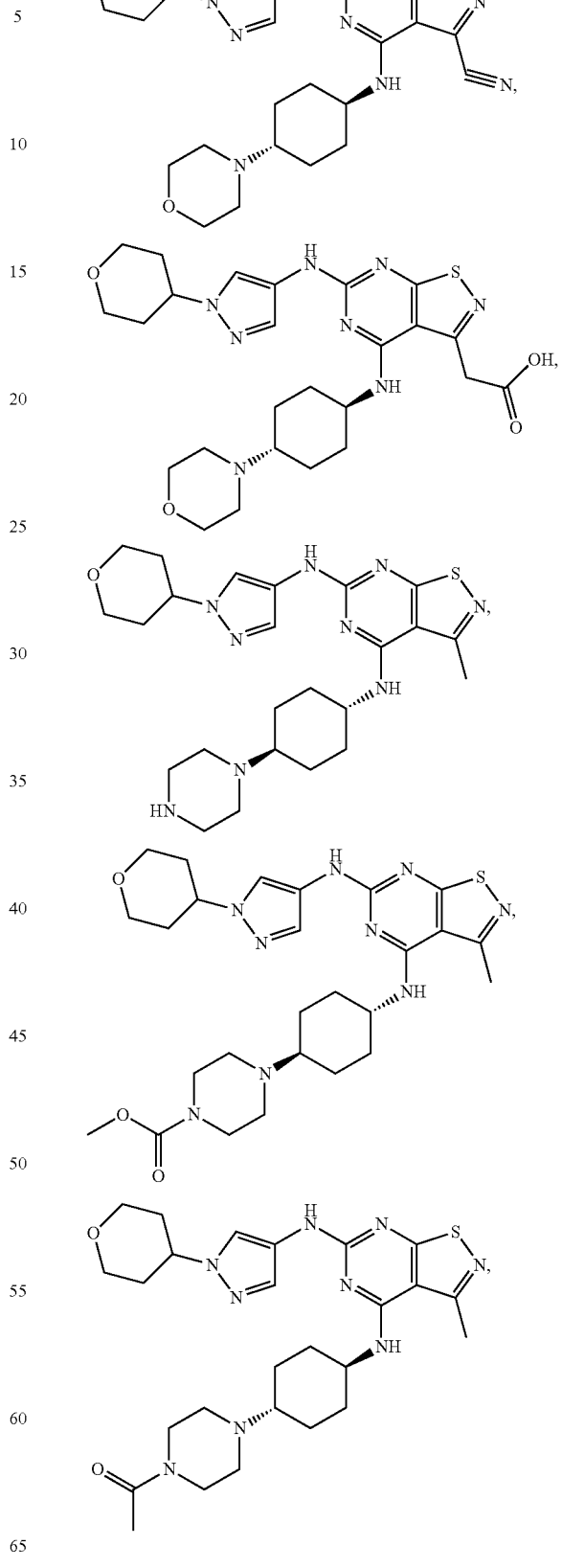

139
-continued
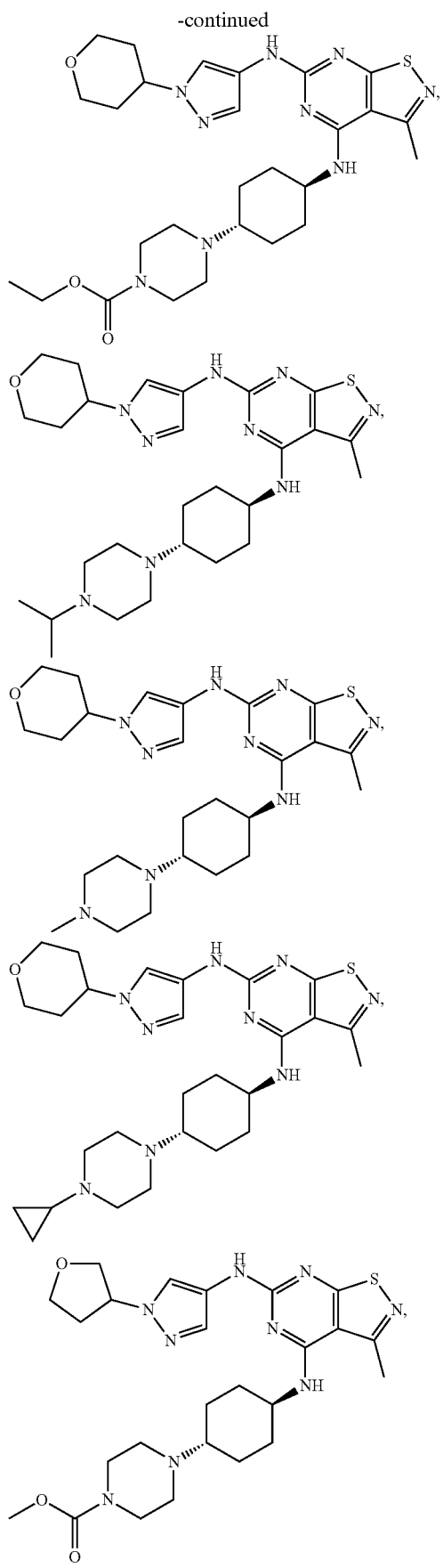
140
-continued
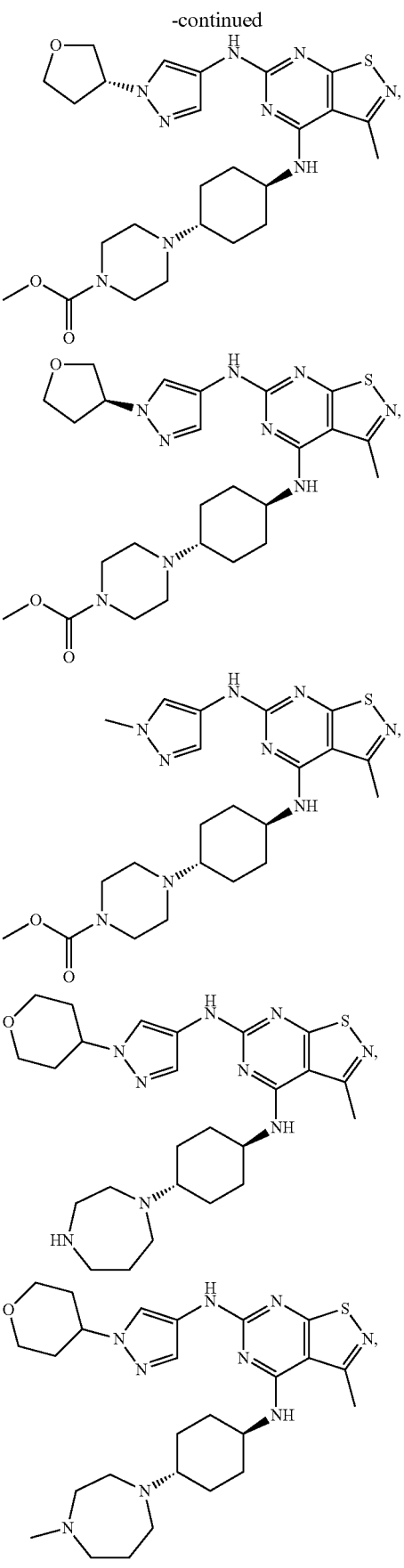

141
-continued
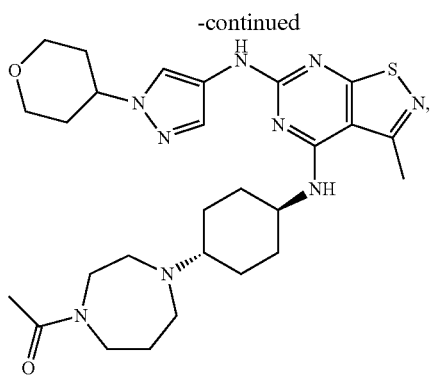
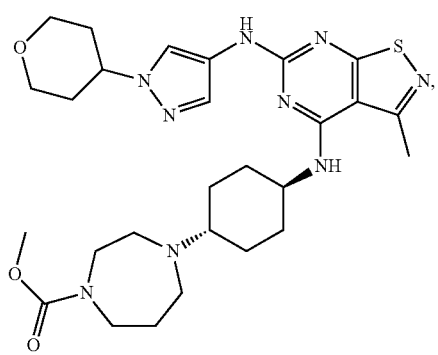
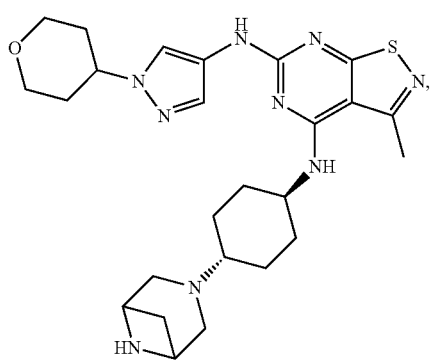
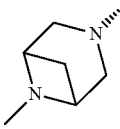
142
-continued
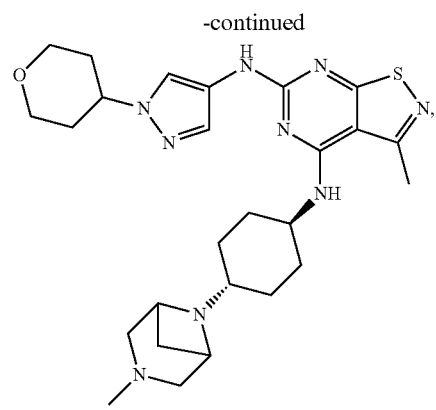
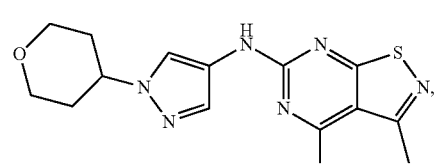
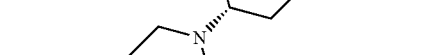
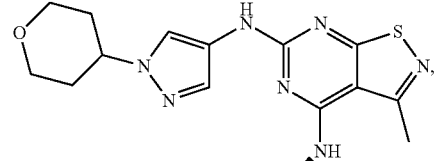

143
-continued
144
-continued
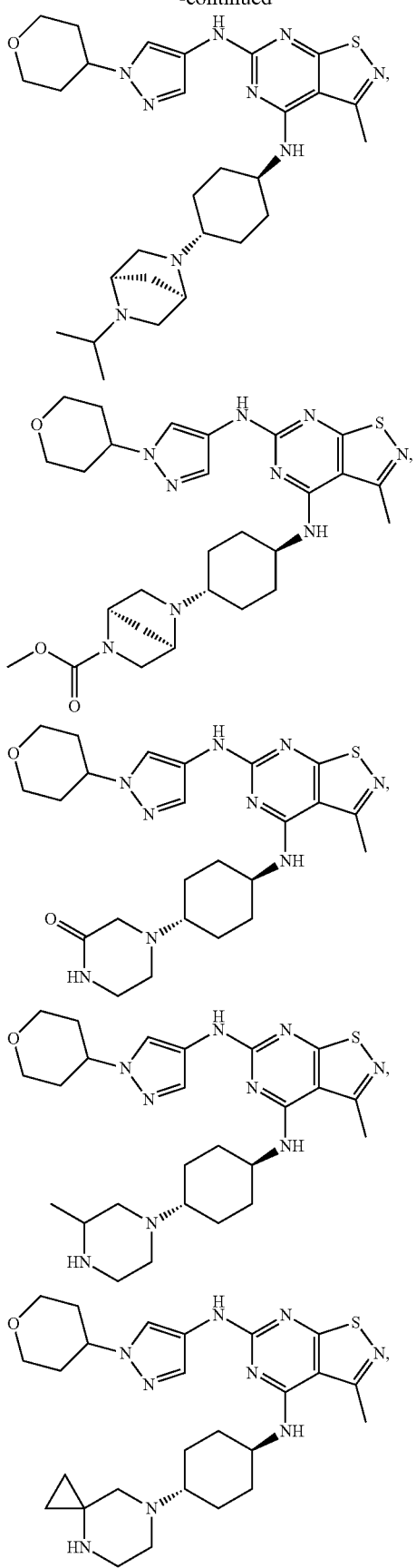
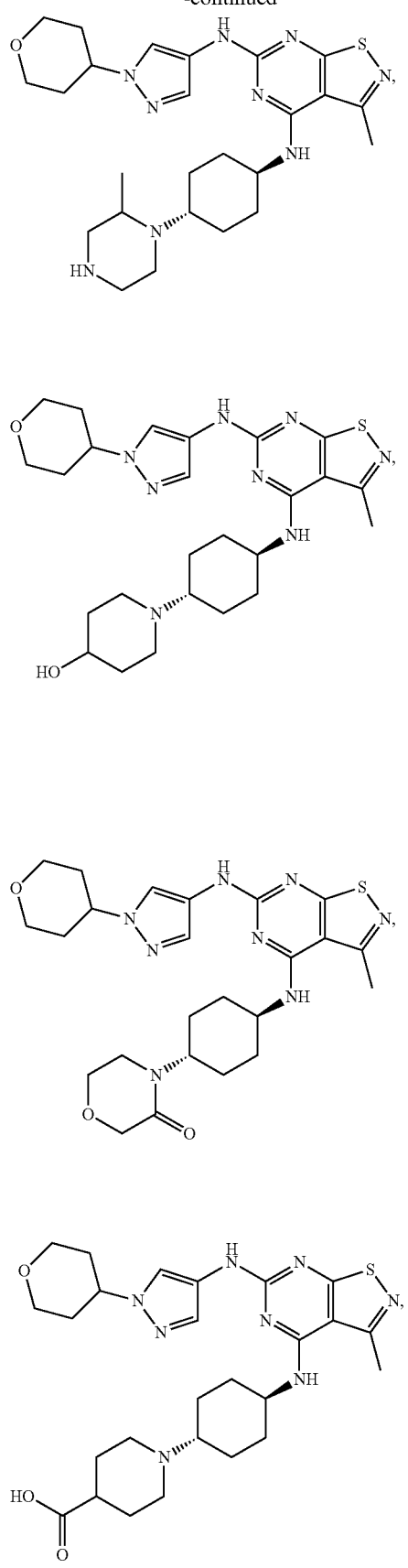

-continued

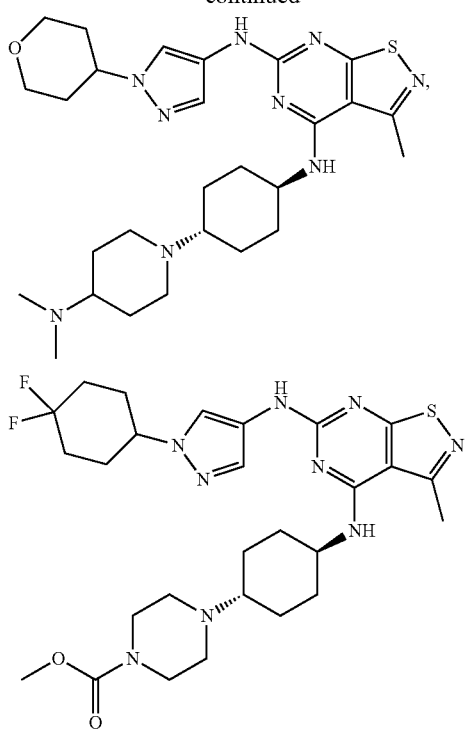

and

-continued

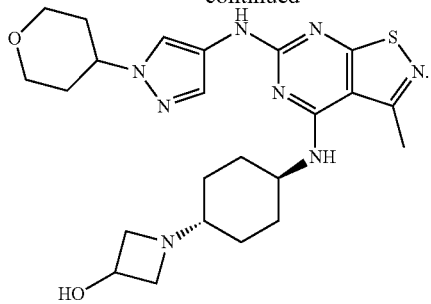

18. A pharmaceutical composition comprising a therapeutically effective amount of the compound, the isomer or the pharmaceutically acceptable salt thereof according to claim 2 as an active ingredient, and a pharmaceutically acceptable carrier.

19. A method for treating IRAK4-related diseases in a mammal, comprising administering to the mammal in need thereof a therapeutically effective amount of the compound, the isomer thereof or the pharmaceutically acceptable salt thereof according to claim 2, wherein the IRAK4-related diseases are inflammatory diseases.

20. A method for treating IRAK4-related diseases in a mammal, comprising administering to the mammal in need thereof a therapeutically effective amount of the composition according to claim 18, wherein the IRAK4-related diseases are inflammatory diseases.

\* \* \* \* \*

UNITED STATES PATENT AND TRADEMARK OFFICE
CERTIFICATE OF CORRECTION

| | | |
|---|---|---|
| PATENT NO. | : 11,459,337 B2 | |
| APPLICATION NO. | : 17/254778 | |
| DATED | : October 4, 2022 | |
| INVENTOR(S) | : Zhang et al. | |

It is certified that error appears in the above-identified patent and that said Letters Patent is hereby corrected as shown below:

In the Claims

At Column 116, Line 31 (Claim 9, Line 2), please delete "according to claim 1" and insert --according to claim 2-- therefor.

Signed and Sealed this
Twenty-eighth Day of February, 2023

Katherine Kelly Vidal
*Director of the United States Patent and Trademark Office*